(12) United States Patent
Fallin et al.

(10) Patent No.: US 10,342,529 B2
(45) Date of Patent: Jul. 9, 2019

(54) OSTEOTOMY GUIDE AND METHOD

(75) Inventors: Thomas Wade Fallin, Hyde Park, UT (US); M. Mary Sinnott, Logan, UT (US); Kwan-Ho Chan, Singapore (SG); Patrick M. White, West Chester, PA (US)

(73) Assignee: Smith & Nephew, Inc., Memphis, TN (US)

( * ) Notice: Subject to any disclaimer, the term of this patent is extended or adjusted under 35 U.S.C. 154(b) by 977 days.

(21) Appl. No.: 14/131,591

(22) PCT Filed: Jul. 5, 2012

(86) PCT No.: PCT/US2012/045584
§ 371 (c)(1),
(2), (4) Date: Jan. 8, 2014

(87) PCT Pub. No.: WO2013/009574
PCT Pub. Date: Jan. 17, 2013

(65) Prior Publication Data
US 2014/0188139 A1 Jul. 3, 2014

Related U.S. Application Data

(60) Provisional application No. 61/505,992, filed on Jul. 8, 2011, provisional application No. 61/506,000, filed
(Continued)

(51) Int. Cl.
*A61B 17/04* (2006.01)
*A61B 17/15* (2006.01)
(Continued)

(52) U.S. Cl.
CPC ...... *A61B 17/0491* (2013.01); *A61B 17/0469* (2013.01); *A61B 17/0482* (2013.01);
(Continued)

(58) Field of Classification Search
CPC ............ A61B 17/0491; A61B 17/1714; A61B 17/8886; A61B 17/86; A61B 17/151;
(Continued)

(56) References Cited

U.S. PATENT DOCUMENTS 4,929,247 A 5/1990 Rayhack
5,042,983 A 8/1991 Rayhack
(Continued)

FOREIGN PATENT DOCUMENTS

CA 2750377 A1 7/2010
GB 2475491 A 5/2011
(Continued)

OTHER PUBLICATIONS

Australian Patent Examination Report; Australian Patent Office; Australian Patent Application No. 2012282919; dated Apr. 14, 2016; 3 pages.
(Continued)

*Primary Examiner* — David C Eastwood
*Assistant Examiner* — Erich Herbermann
(74) *Attorney, Agent, or Firm* — Taft Stettinius & Hollister LLP

(57) ABSTRACT

Improved surgical instruments are provided including improved suture passers, improved drill guides for forming holes in bones adjacent a joint at locations referenced to the joint anatomy, and improved osteotomy guides.

18 Claims, 86 Drawing Sheets

Related U.S. Application Data on Jul. 8, 2011, provisional application No. 61/506,004, filed on Jul. 8, 2011, provisional application No. 61/568,137, filed on Dec. 7, 2011, provisional application No. 13/527,359, filed on Jun. 19, 2012, provisional application No. 13/527,424, filed on Jun. 19, 2012, provisional application No. 13/527,648, filed on Jun. 20, 2012, provisional application No. 13/527,765, filed on Jun. 20, 2012.

(51) Int. Cl.

| | | |
|---|---|---|
| *A61B 17/16* | (2006.01) | |
| *A61B 17/17* | (2006.01) | |
| *A61B 17/86* | (2006.01) | |
| *A61B 17/88* | (2006.01) | |
| *A61F 2/08* | (2006.01) | |
| *A61B 17/06* | (2006.01) | |
| *A61B 17/14* | (2006.01) | |

(52) U.S. Cl.
CPC ........ *A61B 17/151* (2013.01); *A61B 17/1682* (2013.01); *A61B 17/1714* (2013.01); *A61B 17/1739* (2013.01); *A61B 17/1775* (2016.11); *A61B 17/1796* (2013.01); *A61B 17/86* (2013.01); *A61B 17/8886* (2013.01); *A61B 17/0483* (2013.01); *A61B 17/0485* (2013.01); *A61B 17/06166* (2013.01); *A61B 17/142* (2016.11); *A61B 17/1697* (2013.01); *A61B 2017/0404* (2013.01); *A61B 2017/06042* (2013.01); *A61F 2/0805* (2013.01); *A61F 2002/0882* (2013.01)

(58) Field of Classification Search
CPC ............ A61B 17/0482; A61B 17/1796; A61B 17/1739; A61B 17/1682; A61B 17/0469; A61B 17/142; A61B 17/1775; A61B 17/0485; A61B 17/06166; A61B 17/1697; A61B 17/0483; A61B 2017/0404; A61B 2017/06042; A61F 2/0805; A61F 2002/0882
USPC ....................................................... 606/145
See application file for complete search history.

(56) References Cited

U.S. PATENT DOCUMENTS

| | | | |
|---|---|---|---|
| 5,059,201 A | 10/1991 | Asnis | |
| 5,176,685 A | 1/1993 | Rayhack | |
| 6,007,535 A | 12/1999 | Rayhack et al. | |
| 7,118,583 B2 | 10/2006 | O'Quinn et al. | |
| 7,815,654 B2* | 10/2010 | Chu ................... | A61B 17/0469 606/139 |
| 8,282,657 B2* | 10/2012 | McClurg ............ | A61B 17/0469 606/139 |
| 2003/0078599 A1 | 4/2003 | O'Quinn et al. | |
| 2003/0078600 A1 | 4/2003 | O'Quinn et al. | |
| 2003/0216742 A1 | 11/2003 | Wetzler et al. | |
| 2004/0015177 A1 | 1/2004 | Chu | |
| 2007/0083362 A1 | 4/2007 | Bonutti et al. | |
| 2007/0233128 A1 | 10/2007 | Schmieding et al. | |
| 2009/0254126 A1 | 10/2009 | Orbay et al. | |
| 2010/0057216 A1 | 3/2010 | Gannoe et al. | |
| 2010/0324563 A1 | 12/2010 | Green, II et al. | |
| 2011/0028998 A1* | 2/2011 | Adams ............... | A61B 17/0469 606/145 |
| 2011/0066165 A1 | 3/2011 | Skinlo et al. | |
| 2011/0144647 A1 | 6/2011 | Appenzeller et al. | |

FOREIGN PATENT DOCUMENTS

| | | |
|---|---|---|
| JP | 2014528768 A | 10/2014 |
| WO | 1991006247 A1 | 5/1991 |
| WO | 2008043380 A1 | 4/2008 |
| WO | 2008076559 A1 | 6/2008 |

OTHER PUBLICATIONS

International Search Report; International Searching Authority; International PCT Application No. PCT/US2012/045584; dated Jan. 31, 2013; 3 pages.

Written Opinion; International Searching Authority; International PCT Application No. PCT/US2012/045584; dated Jan. 31, 2013; 4 pages.

International Preliminary Report on Patentability; The International Bureau of WIPO; International PCT Application No. PCT/US2012/045584; dated Jan. 14, 2014; 5 pages.

Supplementary Partial European Search Report; European Patent Office; European Patent Application No. 12810809.9; dated Apr. 1, 2015; 6 pages.

Extended European Search Report; European Patent Office; European Application No. 12810809.9; dated Feb. 15, 2016; 21 pages.

Japanese Notice of Reasons for Rejection; Japanese Patent Office; Japanese Patent Application No. 2014-519300; dated Jun. 20, 2016; 11 pages.

Chinese Search Report; Chinese Patent Office; Chinese Patent Application No. 201280043613.2; dated Oct. 20, 2016; 4 pages.

Chinese Decision of Rejection; Chinese Patent Office; Chinese Patent Application No. 201280043613.2; dated Nov. 1, 2016; 15 pages.

Japanese Notice of Reasons for Rejection; Japanese Patent Office; Japanese Patent Application No. 2014-519300; dated Mar. 27, 2017; 5 pages.

\* cited by examiner

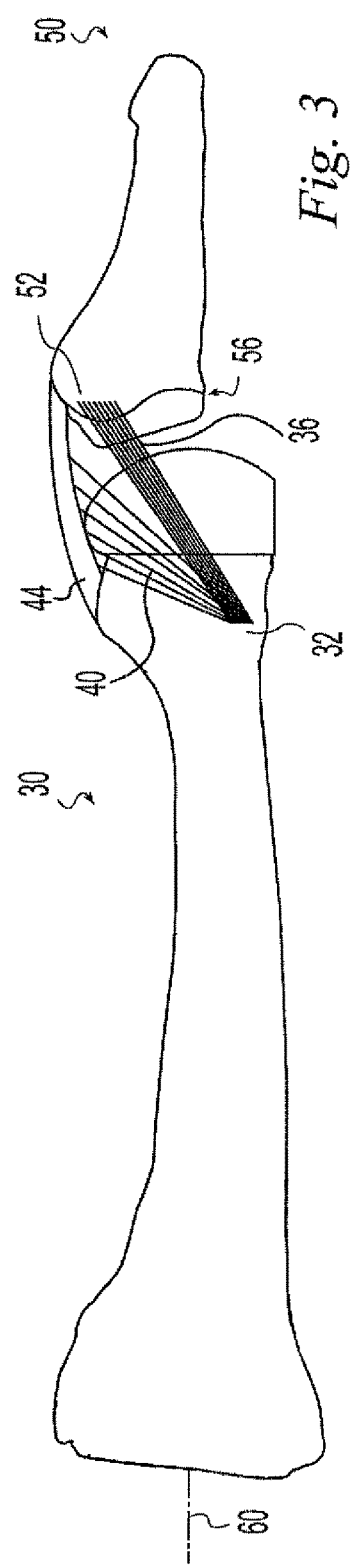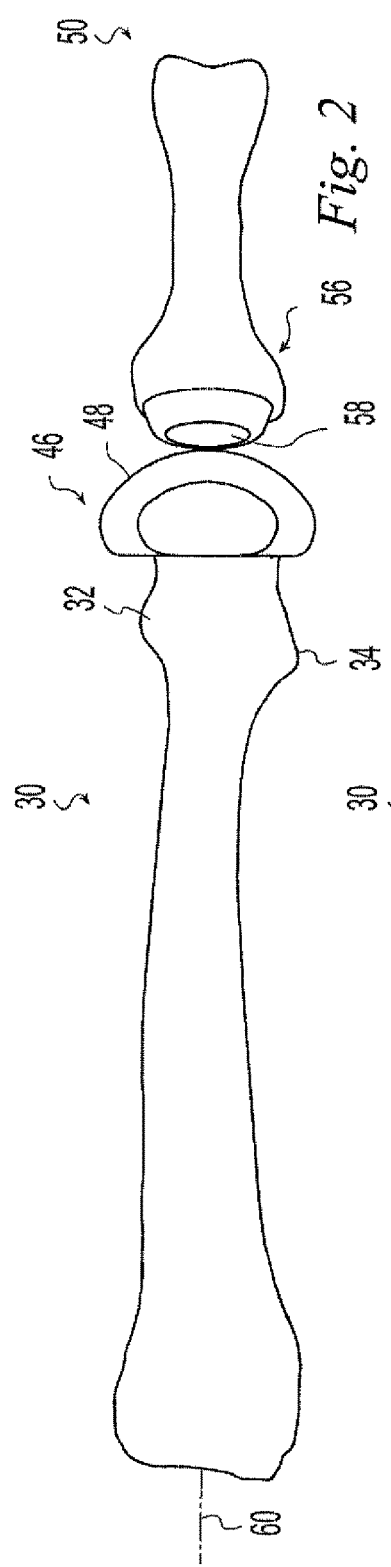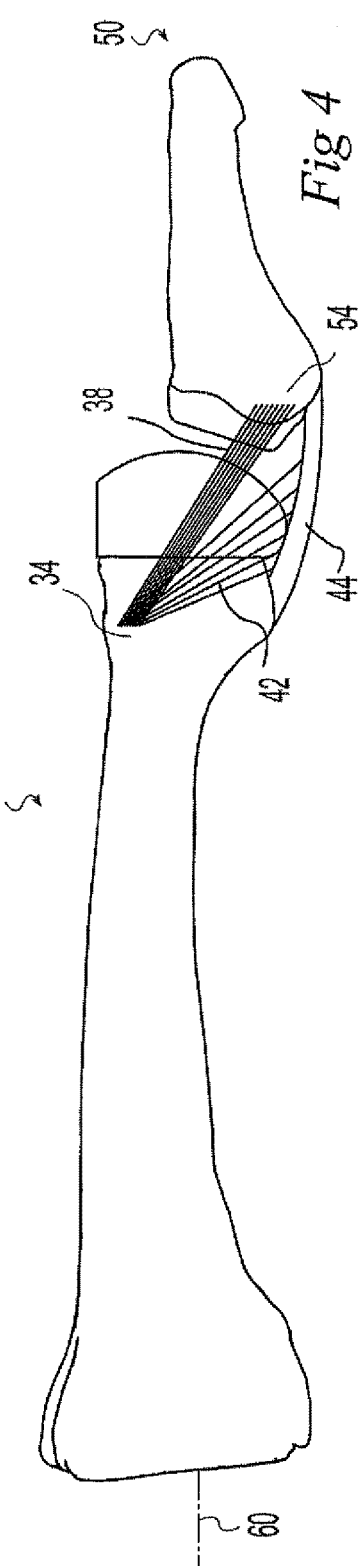

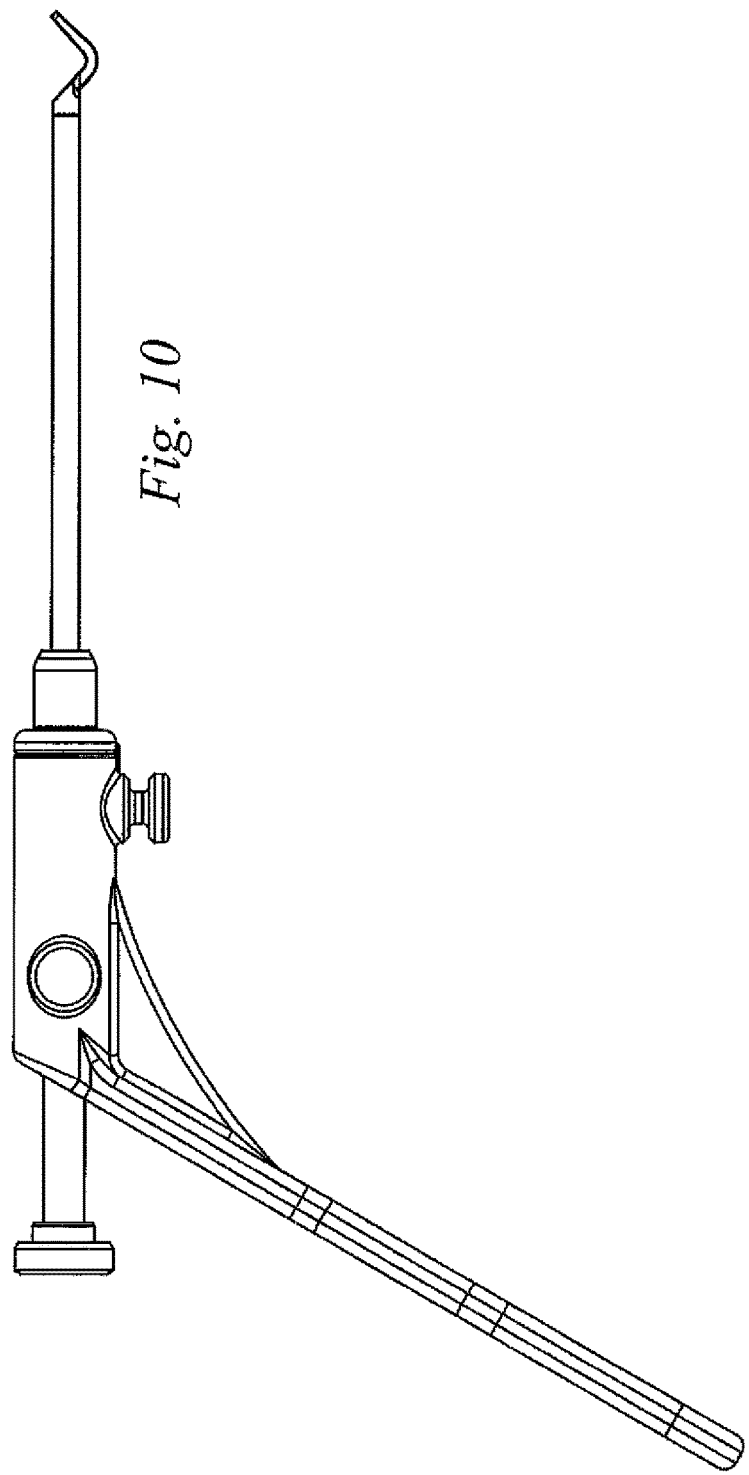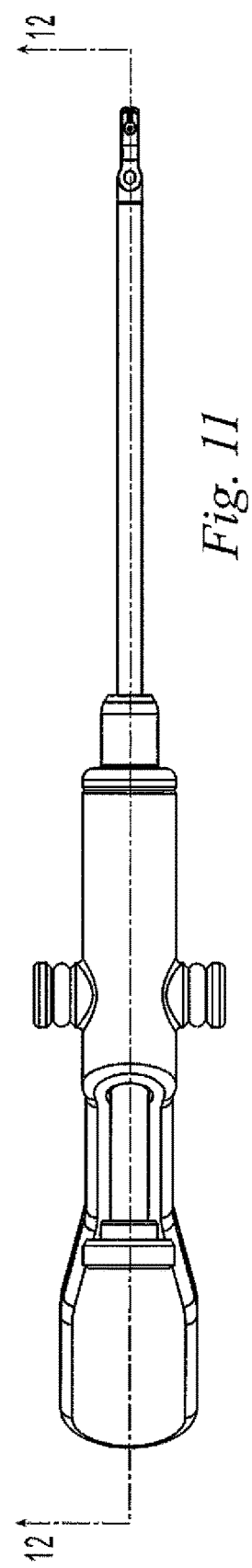

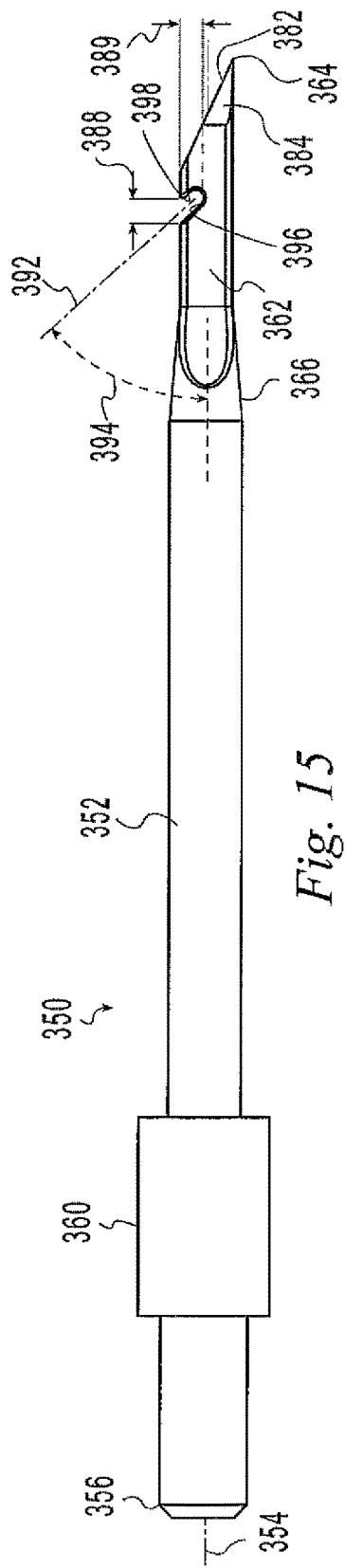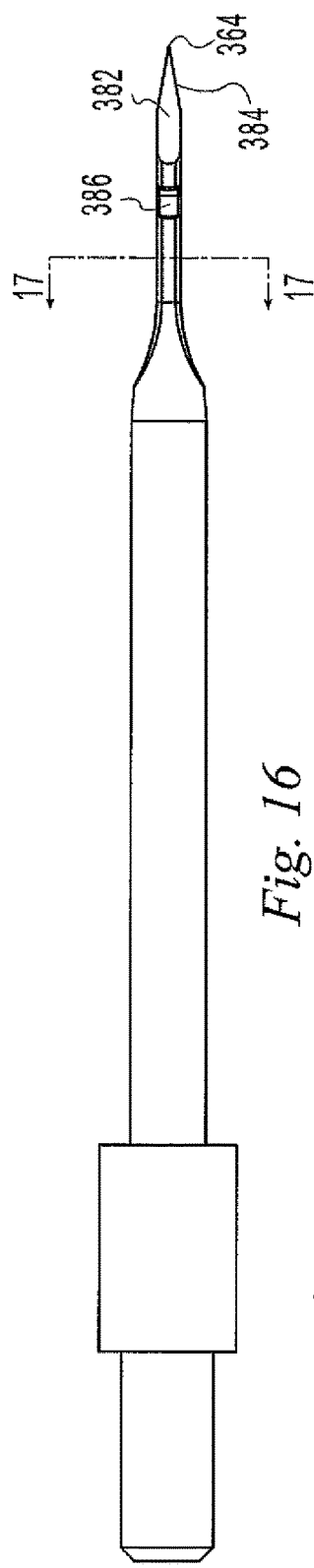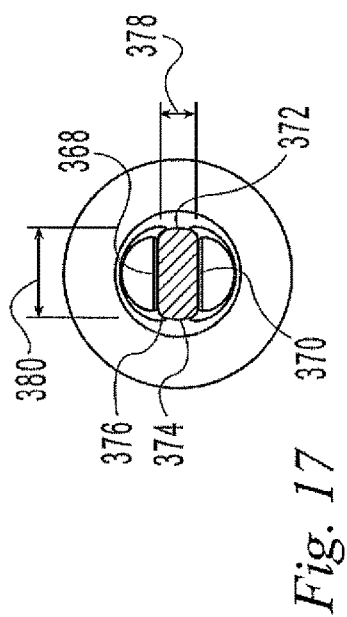

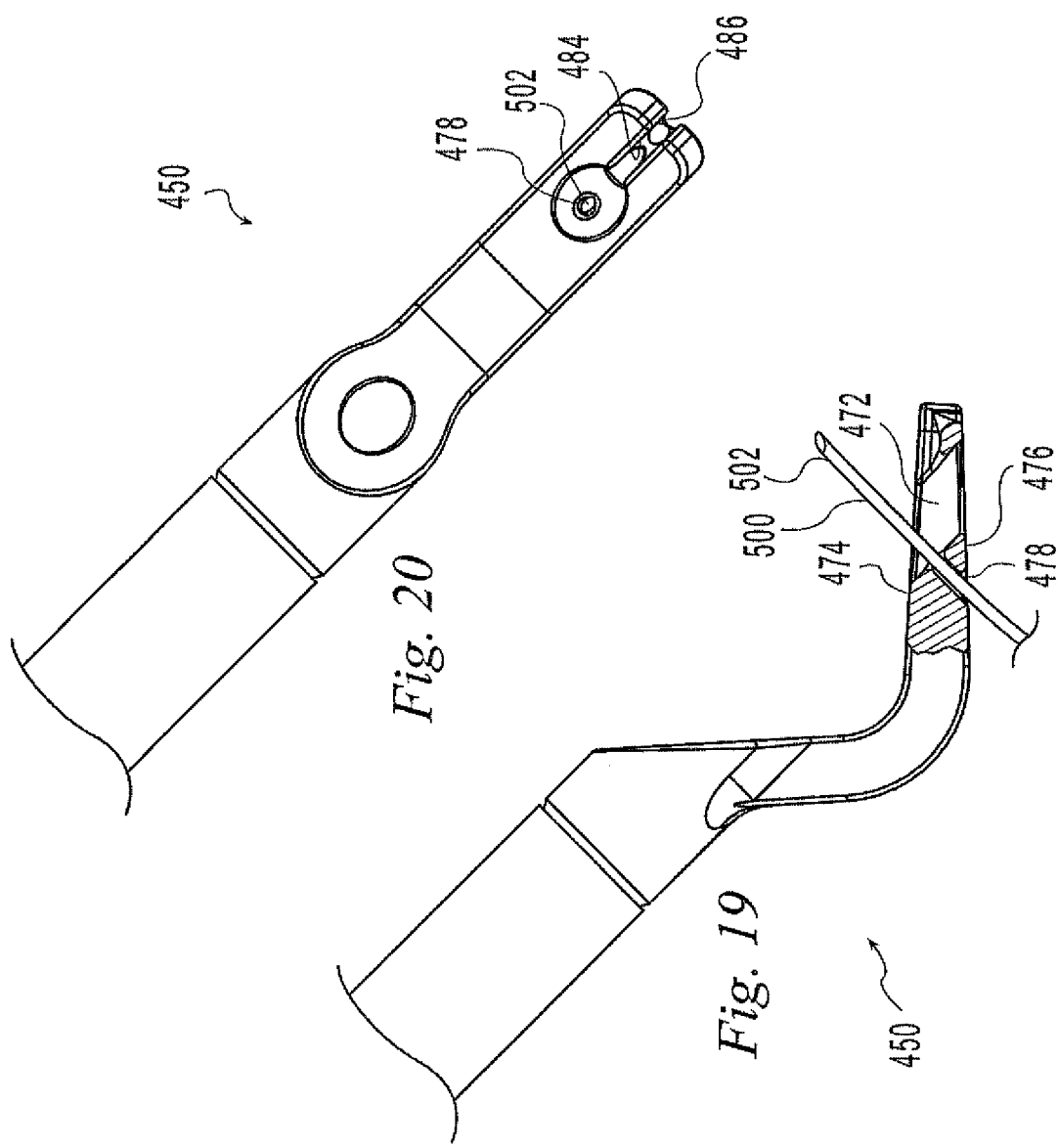

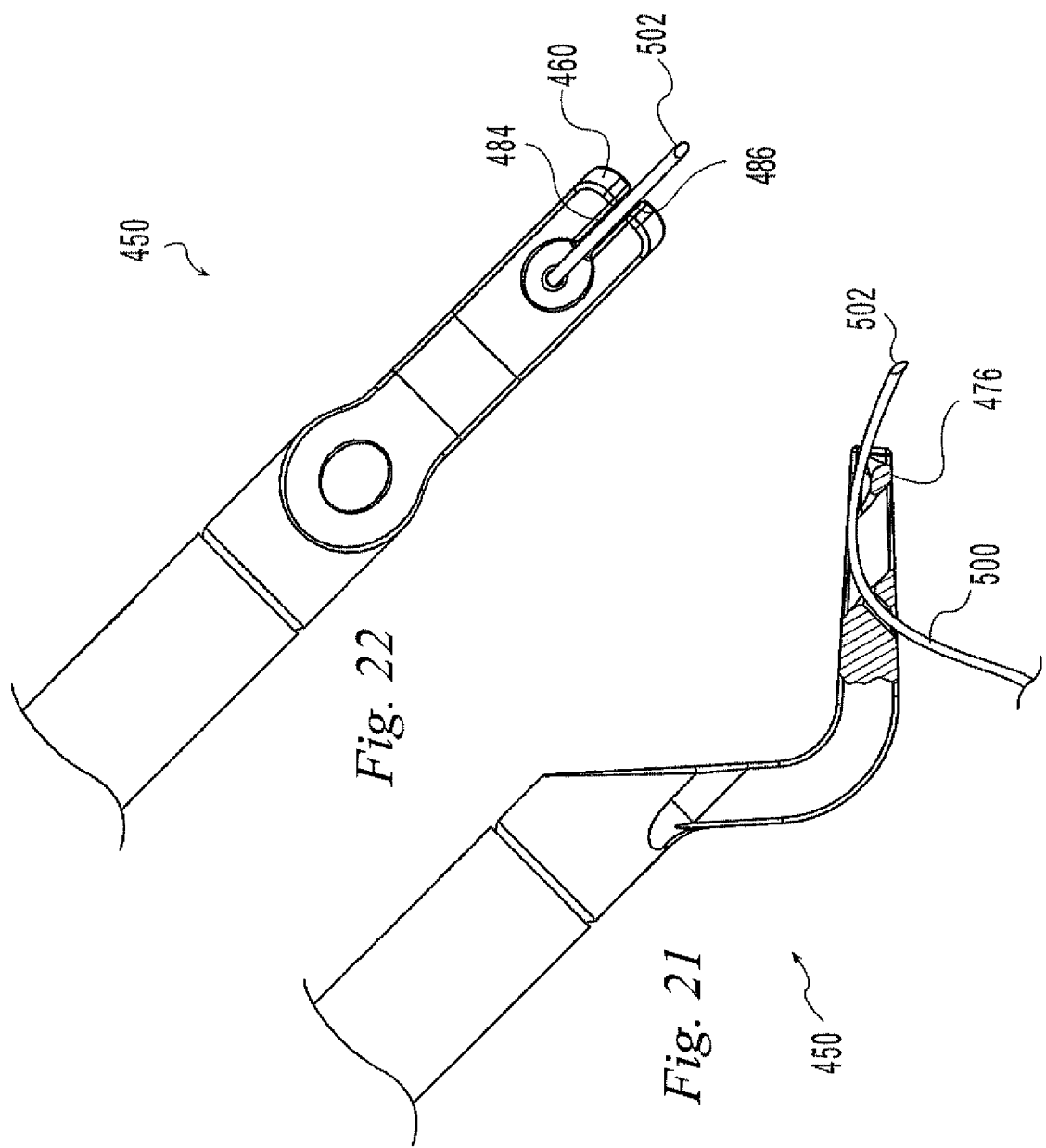

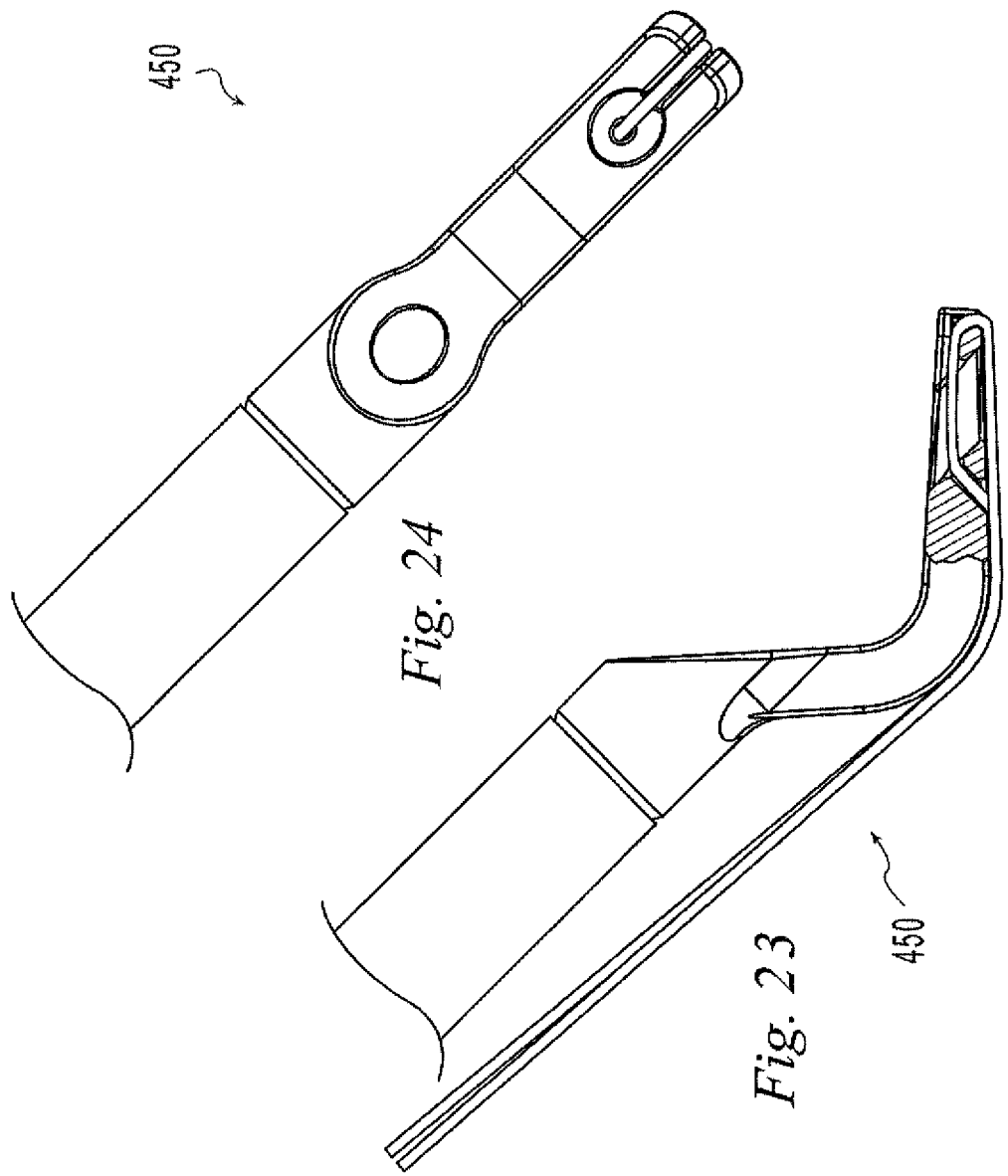

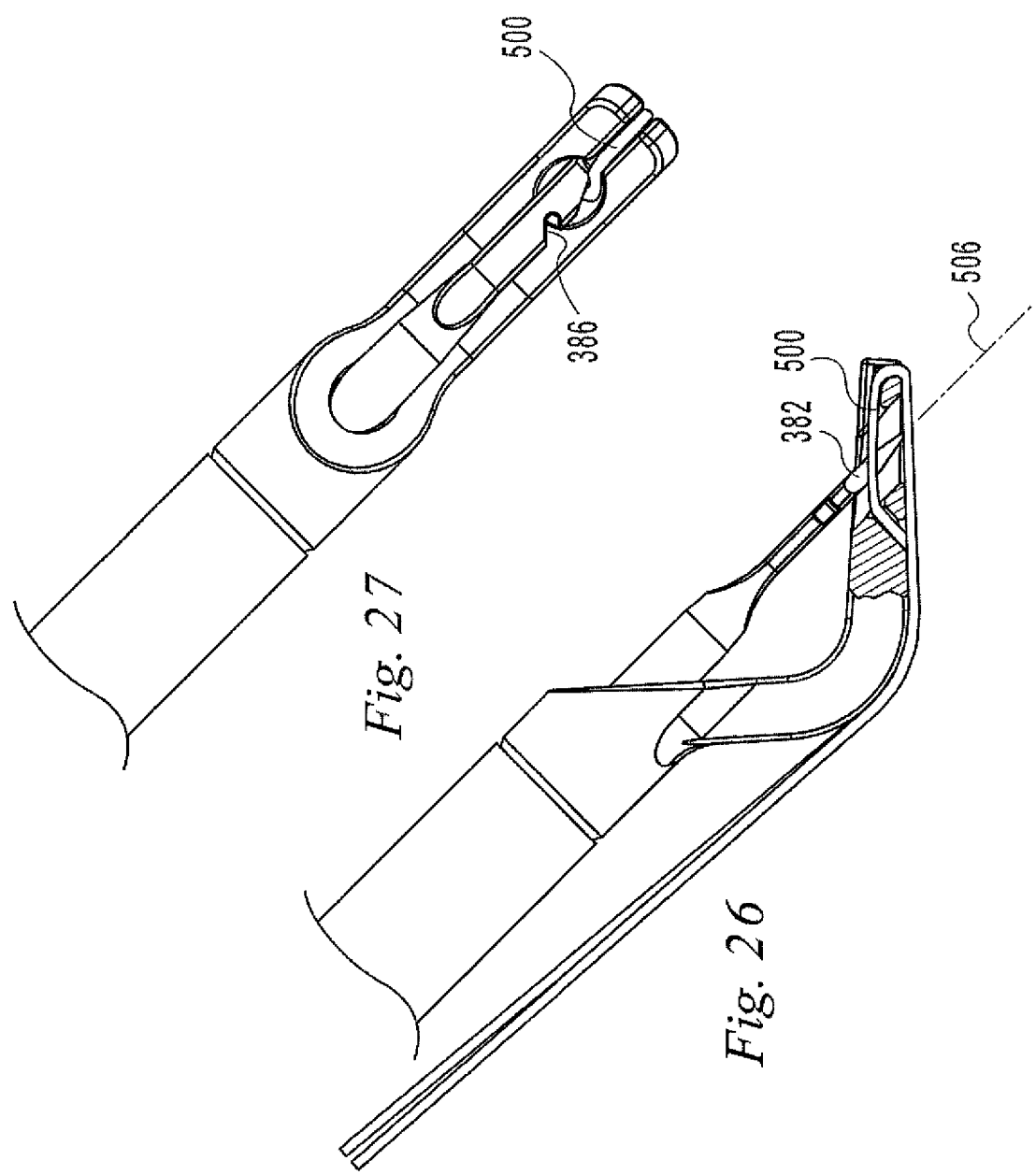

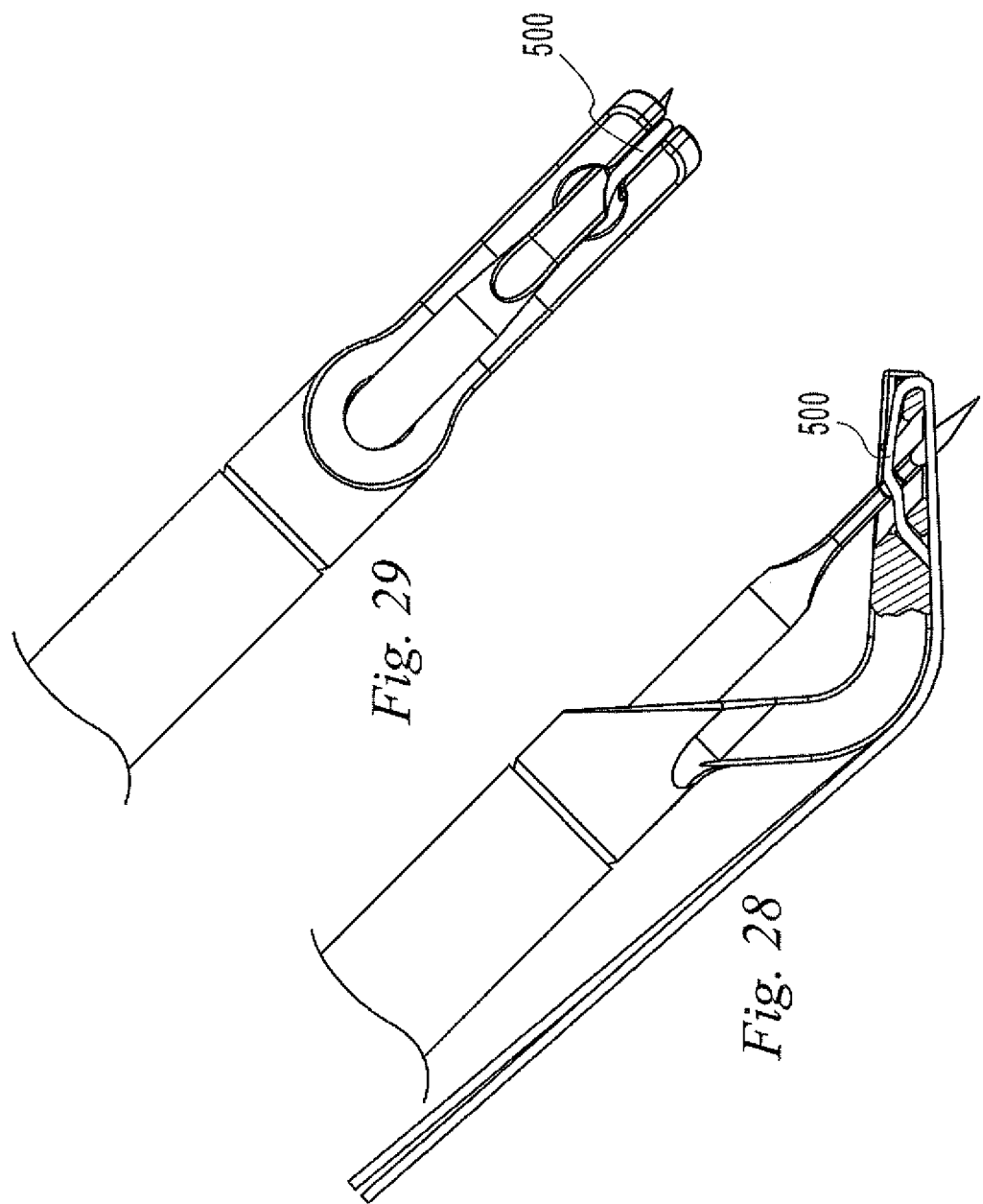

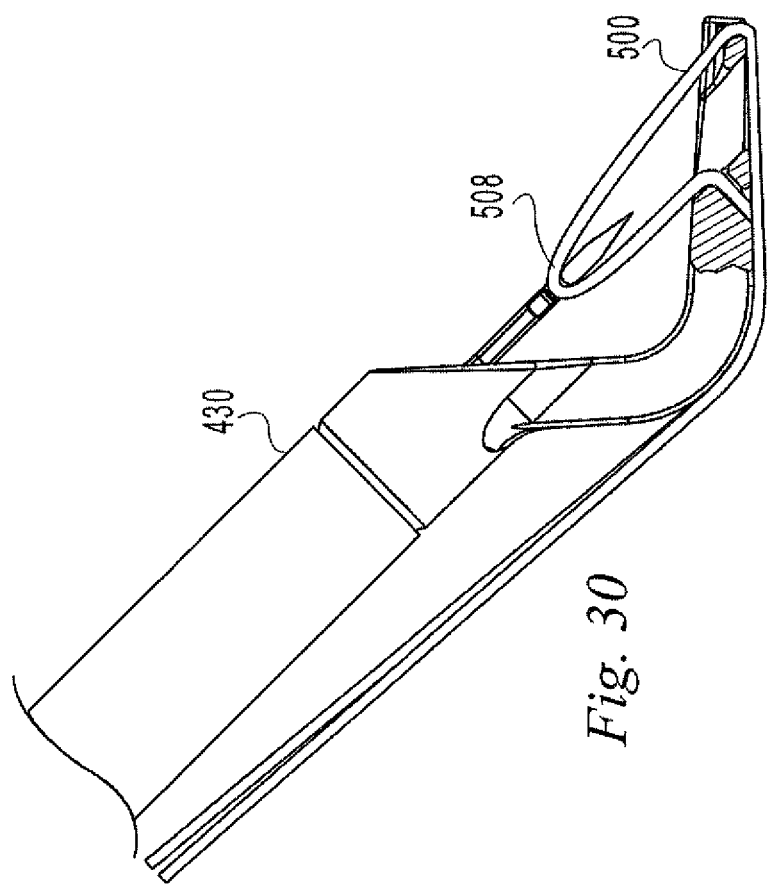

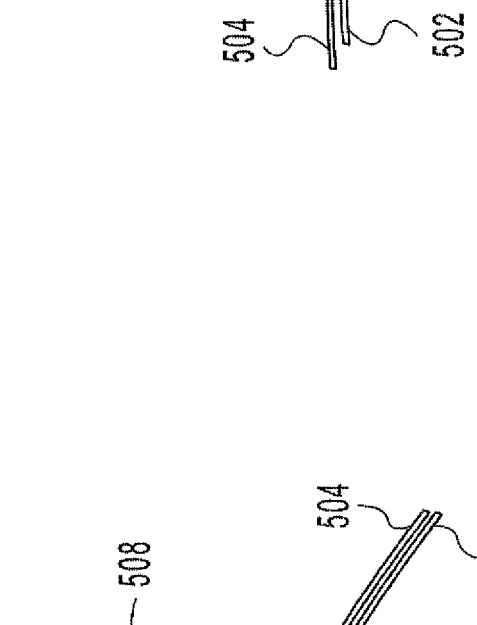
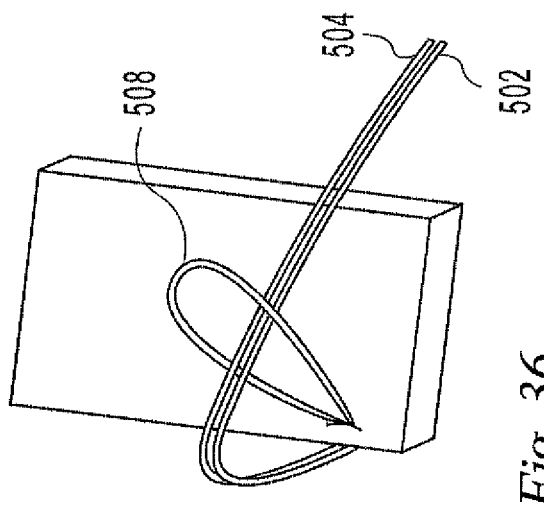
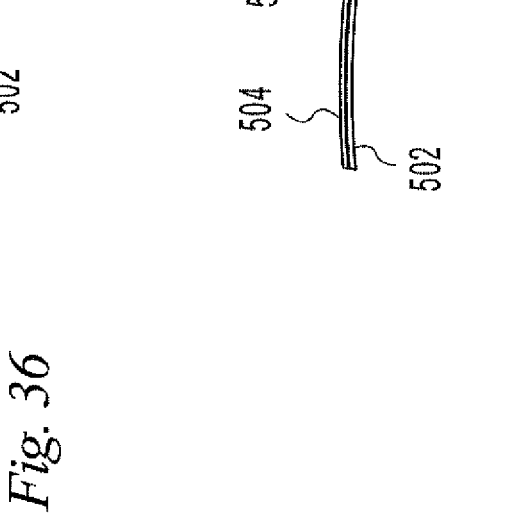
Fig. 36
Fig. 37
Fig. 38

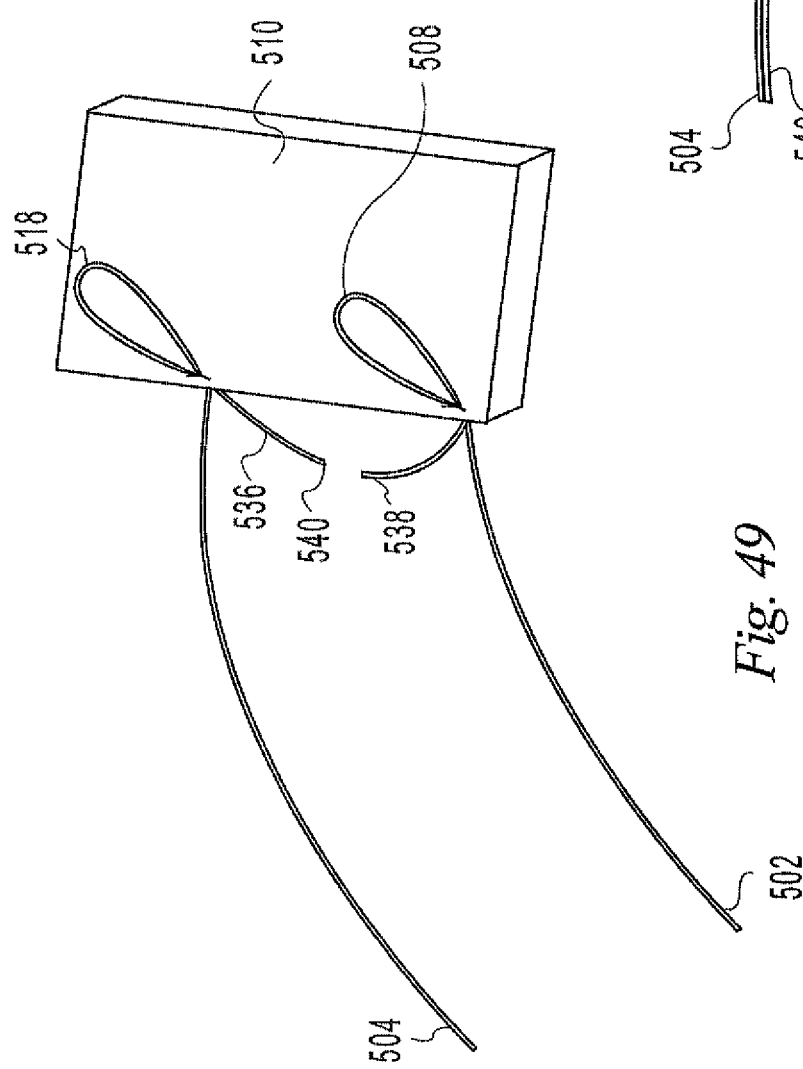
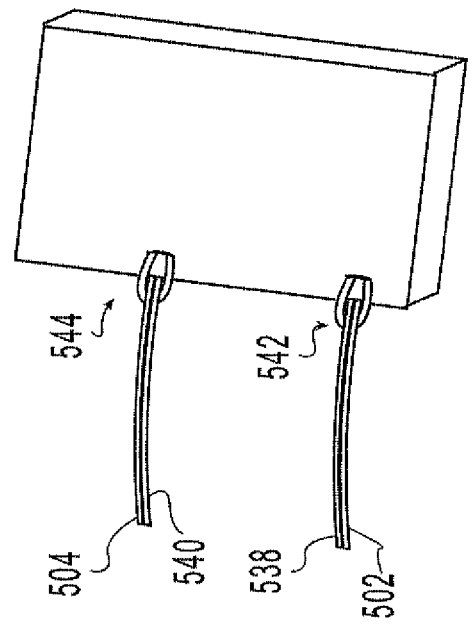
Fig. 49
Fig. 50

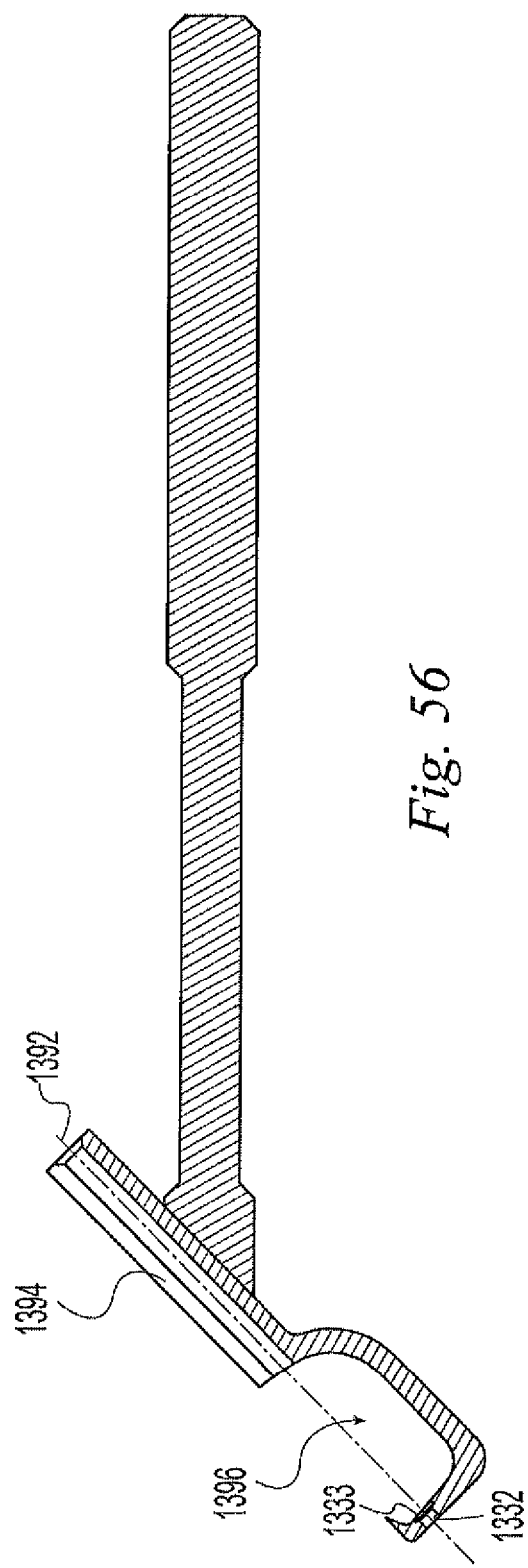

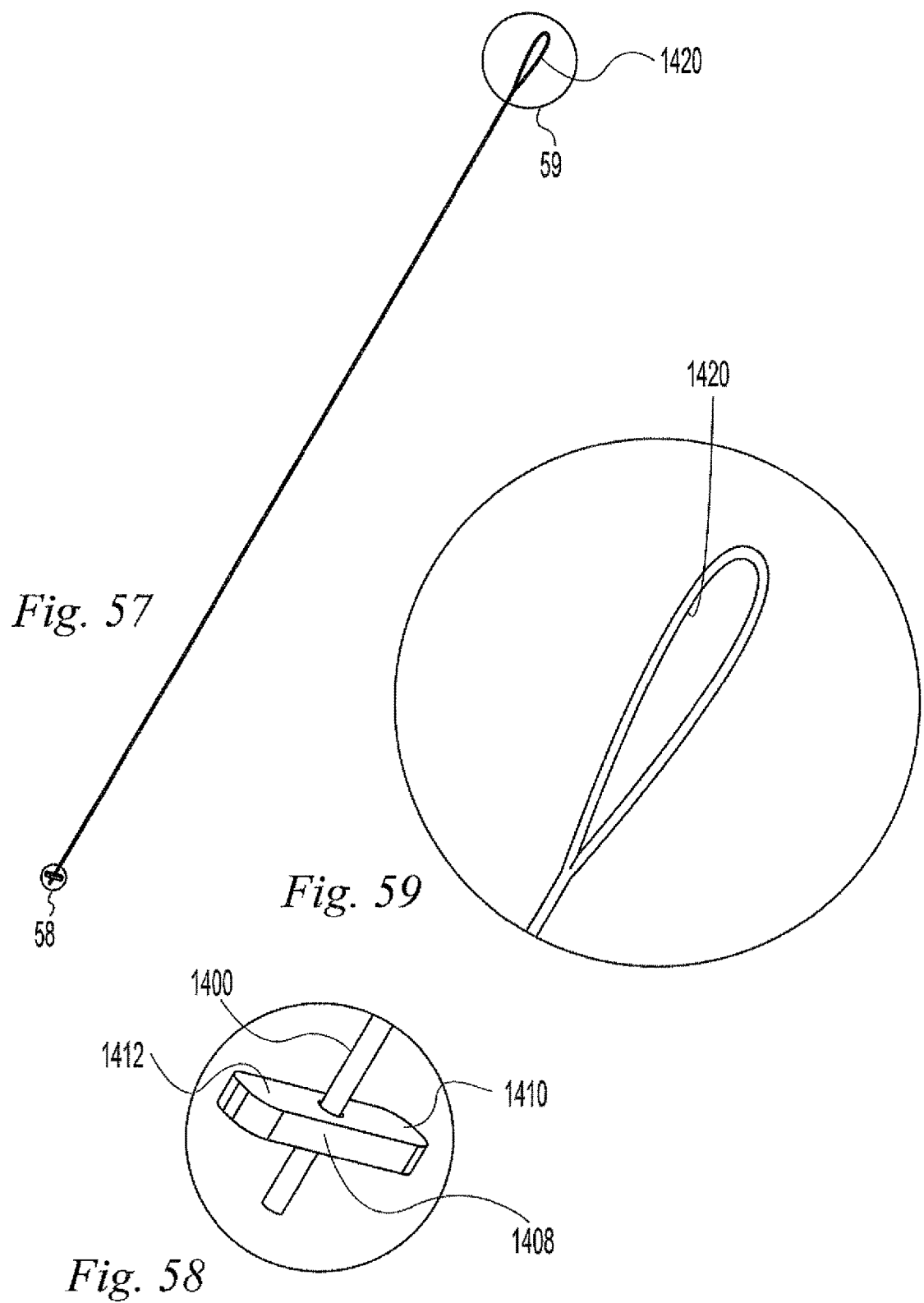

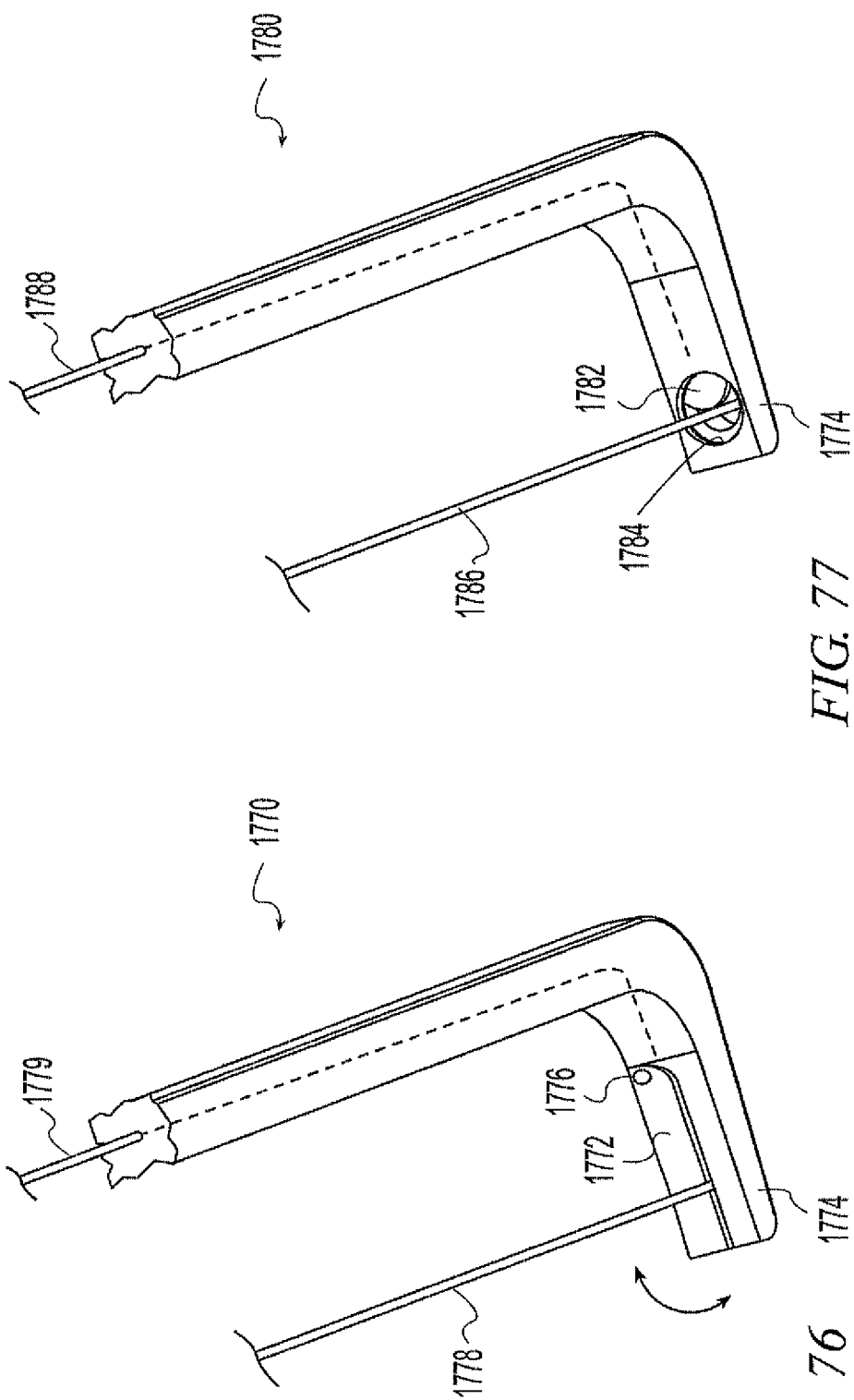

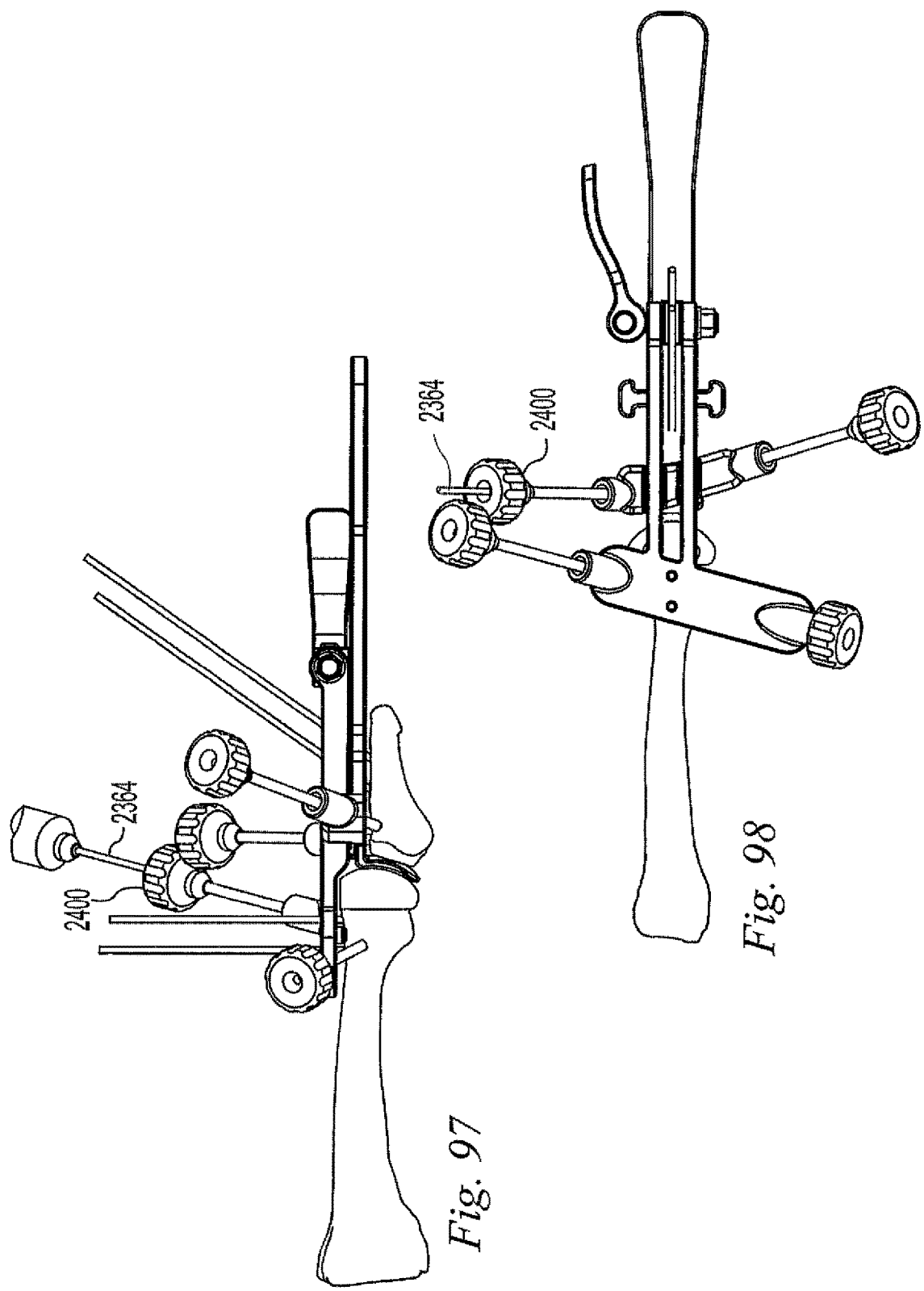

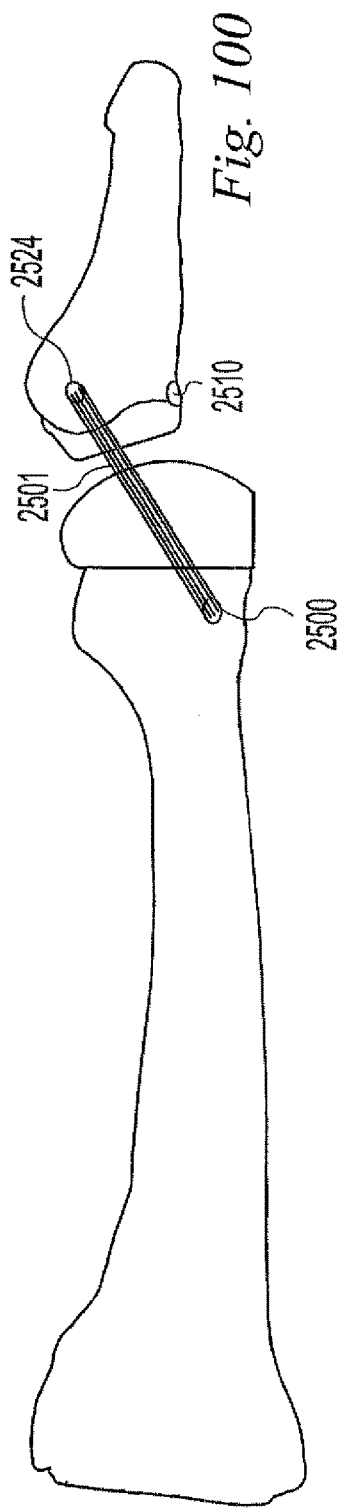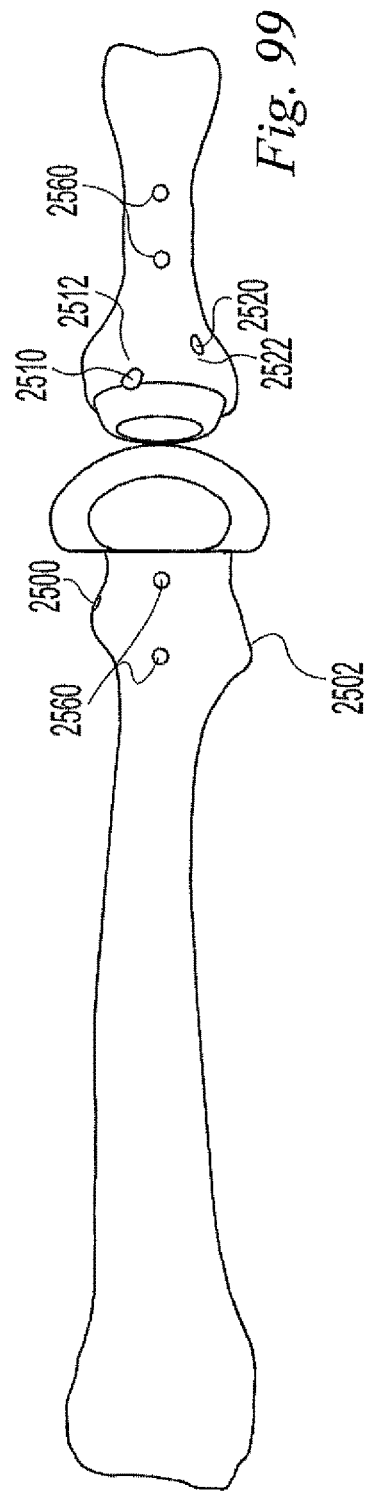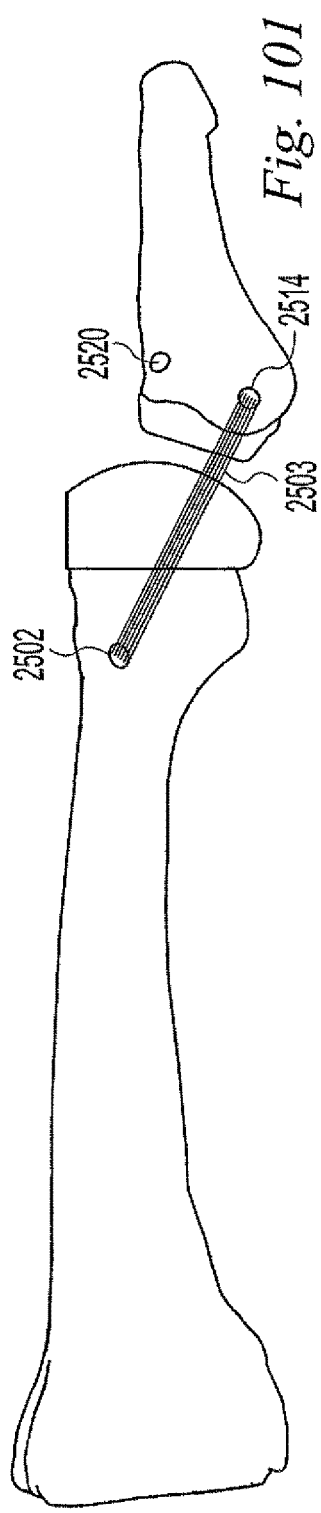

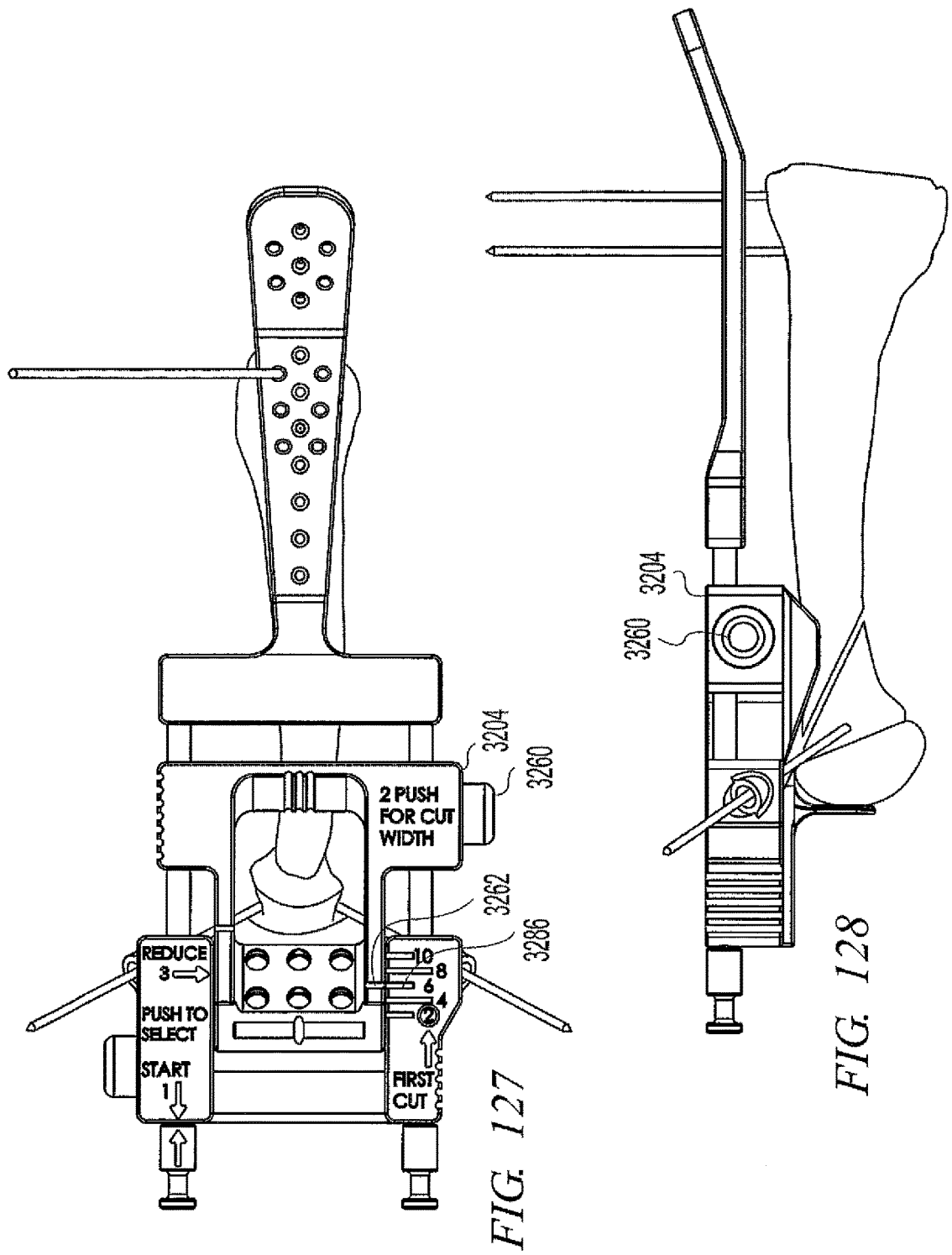

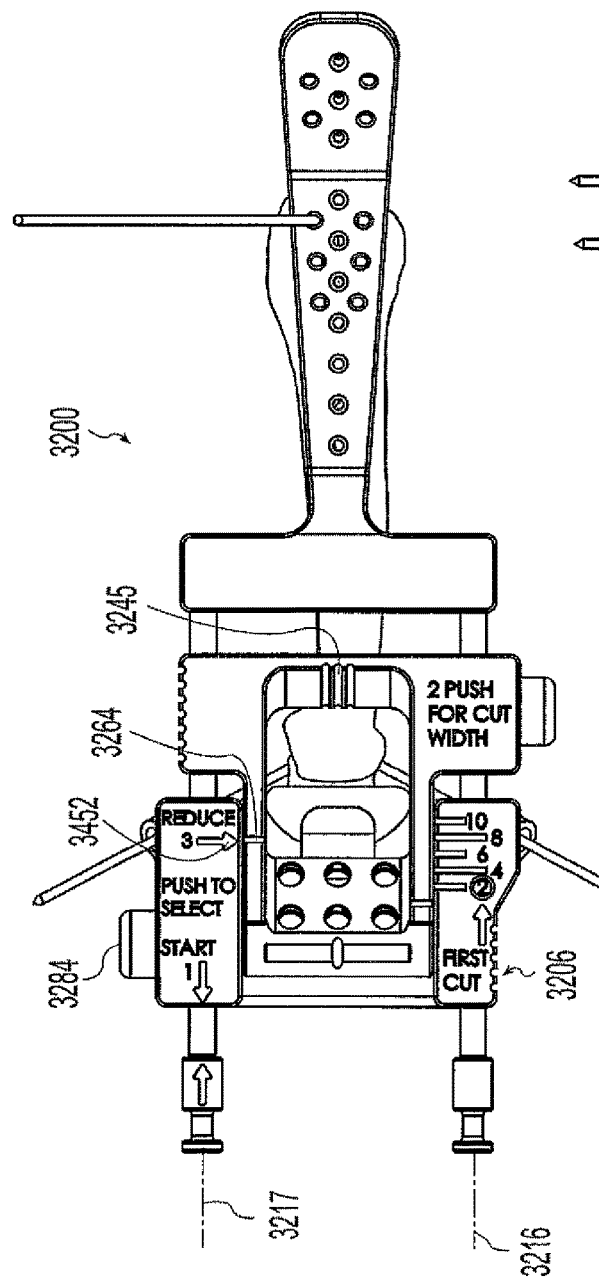
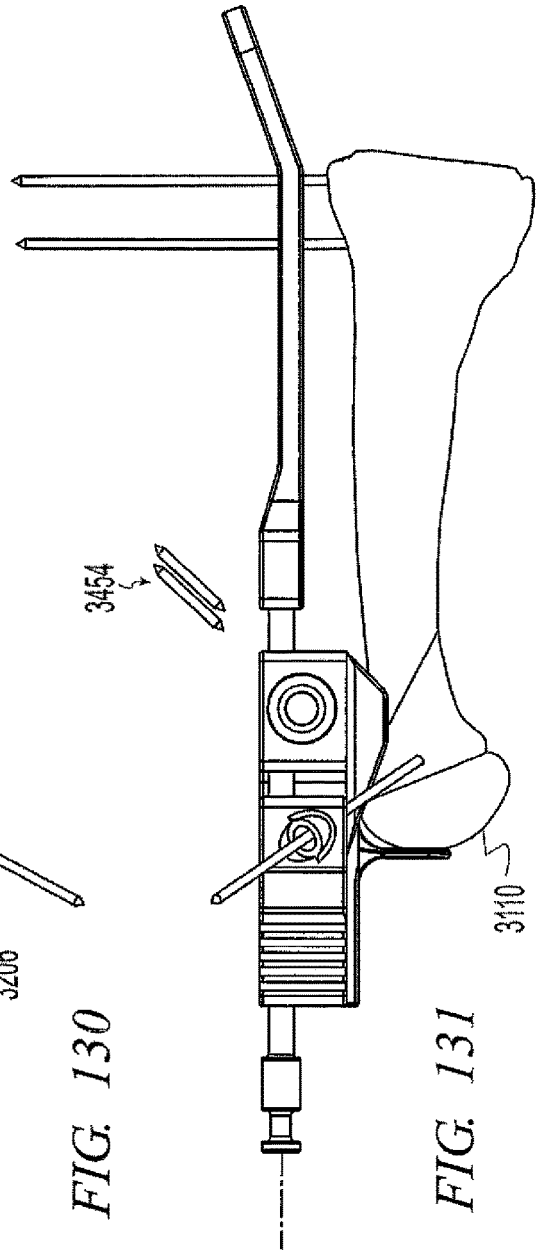
FIG. 130
FIG. 131

OSTEOTOMY GUIDE AND METHOD

CROSS-REFERENCE TO RELATED APPLICATIONS

This application is a United States National Phase filing of International Application No. PCT/US2012/045584 filed on Jul. 5, 2012 which claims priority to and the full benefit of U.S. Provisional Application Ser. No. 61/505,992, filed Jul. 8, 2011, U.S. Provisional Application No. 61/506,000, filed Jul. 8, 2011, U.S. Provisional Application No. 61/506,004, filed Jul. 8, 2011, U.S. Provisional Application No. 61/568,137, filed Dec. 7, 2011, U.S. Non-Provisional application Ser. No. 13/527,359, filed Jun. 19, 2012, U.S. Non-Provisional application Ser. No. 13/527,424, filed Jun. 19, 2012, U.S. Non-Provisional application Ser. No. 13/527,648, filed Jun. 20, 2012, and U.S. Non-Provisional application Ser. No. 13/527,765, filed Jun. 20, 2012, all of which are herein incorporated by reference.

FIELD OF THE INVENTION

The invention relates to surgical instruments useful for performing surgery adjacent a joint such as for example of the foot or hand.

BACKGROUND

Various surgical instruments are used in surgical interventions for conditions affecting a patient. Such instruments include suture passers, drill guides, and saw guides. Such instruments may be used to repair incisions and tears; pass grafts; attach grafts; anchor implants; cut bone; form holes for receiving soft tissue, grafts, sutures, pins, and screws; change the length or orientation of a bone; provide greater access to a surgical site; and for a variety of other purposes.

SUMMARY

Improved surgical instruments are provided including improved suture passers, improved drill guides for forming holes in bones adjacent a joint at locations referenced to the joint anatomy, and improved osteotomy guides.

In one aspect of the invention a suture passer includes a housing defining a linear motion axis extending proximally to distally and a needle mounted for translation along the motion axis between a first proximal position and a second distal position. The suture passer may include a foot mounted to the housing and having an opening in a proximal facing surface to receive the needle in the second position.

In another aspect of the invention a suture passer includes a housing, a needle, and a foot and the foot includes a passage from a distal facing surface to an exit adjacent a needle receiving opening. A groove may be formed in a proximally facing surface adjacent the passage and a notch may be formed in the distal end of the foot adjacent the groove such that the passage, groove and notch are able to receive a suture through the distal portion, across the needle receiving opening, along the proximally facing surface, and around the distal end.

In another aspect of the invention, a suture passer includes a housing, a needle mounted for motion between a first position and a second position, and a foot. The foot may position a suture in the path of the needle. The needle may have a notch engageable with the suture in the second position and impart a proximally directed force on the suture as the needle moves toward the first position. The needle may have a shaft with a bevel engageable with the suture to deflect the suture away from the needle axis as the needle is moved toward the second position. The notch may have a width and a depth. The width and depth may be related to the diameter of the suture. The width and depth may be related to the compliance of the suture.

In another aspect of the invention, a method of passing a suture through a material includes positioning a distal portion of a foot of a suture passer behind the material, extending a needle through the material; and retracting the needle to retrieve a bight of suture from the distal portion proximally through the material. The method may include retrieving multiple, connected bights of suture through the material to form a running stitch.

In another aspect of the invention, a suture passer includes a suture retriever and a suture. The suture retriever includes a receiver operable to receive and retain the suture and the suture includes a portion receivable and retained by the receiver. The suture may be received and maintained by way of a stopper, adhesion, hook and loop engagement, wedging, grasping, or other suitable mechanism. For example, the receiver may include an opening and the suture may include a stopper insertable into the opening. The opening may include a hole, slot, groove, notch, or other opening. The opening may extend through a portion of the receiver to define a passage through the portion of the receiver. The stopper may include a hook, barb, pledget, knot, plug, toggle, or other stopper. The receiver may receive the stopper by resilient deformation of the stopper or receiver, by changing orientation of the stopper from a receivable orientation to a retention orientation, or by other reception mechanism. In another example, the retriever includes a movable first member mounted for movement relative to a second member and movable between a first position in which the suture is receivable between the members and a second position in which the suture is grasped by the members.

The portion of the suture receivable by the receiver may be an end of the suture, a bight of the suture, or any other portion of the suture.

In another aspect of the invention, a suture passer includes a suture retriever and a suture and the suture retriever further includes a guide for guiding the suture into engagement with the suture receiver.

In another aspect of the invention, a suture passer includes a suture retriever and a suture and the suture retriever further includes a guide for guiding a cutter to form an opening in material through which the suture is passed. The guide may include a notch, groove, eye, tube, slot, rail, or other suitable guiding member able to guide a cutter. The cutter may include a wire, drill, blade, or other suitable cutter. For example, the guide may include a tube able to receive a drill and guide it to intersect a receiver. The guide may also be able to receive the suture and guide it into engagement with the receiver. The suture passer may further include a suture inserter able to engage the suture and the guide and useable to move the suture into engagement with the receiver. For example, the suture may have insufficient columnar rigidity to allow it to be pushed into engagement with the retriever by itself. A suture inserter may be used to help advance the suture. A suture inserter may include rods, wires, tubes, or other suitable members.

In another aspect of the invention, a guide is registrable with the joint anatomy and has a guiding portion aligned to guide the formation of tunnels that intersect the anatomic insertions and/or origins of the soft tissues of the joint based on anthropometric data.

In another aspect of the invention, the guide includes one or more reference surfaces, edges, axes, or points that engage or are alignable relative to one or more anatomical landmarks of the joint. These landmarks relate to the kinematic operation of the joint. Anthropometric data may be utilized to locate a cutter guide so that it aligns with bone features related to the joint kinematics.

Bone cutters for forming holes may include drills, pins, punches, broaches, saws, and other bone cutters. Bone cutting may include drilling, punching, broaching, slotting, sawing, slicing, and other cutting operations.

Guide reference surfaces may be flat, convex, concave, cylindrical, spherical, or any other suitable shape to engage or align relative to a landmark.

Anatomic landmarks may include an articular joint surface, a bone axis, an intramedullary canal, a joint plane, a body plane, a bone shaft, a condyle, an epicondyle, a ligament attachment, or any other suitable landmark that can be related to a desired cutter path.

Bone features may include an articular joint surface, a bone axis, an intramedullary canal, a joint plane, a body plane, a bone shaft, a condyle, an epicondyle, a ligament attachment, or any other suitable bone feature that is desired to be targeted.

The guiding portion may include a planar surface, notch, groove, hole, tube, rail, slot or other guiding portion able to guide a cutter in predetermined known relationship to the guide.

The position and orientation of an object in three dimensional space may be described relative to six degrees of freedom relative to three dimensional coordinate axes including three translational and three rotational degrees of freedom.

For example, in a guide configured for a metatarsophalangeal joint of the human foot, a concave reference surface may be registered with the convex head of the metatarsus by engaging the concave reference surface with the convex metatarsal head. If the reference surface is spherical it will engage the spherical metatarsal head to reference the joint center of rotation and eliminate all three translational degrees of freedom. The three rotational degrees of freedom may be resolved with additional landmarks. For example, by aligning a guide handle axis parallel to the axis of the metatarsus two degrees of rotational freedom are eliminated. The final degree of rotational freedom may be resolved, for example by aligning a guide surface, such as the guide handle top surface, parallel to the transverse plane.

In another example, the concave reference surface may be cylindrical. When it is engaged with the metatarsal head it will resolve two degrees of translational freedom. The third translational degree of freedom may be eliminated by aligning a center plane of the guide with the axis of the metatarsus. The rotational degrees of freedom may be eliminated as described above.

In another example, a convex reference surface may be registered to a concave landmark. For example, a convex reference surface may be registered with the articular surface of the proximal phalanx at the MTP joint.

There are many ways that the guide may be registered to a landmark. However, the guide may be designed using anthropometric data so that when it is registered relative to all six degrees of freedom, the guiding portion will guide a cutter to intersect a predetermined joint feature. For example, the guide may include a hole for guiding a drill to intersect the anatomic attachment of a ligament based on the guides relationship to anatomic landmarks. With the guide registered to multiple landmarks to fix its orientation relative to the surgical site in three dimensions, it is possible to target multiple bone features simultaneously.

In another aspect of the invention, a guide provides a stable base with a cutter guide operable to guide a cutter to separate the bone into two, relatively moveable portions.

In another aspect of the invention, a guide includes a cutter guide operable to guide a cutter to form two parallel cuts transverse to the bone axis to remove a predetermined portion of the bone.

In another aspect of the invention, a guide provides a reduction mechanism operable to reduce a gap between two bone portions with motion along a predefined path. For example, a guide may be provided with a mechanism to reduce an osteotomy along the axis of the bone. This advantageously preserves joint mechanics of a joint including the cut bone by maintaining the instantaneous axis of rotation in the same position relative to the bone axis. In another example, a guide may be provided with a mechanism to move portions of a bone linearly at an angle transverse to the bone axis. In another example a guide may be provided with a mechanism to move portions of a bone along a non-linear path.

In another aspect of the invention, a guide may include references such as one or more reference surfaces, edges, axes, or points that engage or are alignable relative to one or more anatomical landmarks of the bone to position a cutter guide and/or a reduction mechanism in a predetermined relationship relative to the bone. For example, the cutter guide may be oriented relative to the one or more reference surfaces to guide a cutter to cut the bone so that the cut surfaces are oriented relative to the dominate loads on the bone to promote healing. For example, the cutter guide may cut the bones so that the cut bone surfaces are normal to the typical load on the bone to reduce shear forces that may interfere with healing of the osteotomy. In another example, the reduction mechanism may be oriented relative to the one or more reference surfaces to guide reduction of the bone portions along a mechanical axis of the bone so that the healed osteotomy will result in the same kinematic relationships within an associated joint.

In another aspect of the invention, a guide may include a fixation mechanism to attach the guide to the bone in a predetermined relationship. The guide may include a cutter guide portion operable to guide a cutter to separate the bone into two relatively moveable portions and the fixation mechanism may capture the two bone portions so that their relative positions are maintained according to a predetermined relationship. The guide may include a reduction mechanism operable to guide the two bone portions along a predefined axis as they are brought together to be joined. For example, the guide may include a first stage and a second stage joined together in linear translating relationship along a single translational degree of freedom. The stages may be fixed to a bone. The guide may guide a cutter to separate the bone into two relatively moveable portions with one portion being attached to each of the first and second stages. The stages may then be operable to move along the single translational degree of freedom to move the bone portions together so that the cut surfaces of the bone portions abut one another. One or more fasteners may then be used to attach the bone portions to one another.

In another aspect of the invention, a guide includes a base member, a first stage mounted to the base member in relative translating relationship, and a second stage mounted to the base member in relative translating relationship independent of the first stage. The base member may include a fixation mechanism operable to attach the base member to a first portion of an underlying bone. The second stage may include a fixation mechanism operable to attach the second stage to a second portion of the underlying bone. The first stage may include a cutter guide operable to guide a cutter to cut the bone. The first stage may be moved between different translated positions to guide the cutter to make spaced apart parallel cuts into the bone to remove a predetermined amount of bone between the first and second portions of the bone with parallel cut surfaces. The second stage may then be translated relative to the base to move the second portion of bone into contact with the first portion of bone.

In another aspect of the invention, the guide may include a fastener guiding portion operable to guide placement of the one or more fasteners in a predetermined orientation relative to the cut surfaces of the bone. For example, a fastener guide may be operable to place the one or more fasteners normal to the cut surfaces.

In another aspect of the invention, a guide may be configured to cut a metatarsal bone of a metatarsophalangeal joint of the human foot. The guide may include a planar reference surface engageable with the articular surface of the metatarsus to eliminate one translational degree of freedom. The guide may include a second planar reference surface engageable with the dorsal aspect of the metatarsal head or another portion of the dorsal surface of the metatarsus to eliminate another translational degree of freedom. The guide may include a center plane alignable with the axis of the metatarsus to eliminate a third translational degree of freedom and one rotational degree of freedom. Positioning the second planar surface parallel to the transverse body plane or the dorsal surface of the foot eliminates the remaining two rotational degrees of freedom. The guide may include first and second stages mounted to a base member in translating relationship along a reduction axis constraining the stages to a single translational degree of freedom. The base member and second stage may each receive one or more fasteners operable to join each in fixed relationship to an underlying portion of the metatarsus. For example, the base and second stage may each have at least two angled holes operable to receive pins that are driven into the bone. The angled pins constrain each portion of the metatarsus in six degrees of freedom relative to the base and second stage. A cutter guide mounted to the first stage may be operable to guide a cutter to cut the metatarsus parallel to the plantar surface of the foot when the patient is standing to promote healing of the osteotomy. The first stage may be repositionable relative to the underlying bone to guide multiple parallel cuts to remove a predetermined amount of bone. The second stage may then be moved relative to the base member to reduce the osteotomy along the mechanical axis of the metatarsus. When the bones abut, a fastener guide may be used to guide a fastener into the bone to fix the bone portions together. The constrained reduction maintains the relationship of the metatarsal head relative to the mechanical axis of the metatarsus to preserve the joint kinematics.

A fixation mechanism may include one or more pins, screws, straps, and other suitable fixation mechanisms.

Guide reference surfaces may be flat, convex, concave, cylindrical, spherical, or any other suitable shape to engage or align relative to a landmark.

Anatomic landmarks may include one or more articular joint surfaces, bone axes, intramedullary canals, joint planes, body planes, bone shafts, condyles, epicondyles, ligament attachments, or any other suitable landmark.

A cutter guide portion may include one or more planar surfaces, notches, grooves, holes, tubes, slots or other guiding portion able to guide a cutter in predetermined known relationship to the guide.

A cutter for forming an osteotomy may include an oscillating saw, a reciprocating saw, a rotary saw, a band saw, an end mill, an osteotome, a water jet, or any other suitable cutter.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 2 is a dorsal view of the metatarsus and phalanx of the right second metatarsophalangeal joint of the human foot;

FIG. 3 is a medial view of the bones of FIG. 2;

FIG. 4 is a lateral view of the bones of FIG. 2;

FIG. 10 is a side elevation view of the suture passer of FIG. 5;

FIG. 11 is a top plan view of the suture passer of FIG. 5;

FIG. 15 is a bottom plan view of a component of the suture passer of FIG. 5;

FIG. 16 is a side elevation view of the component of FIG. 15;

FIG. 17 is a sectional view taken along line 17-17 of FIG. 16;

FIG. 19 is a partially sectioned side elevation view of the distal end of the suture passer of FIG. 5 illustrating a suture being loaded on the suture passer;

FIG. 20 is a top plan view of the distal end of the suture passer of FIG. 5 illustrating a suture being loaded on the suture passer;

FIG. 21 is a partially sectioned side elevation view of the distal end of the suture passer of FIG. 5 illustrating a suture being loaded on the suture passer;

FIG. 22 is a top plan view of the distal end of the suture passer of FIG. 5 illustrating a suture being loaded on the suture passer;

FIG. 23 is a partially sectioned side elevation view of the distal end of the suture passer of FIG. 5 illustrating a suture being loaded on the suture passer;

FIG. 24 is a top plan view of the distal end of the suture passer of FIG. 5 illustrating a suture being loaded on the suture passer;

FIG. 26 is a partially sectioned side elevation view of the distal end of the suture passer of FIG. 5 illustrating the operation of the suture passer;

FIG. 27 is a top plan view of the distal end of the suture passer of FIG. 5 illustrating the operation of the suture passer;

FIG. 28 is a partially sectioned side elevation view of the distal end of the suture passer of FIG. 5 illustrating the operation of the suture passer;

FIG. 29 is a top plan view of the distal end of the suture passer of FIG. 5 illustrating the operation of the suture passer;

FIG. 30 is a partially sectioned side elevation view of the distal end of the suture passer of FIG. 5 illustrating the operation of the suture passer;

FIGS. 32-50 are perspective views illustrating the suture passer of FIG. 5 in use to pass sutures through a material to create a variety of stitches.

FIG. 56 is a sectional view taken along line 56-56 of FIG. 54;

FIG. 57 is a perspective view of a component of the suture passer of FIG. 52;

FIG. 58 is an enlarged perspective view of the distal end of the component of FIG. 58;

FIG. 59 is an enlarged perspective view of the proximal end of the component of FIG. 58;

FIG. 76 is a perspective view of an alternative receiver useable with the suture passers of FIG. 51 and FIG. 52; and FIG. 77 is a perspective view of an alternative receiver useable with the suture passers of FIG. 51 and FIG. 52.

FIG. 97 is a side elevation view of the guide of FIG. 78 in use with an MTP joint;

FIG. 98 is a top plan view of the guide of FIG. 78 in use with an MTP joint;

FIG. 99 is a dorsal view of the metatarsus and phalanx of the right second metatarsophalangeal joint of the human foot showing tunnels formed utilizing the guide of FIG. 78;

FIG. 100 is a medial view of the bones of FIG. 26;

FIG. 101 is a lateral view of the bones of FIG. 26; and

FIG. 127 is a top plan view of the guide of FIG. 103 showing a position of the guide on a metatarsus;

FIG. 128 is a side elevation view of the guide of FIG. 103 showing the position of FIG. 127;

FIG. 130 is a top plan view of the guide of FIG. 103 showing the guide in use to reduce an osteotomy on a metatarsus;

FIG. 131 is a side elevation view of the guide of FIG. 103 showing the position of FIG. 30 and a pins being inserted to secure the osteotomy;

DESCRIPTION OF THE ILLUSTRATIVE EXAMPLES

The following illustrative examples illustrate instruments and techniques for treating skeletal joints. Instruments and techniques according to the present invention may be used in conjunction with any skeletal joint but the illustrative examples are shown in a size and form most suitable for the joints of the hand and foot. In particular, the illustrative examples depict their use on metatarsophalangeal (MTP) joints of the human foot. The illustrative instruments and techniques are also suitable for use on metacarpophalangeal (MCP) joints of the human hand.

Figure 1:
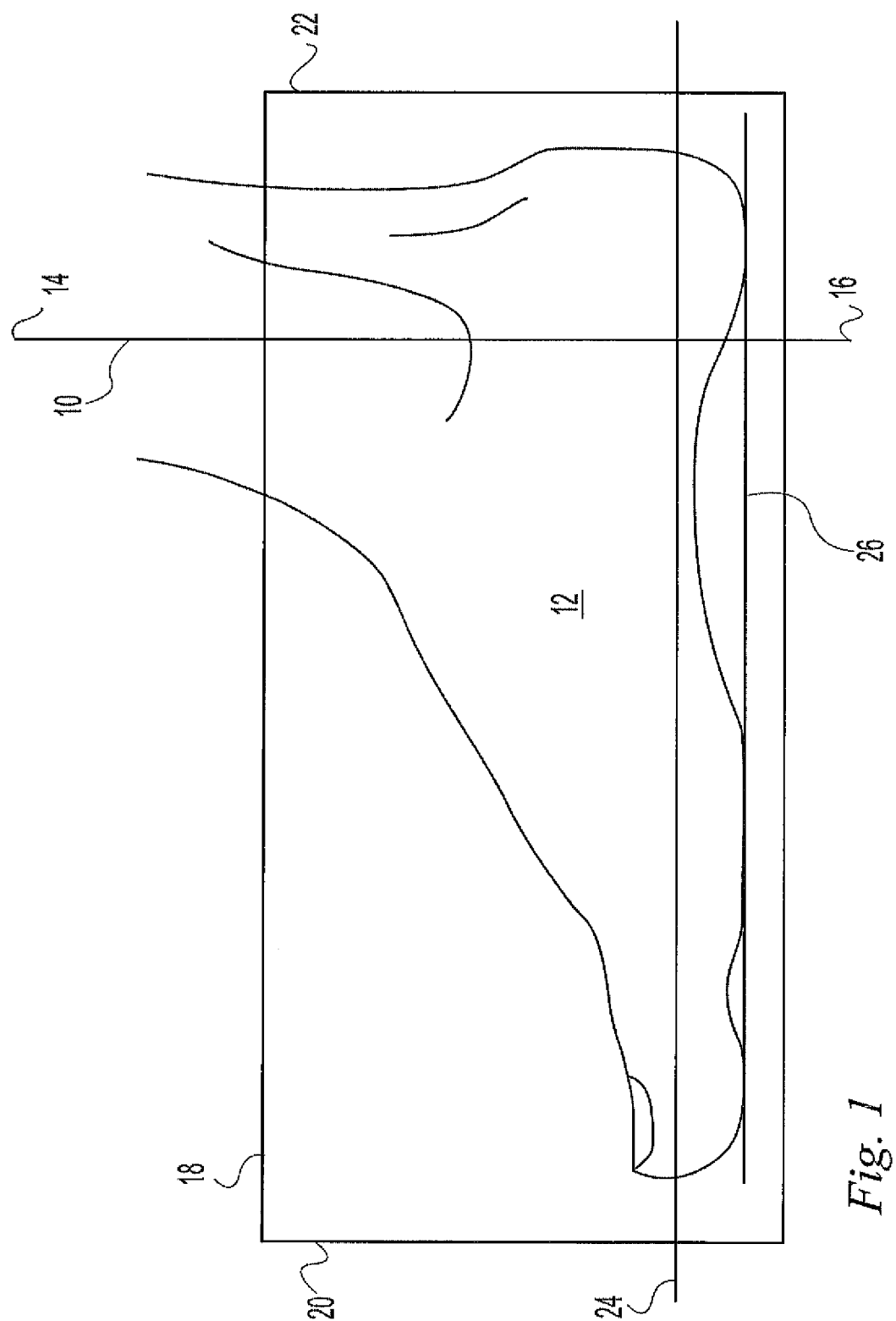
FIG. 1 is side elevation view of the human foot illustrating anatomic reference planes.
Figure 5:
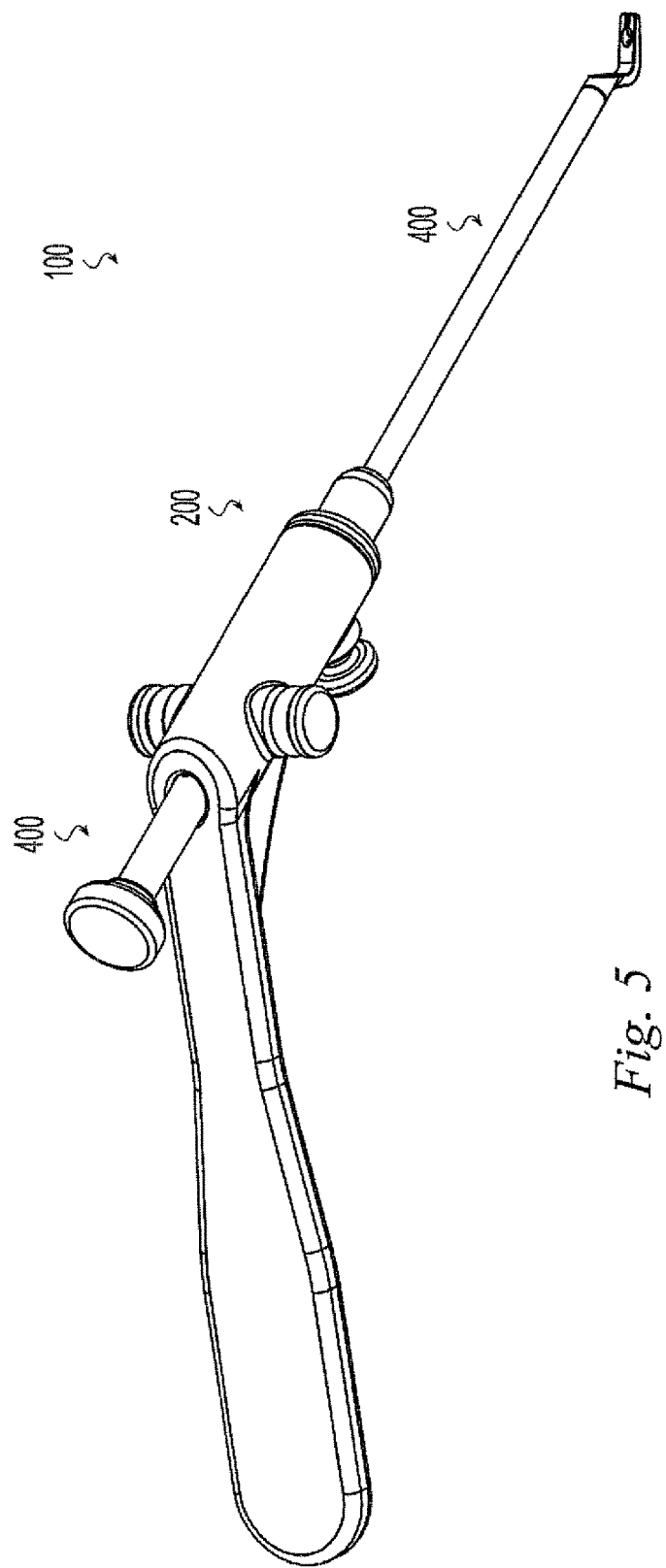
FIG. 5 is a perspective view of an illustrative example of a suture passer according to the present invention.
Figure 6:
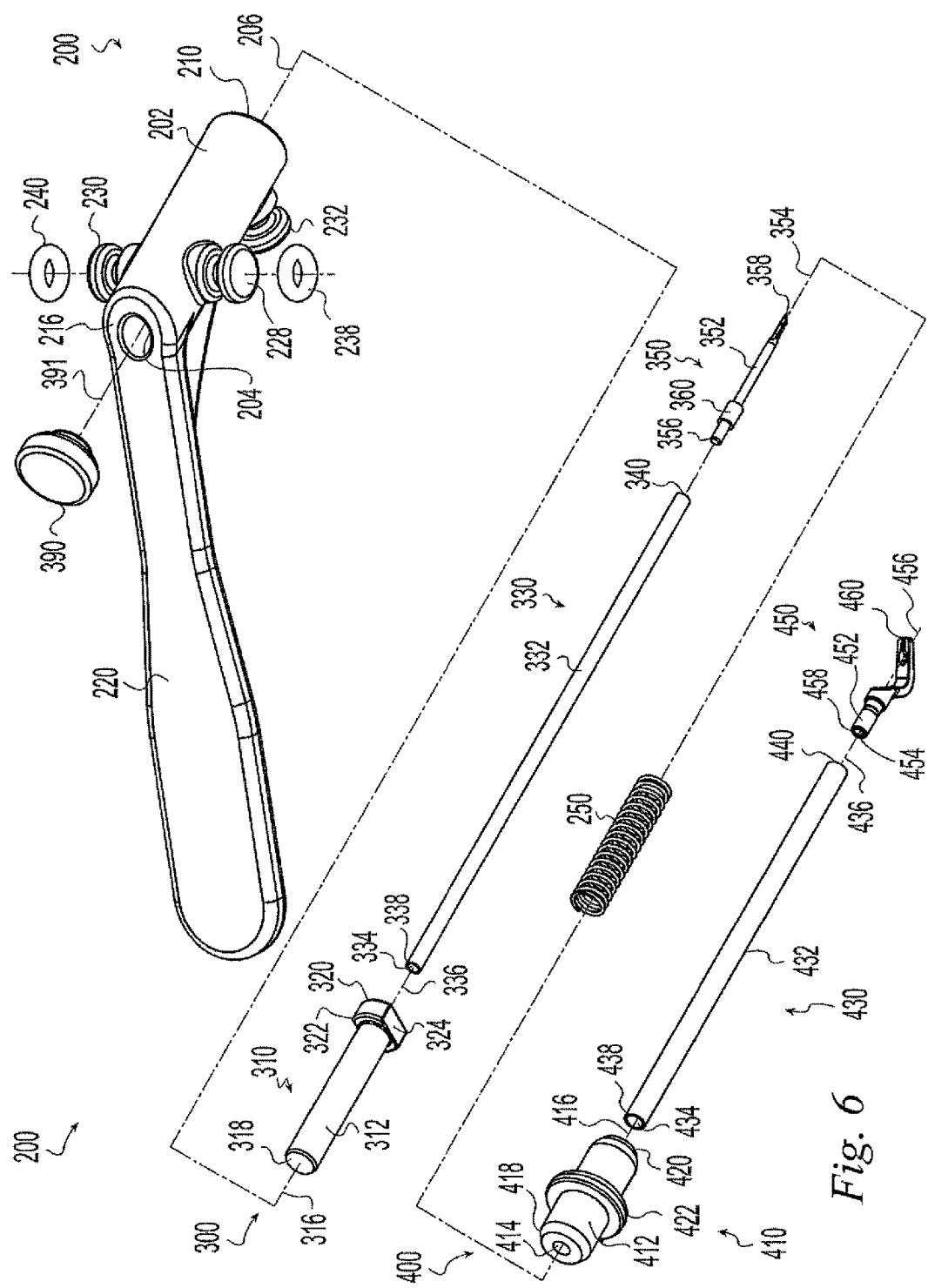
FIG. 6 is an exploded perspective view of the suture passer of FIG. 5.
Figure 8:
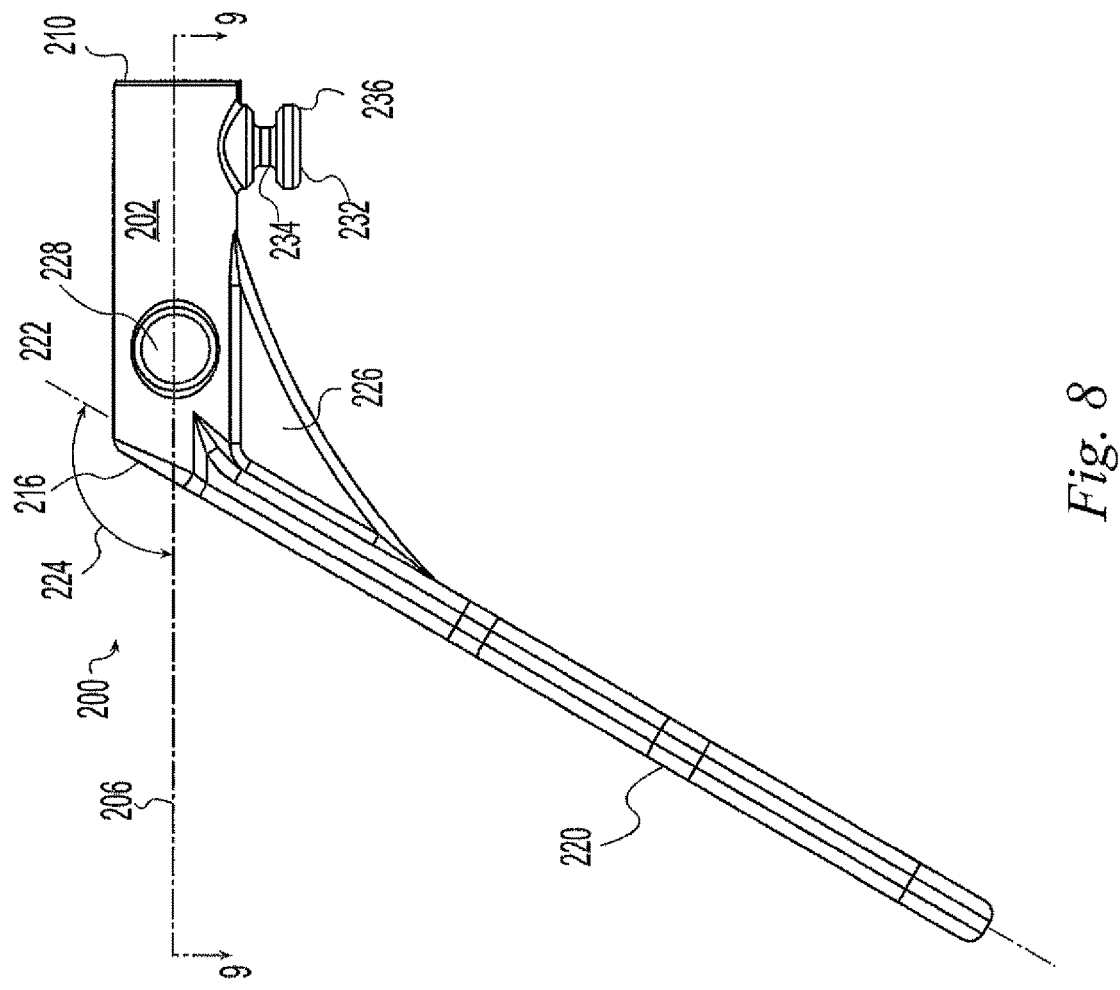
FIG. 8 is a is a side elevation view of the component of FIG. 7.
Figure 7:
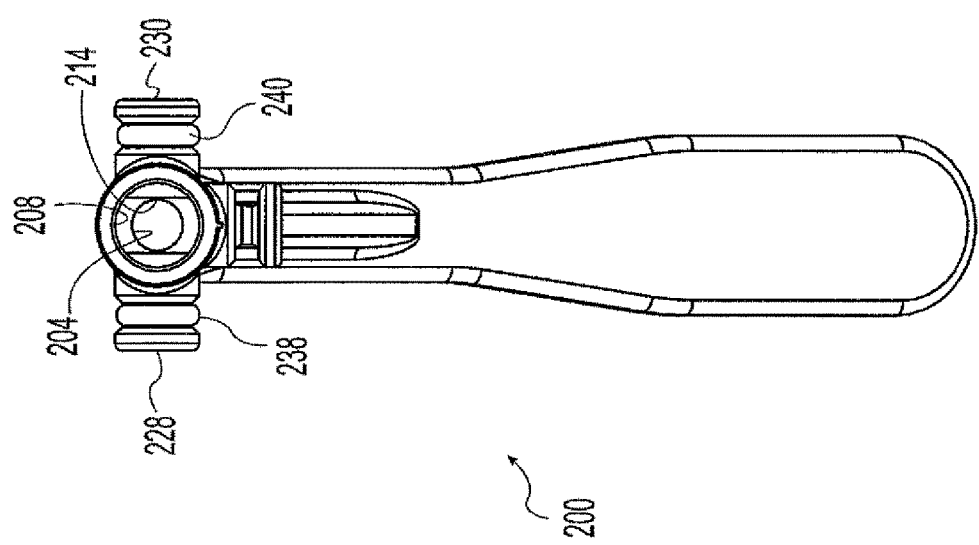
FIG. 7 is a front elevation view of a component of the suture passer of FIG. 5.
Figure 9:
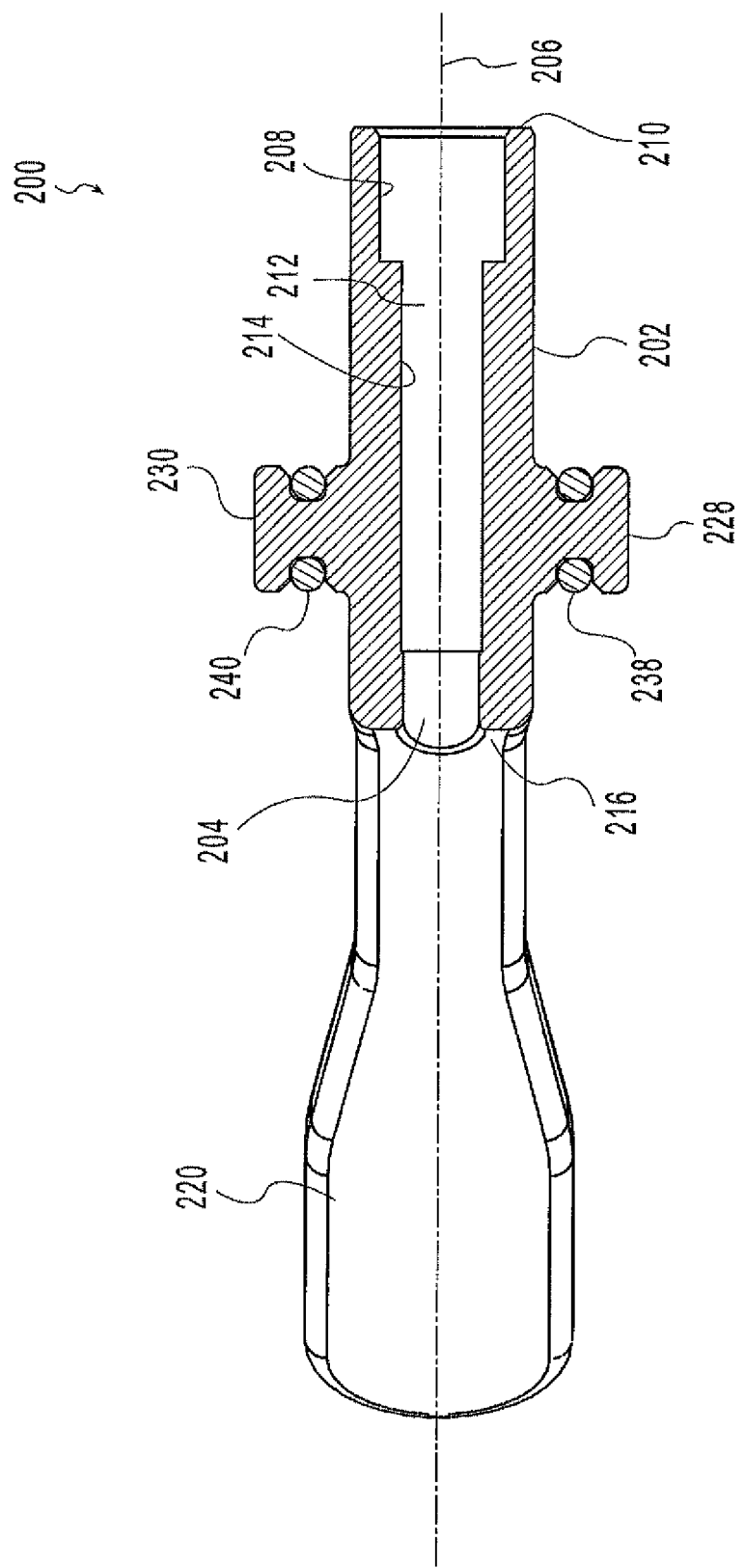
FIG. 9 is a sectional view taken along line 9-9 of FIG. 8.
Figure 12:
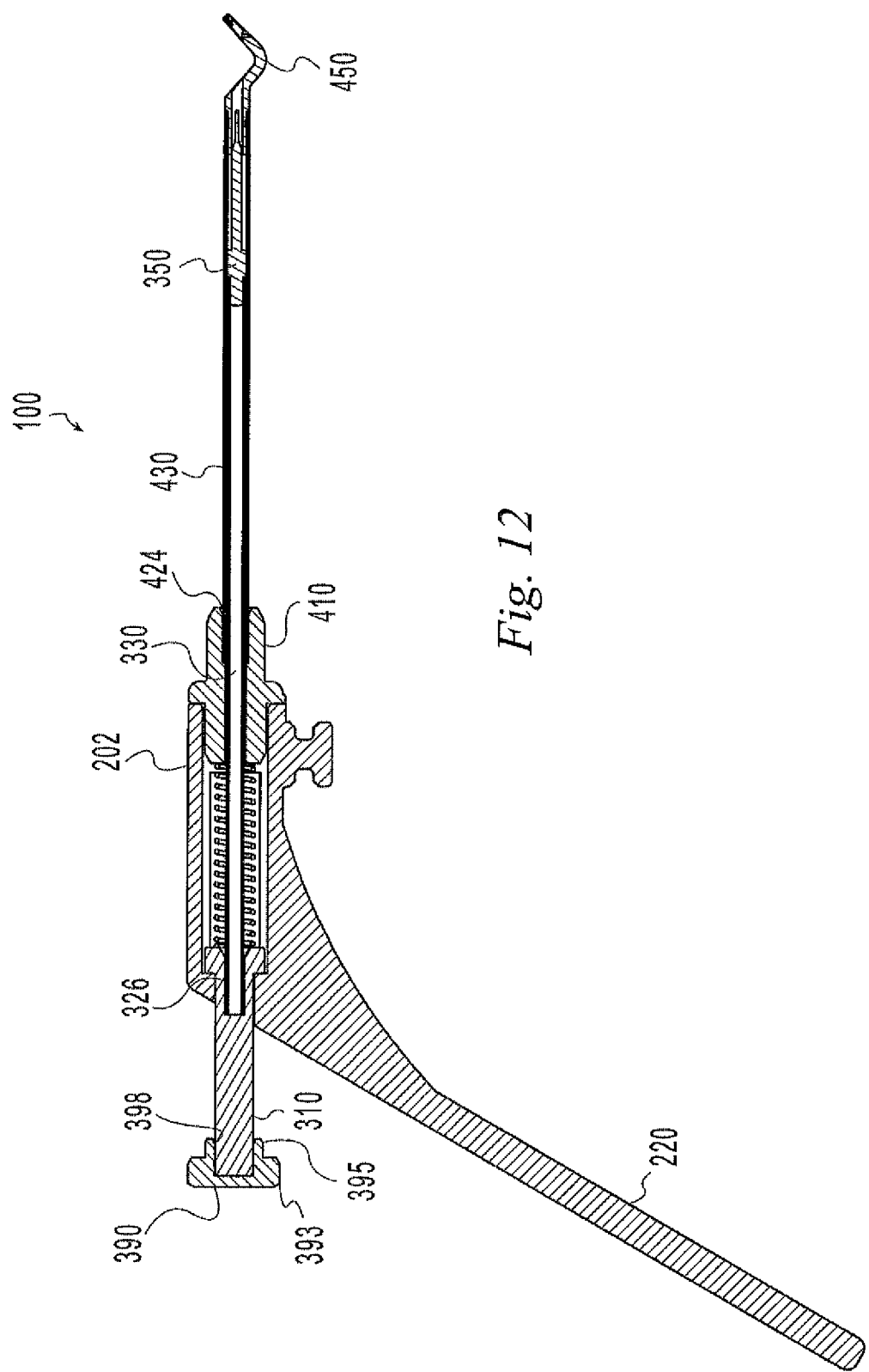
FIG. 12 is a sectional view taken along line 12-12 of FIG. 11.

FIG. 1 illustrates the anatomic planes of the foot that are used for reference in this application. The coronal plane 10 extends from the medial aspect 12 to the lateral aspect of the foot and from dorsal 14 to plantar 16 and divides the foot between the toes and heel. The sagittal plane 18 extends anterior 20 to posterior 22 and dorsal 14 to plantar 16 and divides the foot into medial and lateral halves. The transverse plane 24 extends anterior 20 to posterior 22 and medial to lateral parallel to the floor 26.

FIGS. 2-4 illustrate the metatarsus 30 and proximal phalanx 50 of the second MTP joint of the right foot. The medial and lateral epicondyles 32, 34, located on the medial-dorsal and lateral-dorsal aspects of the metatarsus 30 respectively, are the origins of the medial and lateral proper collateral ligaments (PCLs) 36, 38 and the medial and lateral accessory collateral ligaments (ACLs) 40, 42 of the MTP joint. The medial PCL inserts at the medial-plantar aspect 52 and the lateral PCL inserts at the lateral-plantar aspect 54 of the proximal phalanx 50. The ACLs fan out and insert into the plantar plate 44. The metatarsus includes a metatarsal head 46 having an articular surface 48 and the proximal phalanx includes a phalangeal head 56 having an articular surface 58. The metatarsus 30 further includes a longitudinal axis 60 extending lengthwise down the center of the bone.

The terms "suture" and "suture strand" are used herein to mean any strand or flexible member, natural or synthetic, able to be passed through material and useful in a surgical procedure. The term "material" is used herein to mean implants, grafts, fabric, tendon, ligament, fascia, skin, muscle, bone, and any other material it is desirable to cut or through which it is desirable to pass a suture. The term "transverse" is used herein to mean crossing as in non-parallel. The term "bight" is used herein to mean a bend or loop formed in the intermediate portion of a suture.

The illustrative examples of FIGS. 5-50 depict instruments and techniques to pass a suture through a material. The instruments and techniques may be used to pass a suture through any material, at surgical sites anywhere in a patient's body, and for any purpose. The instruments and techniques are particularly useful where access to confined spaces and the ability to pass a suture through difficult to penetrate materials are needed. For example, surgery on the hands and feet often involve working in confined spaces around small joints and tough connective tissues through which it may be desirable to pass a suture.

FIGS. 5-17 depict an illustrative example of a suture passer 100. The suture passer 100 includes a housing 200, a needle assembly 300, and a barrel assembly 400 mounted together and operable to translate the needle assembly 400 between a first, retracted position and a second, extended position to manipulate a suture strand.

The housing 200 includes a hollow receiver portion 202 having a hollow through bore 204 with a longitudinal bore axis 206. An enlarged counter bore 208 is formed coaxial with the through bore 204 at a distal end 210 of the receiver 202. An intermediate portion 212 of the through bore 204 has flat side walls 214. A handle 220 extends downwardly and proximally from the receiver 202 and has a longitudinal handle axis 222. The handle axis 222 forms an angle 224 with the bore axis 206. The angle 224 is in the range of 90 to 180 degrees; preferably 100 to 140 degrees; more preferably 110 to 130 degrees. In the illustrative example of FIGS. 5-17, the angle 224 is 120 degrees. A gusset 226 extends between the handle 220 and the receiver 202 for strength. One or more knobs extend from the housing to provide suture strand anchor or routing points. In the illustrative example of FIGS. 5-17, first and second opposed side knobs 228, 230 and a downwardly projecting bottom knob 232 are mounted to the receiver 202. Each knob has a narrow waist 234 and an enlarged head 236 as shown with reference to the bottom knob 232. A suture strand may be wrapped or tied around the waist 234 to secure or route the suture. O-rings 238, 240 are provided on the side knobs 228, 230 to grip a wrapped suture to facilitate securing and removing a suture strand. As a suture is wrapped around the side knobs 228, 230, it wedges between the resilient O-ring 238, 240 and knob compressing the O-ring. The pressure of the O-ring pressing the suture strand against the knob as well as the deformation of the O-ring around the suture strand temporarily secures the suture.

The needle assembly 300 includes a piston 310, a stem 330, a needle 350, and a button 390. The piston 310 has a generally cylindrical body 312 with a longitudinal axis 316 extending from a proximal end 318 to a distal end 320. A flange 322 extends radially outwardly from the body 312 near the distal end 320. The flange has opposed flattened sides 324. A bore 326 (FIG. 12) is formed coaxially in the piston 310 at the distal end of the body 312. The stem 330 includes an elongated hollow cylinder 332 having an outer diameter and an inner bore 334 defining a longitudinal axis 336 extending from a proximal end 338 to a distal end 340. The needle 350 is a generally cylindrical member having a shank 352 with an outer diameter defining a longitudinal axis 354 extending from a proximal end 356 to a distal tip 358. A flange 360 extends radially outwardly from the shank 352 at a position intermediate the proximal and distal ends. The needle 350 will be described in greater detail below. The button 390 has a generally cylindrical body with a longitudinal axis 391 extending from a proximal end 393 to a distal end 395. A bore 398 (FIG. 12) is formed coaxially in the button 390 at the distal end 395 of the body. The proximal portion of the needle shank 352 fits within the inner bore 334 of the stem at its distal end 340. The stem outer diameter, near its proximal end 338, fits within the bore 326 of the piston 310. The outer diameter of the piston 310 fits within the bore 204 of the receiver 202 in linear sliding relationship. The flat sides 324 of the piston engage the flat side walls 214 of the bore 204 to prevent the needle assembly from rotating relative to the receiver 202. The piston flange 322 abuts the proximal end of the intermediate portion 212 of the bore 204 of the receiver 202 to provide a stop to needle assembly proximal translation relative to the receiver 202. The outer diameter of the piston 310, near its proximal end, fits within the bore 398 of the button 390 and the button 390 abuts a proximal end 216 of the receiver to provide a stop to needle assembly distal translation relative to the receiver 202. The joints between the button 390 and piston 310, the piston 310 and the stem 330, and stem 330 and needle 350 are secured by pressing, gluing, pinning, welding, or other suitable securing means. Alternatively, two or more of these components or various combinations of them may be made as a single piece.

The barrel assembly 400 includes a barrel bushing 410, a barrel 430, and a foot 450. The bushing 410 has a generally cylindrical body 412 having a through bore 414 with a longitudinal axis 416 extending from a proximal end 418 to a distal end 420. A flange 422 extends radially outwardly from the body 412 at a position intermediate the proximal and distal ends. An enlarged counter bore 424 (FIG. 12) is formed coaxial with the through bore 414 at the distal end 420 of the body 412. The barrel 430 includes an elongated hollow cylinder 432 having an outer diameter and an inner bore 434 defining a longitudinal axis 436 extending from a proximal end 438 to a distal end 440. The foot 450 is a generally hook-shaped member having a hollow post 452 having an outer diameter and an inner bore 454 defining a longitudinal axis 456 extending from a proximal end 458 of the cylinder to a distal end 460 of the foot 450. The foot will be described in greater detail below. The foot post 452 outer diameter fits within the inner bore 434 of the barrel at its distal end 440. The barrel 430 outer diameter, near its proximal end 438, fits within the counter bore 424 of the bushing. A coiled compression spring 250 fits coaxially over the needle assembly 300 within the bore 204 of the receiver 202 and rests against the distal end of the piston flange 322. The barrel assembly 400 fits coaxially over the needle assembly 300 and the outer diameter of the bushing 410, near its proximal end 418, fits within the counter bore 208 of the receiver 202 and is pressed proximally until the flange 422 abuts the receiver distal end 210. The proximal end of the bushing retains the spring 250 within the bore 204. The joints between the foot 450 and barrel 430, the barrel 430 and bushing 410, and the bushing 410 and receiver 202 are secured by pressing, gluing, pinning, welding, or other suitable securing means. Alternatively, the bushing, barrel, foot, or any combination of them may be made as a single piece. Pressing the button 390 distally translates the needle assembly from a first, proximal, retracted position distally along the needle axis 354 compressing the spring 250 and extending the needle 350 through the foot 450 to a second, distal, extended position. Releasing the button 390 allows the spring 250 to expand and bias the needle assembly 300 back toward the first position. The needle assembly 300 of the illustrative example of FIGS. 5-17 is a linear arrangement mounted for linear, coaxial translation in the housing 200 and barrel assembly 400 with the needle projecting straight through the foot to increase rigidity and power facilitating driving the needle 350 through difficult to penetrate materials and access confined spaces. The barrel 430 may have a circular, polygonal, or any other cross sectional shape.

Figure 14:
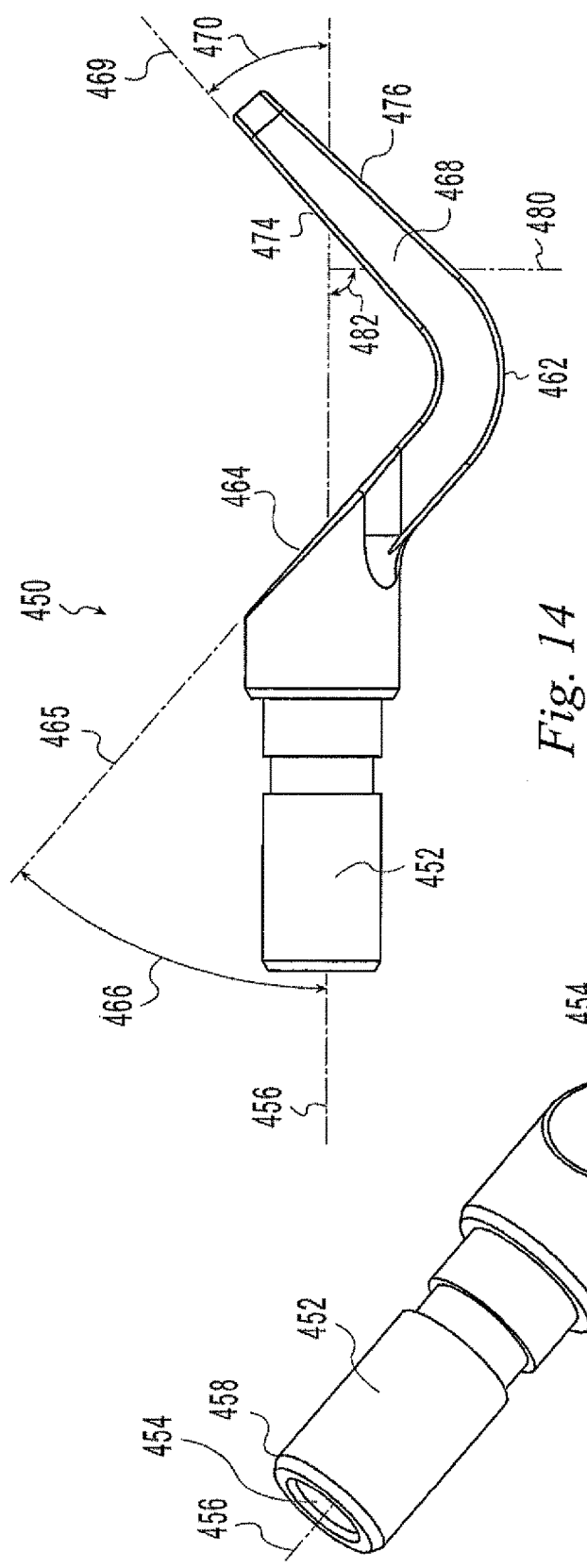
FIG. 14 is a side elevation view of the component of FIG. 13.
Figure 13:
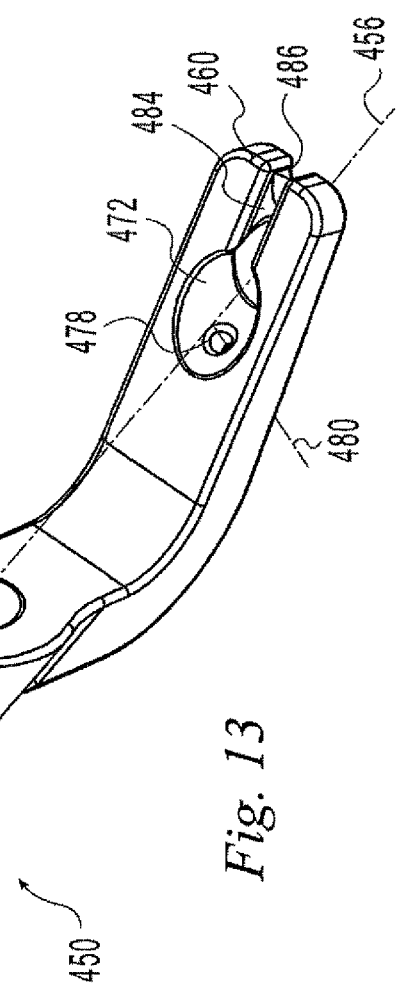
FIG. 13 is a perspective view of a component of the suture passer of FIG. 5.
Figure 18A:
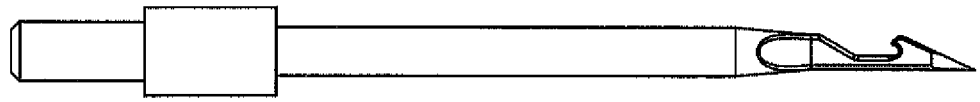
FIGS. 18A-G are bottom plan views of variations of the component of FIG. 15.
Figure 18B:
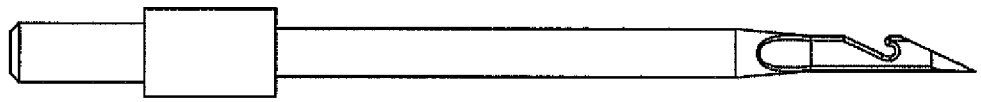
Figure 18C:
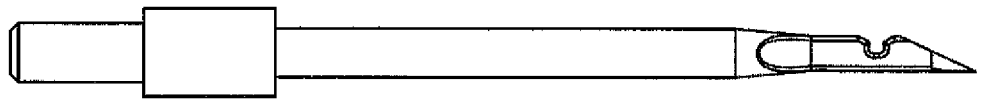
Figure 18D:
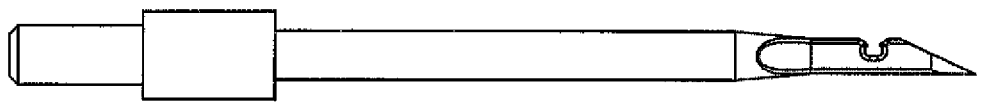
Figure 18E:
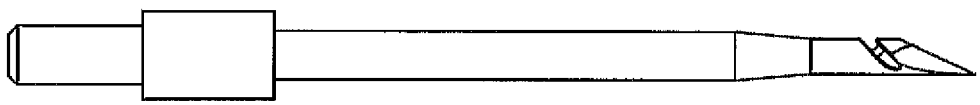
Figure 18F:
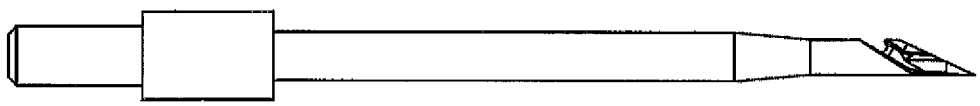
Figure 18G:
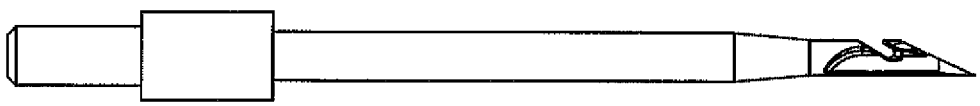

FIGS. 13 and 14 illustrate the foot 450 of the illustrative example of FIGS. 5-17 in greater detail. The hooked portion of the foot 450 includes an elbow 462 having a first, proximal portion 464 extending distally from the post 452 along a proximal portion axis 465 diverging from the bore axis 456 at a first angle 466 relative to the bore axis 456. A second, distal portion 468 extends distally from the first portion 464 along a distal portion axis 469 converging toward the bore axis 456 at a second angle 470 relative to the bore axis 456. The first and second angles 466, 470 are chosen to allow the foot to extend into a confined space, for example behind material such as a portion of soft tissue such as a tendon or ligament, and position the receiver 202 so as not to obstruct the users view of the foot and needle. The first angle 466 is in the range of 0 to 180 degrees; preferably 0 to 90 degrees; more preferably 25 to 55 degrees; more preferably 35 to 45 degrees. In the illustrative example of FIG. 14, the first angle 466 is approximately 42 degrees. The second angle 470 is in the range of 0 to 90 degrees; preferably 25 to 55 degrees; more preferably 35 to 45 degrees. In the illustrative example of FIGS. 13 and 14, the second angle 470 is also approximately 42 degrees. An eye 472 is formed through the second portion 468, from a proximal facing surface 474 to a distal facing surface 476, coaxial with the bore axis 456 for receiving the distal end of the needle 350 when the needle is in the second position. A hole 478 defining a hole axis 480 extends through the second portion 468 from the distal surface 476 and intersecting the eye 472. The hole 478 permits passing a suture strand from the distal surface 476 of the second portion 468 to the eye 472. The hole axis 480 forms an angle 482 relative to the bore axis 456. The angle 482 is between parallel to the proximal facing surface 474 of the second portion 468 and parallel to the distal facing surface of the first portion 464; preferably in the range of 45 to 135 degrees; more preferably 45 to 90 degrees. In the illustrative example of FIGS. 13 and 14, the hole angle 482 is approximately 90 degrees relative to the bore axis 456. A groove 484 is formed in the proximal surface 474 of the second portion 468 communicating from the eye 472 to the distal end 460. A notch 486 is formed through the distal end 460 from the proximal surface 474 to the distal surface 476 and communicating with the groove 484. The groove 484 and notch 486 are sized to receive a suture strand and retain the strand on the distal end of the foot 450. The proximal surface 474 of the second portion 468 of the foot 450 provides a supporting platform for material through which the needle 350 is passed. The eye 472 allows the needle 350 to penetrate all the way through the material and intercept a suture strand extending from the hole 478 to the groove 484.

FIGS. 15-17 illustrate the needle 350 of the illustrative example of FIGS. 5-17 in greater detail. A narrowed shaft 362 extends between the shank 352 and a sharp tip 364 at the distal end of the needle. A shoulder 366 defines the transition from the shank 352 to the shaft 362. The shaft 362 is generally rectangular in cross section with a top 368, a bottom 370, and opposing sides 372, 374. The corners 376 are rounded. The shaft 362 has a height 378 between the top 368 and bottom 370 and a width 380 between the sides 372, 374. Both the height 378 and width 380 of the shaft are narrower than the shank 352. The width 380 of the shaft 362 is greater than its height 378. The ratio of the width 380 to the height 378 is in the range of 1 to 3; preferably 2 to 3. In the illustrative example of FIGS. 15-17 the ratio is approximately 2.3. The distal end of the shaft is tapered in the width dimension from the full width to the tip 364. In the illustrative example of FIGS. 15-17, the shaft is tapered on a single side in the width dimension to form a single-sided bevel 382. The distal end of the shaft is tapered in the height dimension from the full height to the tip 364. In the illustrative example of FIGS. 15-17, the shaft is tapered on opposite sides in the height dimension to form a chisel portion 384. A notch 386 is formed in the side of the shaft 362 through the shaft 362 from the top 368 to the bottom 370. The notch 386 has an opening width 388 measured parallel to the needle axis 354, a depth 389 measured perpendicular to the needle axis 354, and a notch axis 392 forming an angle 394 to the needle axis 354. In the illustrative example of FIGS. 15-17, the notch has parallel side walls 396, 398 that are parallel to the axis 392. The notch width 388, depth 389, and angle 394 are selected to optimize the ability of the needle 350 to capture and retain a suture strand while avoiding snagging other material through which the needle 350 passes. FIGS. 18A-18G illustrate a variety of needle designs having varying notch width, depth, and angle. The present inventors have determined that the balance between capturing and retaining a suture strand and avoiding snagging is optimized, in the case of a suture strand with a diameter D, when the width of the notch is in the range of 0.9 D to 2 D. A notch width of 0.9 D creates a press fit depending on the resilient nature of the suture strand. Preferably, the notch width is in the range of 1 D to 1.5 D. Similarly, the notch depth is optimized when the depth is in the range of 0.75 D to 3 D. A notch depth of 0.75 D captures the suture but leaves a portion of the suture projecting from the notch. Preferably, the depth is in the range of 1 D to 2 D. The notch angle is in the range of 30 to 90 degrees; preferably 35 to 55 degrees. In the illustrative example of FIGS. 15-17, the notch was optimized for a USP#2-0 suture having a diameter in the range of 0.300-0.339 mm and has a width of 0.30 mm and a depth of 0.46 mm and an angle of 45 degrees. The notch opens toward the side of the needle 350 and suture passer 100. The bevel 382 leads from the tip 364 of the needle along the narrow side of the needle shaft 362 toward the opening of the notch 386. The needle may be sized to capture and pass one or more suture strands.

Figure 25:
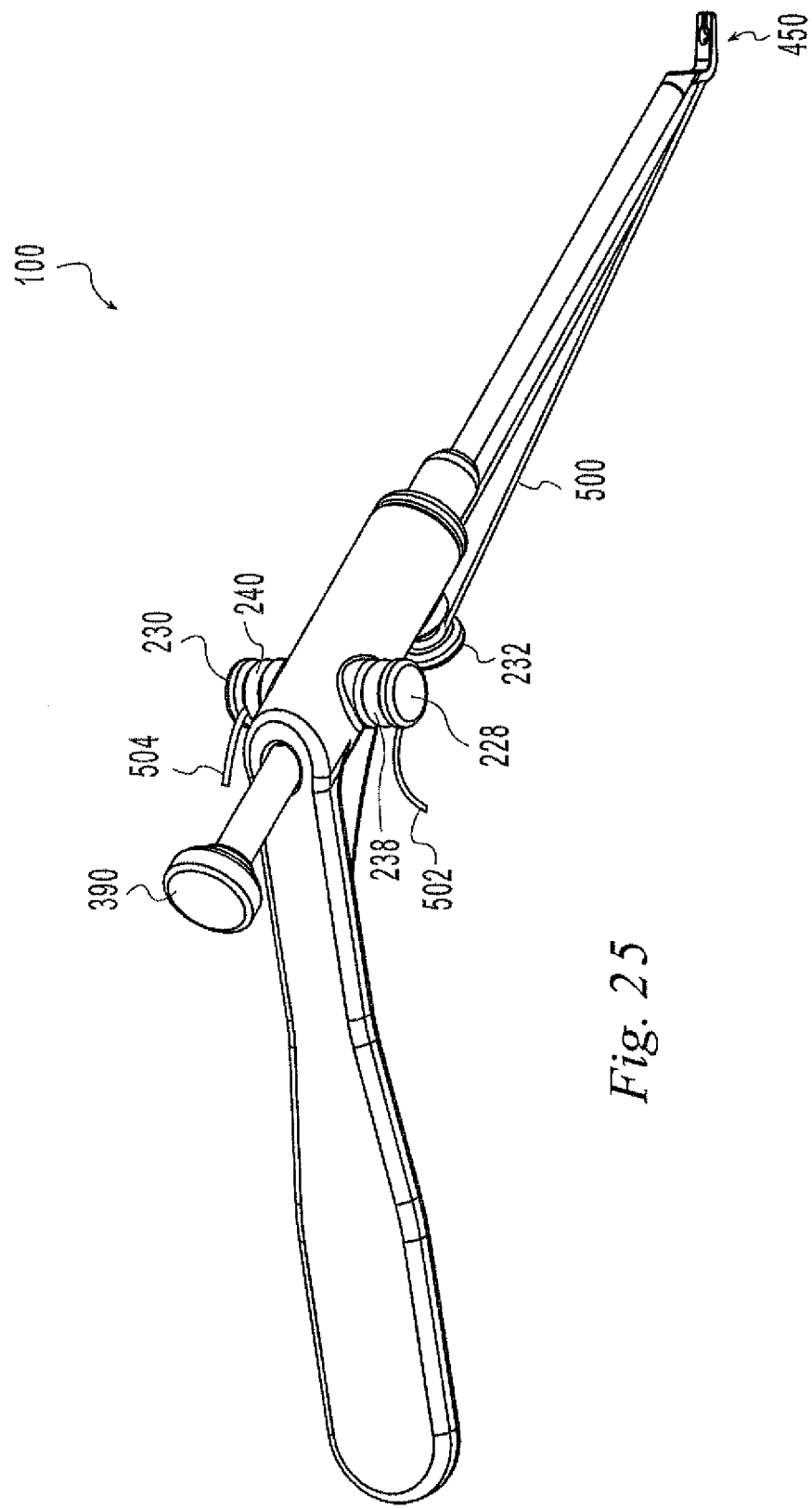
FIG. 25 is a perspective view of the suture passer of FIG. 5 illustrating a suture being loaded on the suture passer.
Figure 31:
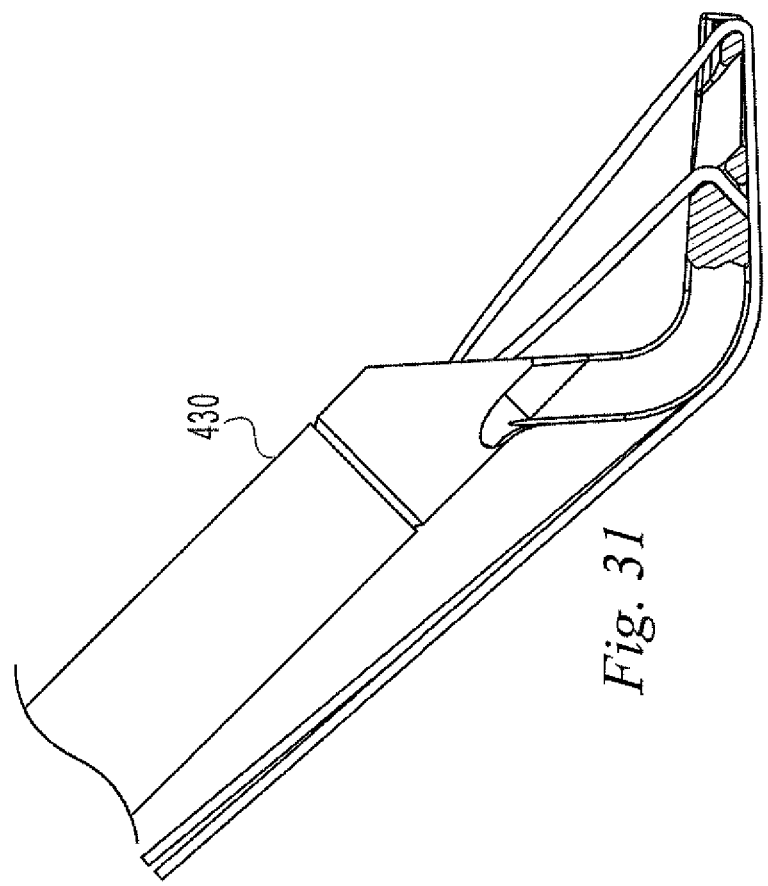
FIG. 31 is a partially sectioned side elevation view of the distal end of the suture passer of FIG. 5 illustrating the operation of the suture passer.

FIGS. 19-25 illustrate loading a suture strand 500, having a first end 502 and a second end 504 into the suture passer 100 of FIGS. 5-17. A first end 502 of the suture strand 500 is inserted through the hole 478 in the foot 450 from the distal surface 476 toward the eye 472 and extended past the proximal surface 474 as shown in FIGS. 19 and 20. The first end 502 of the suture strand is pulled distally to place the suture strand 500 in the groove 484 as shown in FIGS. 21 and 22. The suture strand 500 is wrapped over the distal end 460 in the notch 486 and pulled proximally over the distal surface 476 of the second portion of the foot 450 as shown in FIGS. 23 and 24. The ends 502, 504 of the suture strand are wrapped around the side knobs 228 and 230 and retained by the O-rings 238, 240. In the example of FIG. 25, the suture strand ends are routed proximally to the bottom knob 232 wrapped part-way around the proximal side of the knob 232 and secured on the side knob opposite the side on which the end was routed such that the suture strand is maintained near the center of the suture passer 100 and better retained on the foot 450.

FIGS. 26-31 illustrate the operation of the suture passer 100. When the button 390 is pressed distally, the needle assembly 300 moves distally relative to the housing and barrel assembly along the straight-line motion axis 506 of the suture passer which is coaxial with the needle axis 354 and foot bore axis 456. As the needle 350 approaches the suture strand 500, the bevel 382 contacts the suture strand 500 and wedges it sideways increasing the tension in the suture as shown in FIGS. 26 and 27. Further advancement of the needle 350 moves the notch 386 toward alignment with the suture strand 500 until the tension in the suture causes the suture 500 to move into the notch 386 as shown in FIGS. 28 and 29. Releasing pressure on button 390 allows the spring 250 to bias the needle assembly proximally. Depending on the resilience of the suture 500 and how tightly it is secured to the knobs 228, 230, the needle may or may not be able to retract. By releasing one or both ends 502, 504 of the suture 500, the suture ends can move toward the foot 450 and allow the needle to retract and pull a bight 508 of suture 500 proximally toward the barrel 430 as shown in FIG. 30. Further retraction of the needle 350 pulls the bight 508 into the barrel 430 (FIG. 31) trapping the bight 508 between the needle 350 and barrel bore 434. To release the bight 508, the button 390 is pressed to advance the needle 350 out of the barrel 430.

Figure 32:
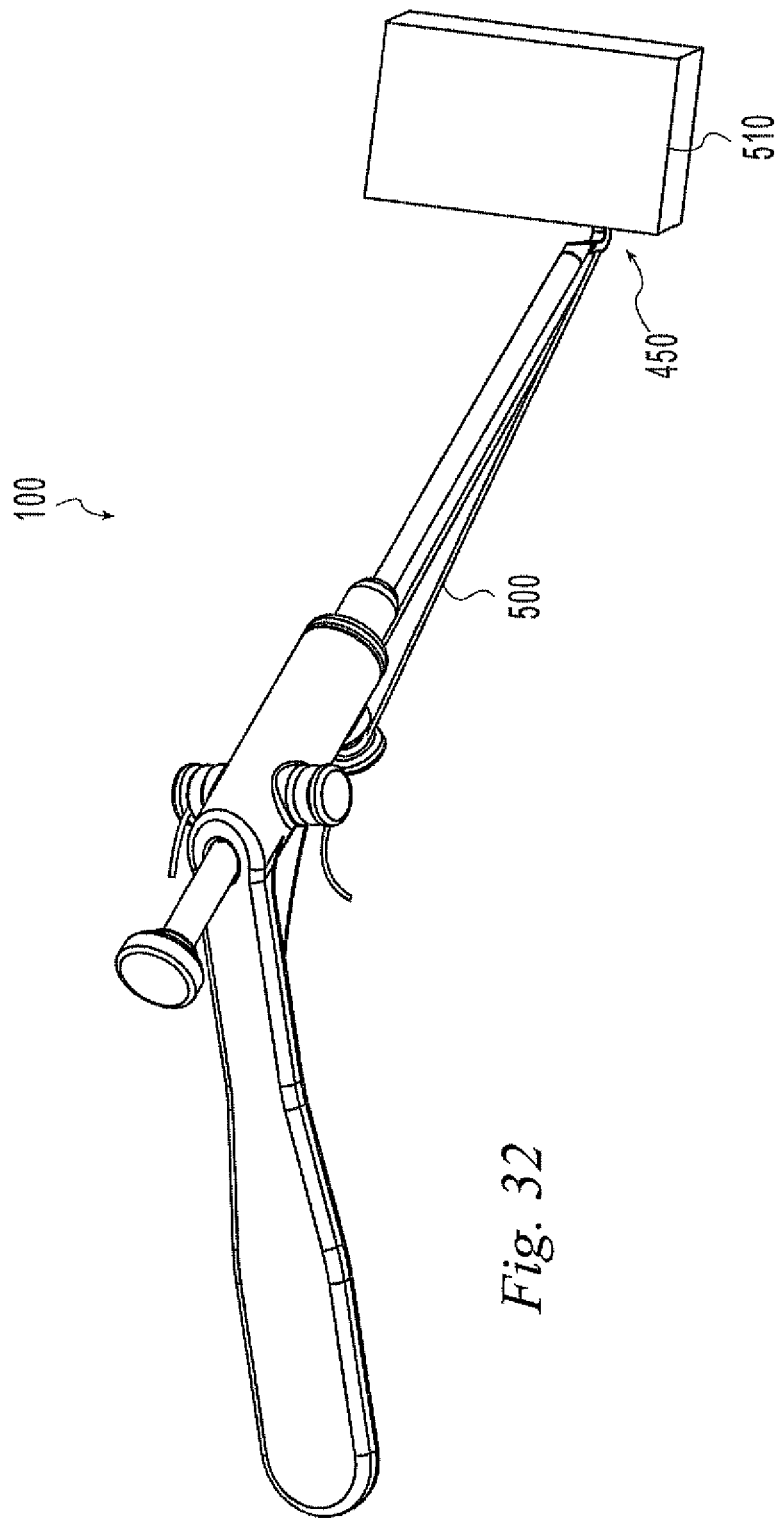
Figure 33:
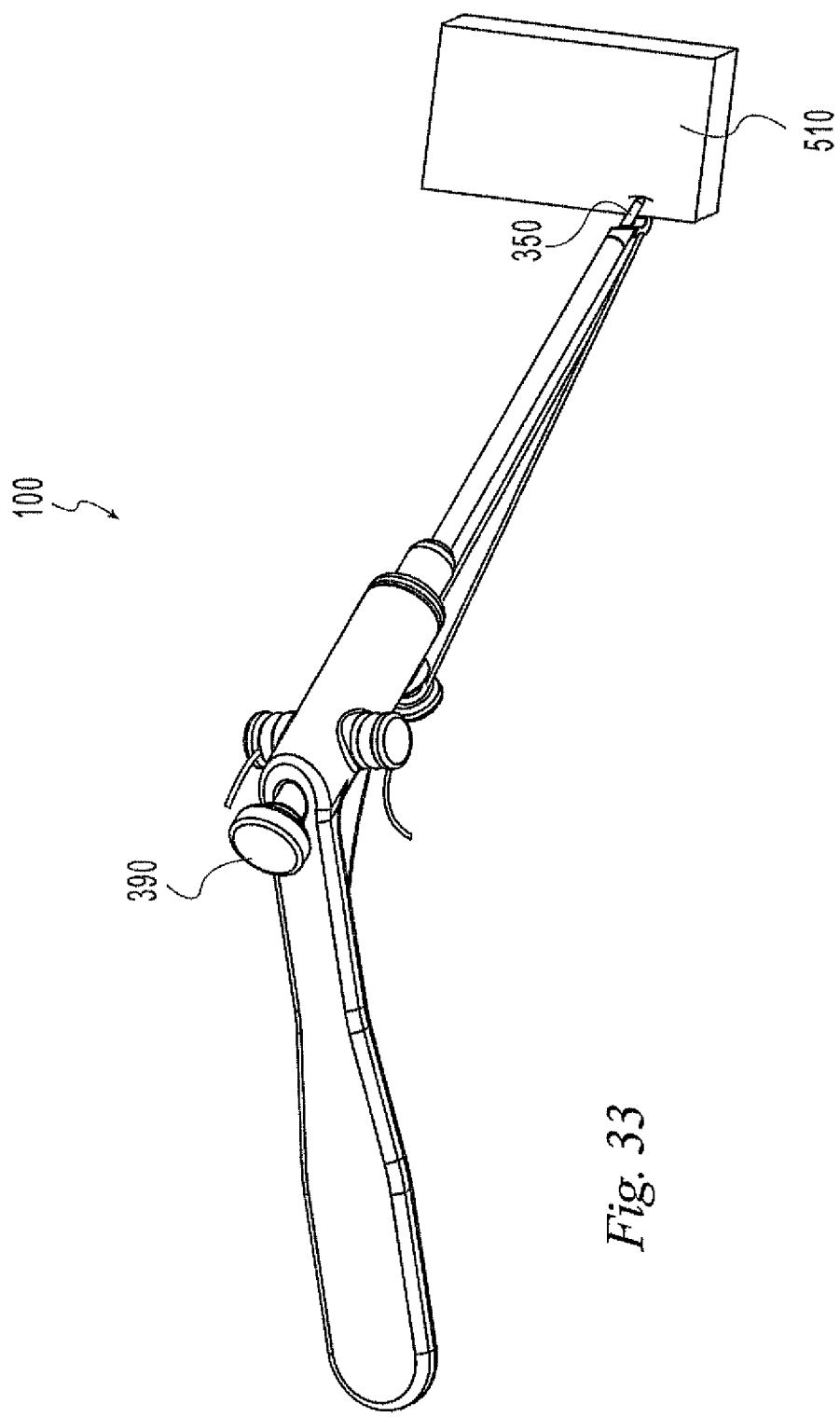
Figure 34:
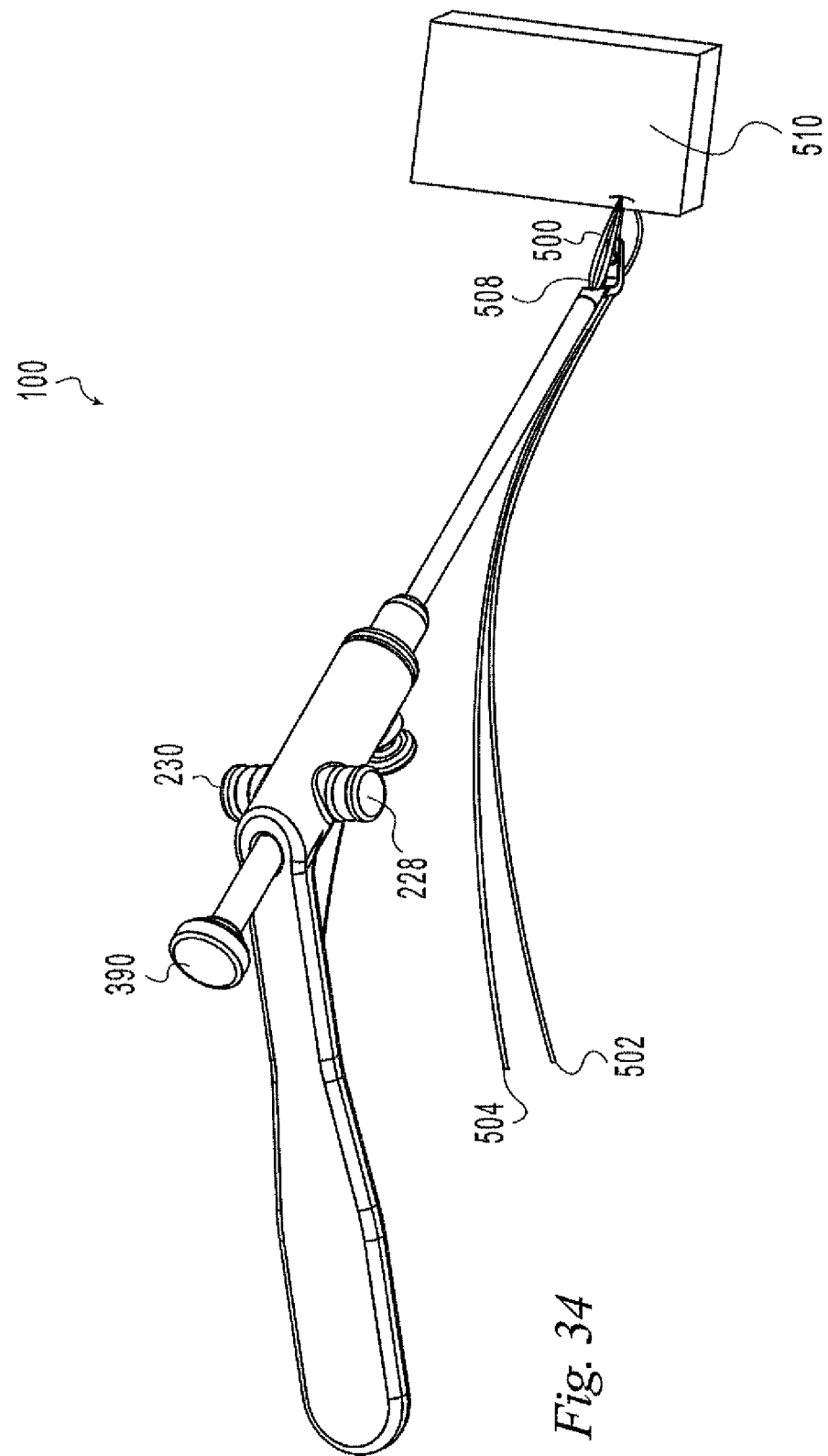
Figure 35:
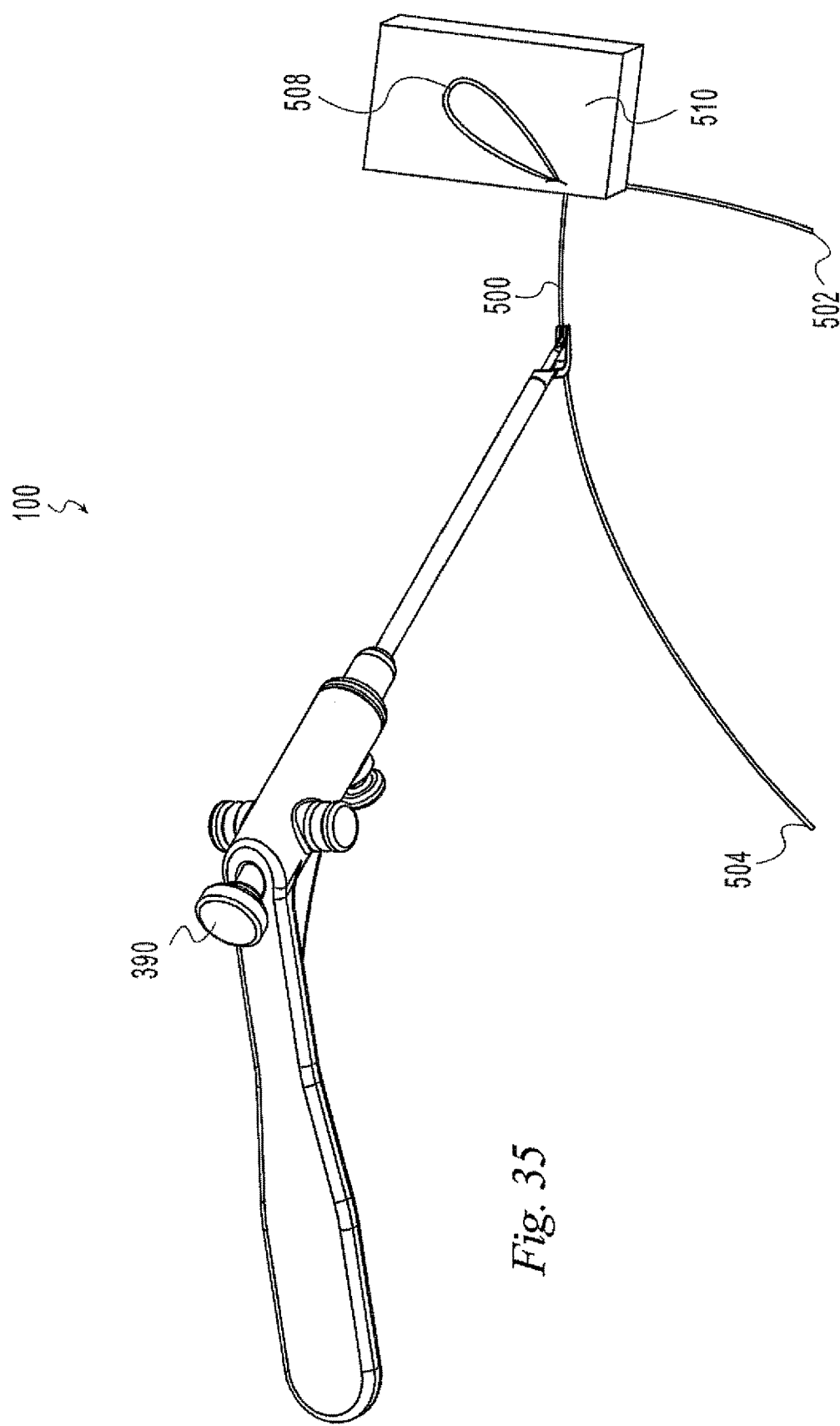

FIGS. 32-50 depict examples of the illustrative suture passer 100 in use to pass sutures through a material to create a variety of stitches. Referring to FIG. 32, the suture passer has been loaded as described relative to FIGS. 19-25. The foot 450 is positioned adjacent material 510 through which it is desired to pass the suture 500. The second portion 468 of the foot is positioned behind the material 510 with the proximal surface 474 supporting the material 510. Referring to FIG. 33, the button 390 is pressed to advance the needle 350 through the material 510 and capture the suture 500 in the eye 472 of the foot 450. Referring to FIG. 34, the button 390 has been released and the suture ends 502 and 504 have been freed from the knobs 228, 230 and allowed to move distally so that the needle 350 has retracted and pulled a bight 508 of suture 500 through the material 510. Referring to FIG. 35, the button 390 has been pressed to release the bight 508 and the first end 502 has been allowed to drop free from the passer 100. Referring to FIGS. 36 and 37, the second end 504 has been removed from the foot 450 by pulling the passer 100 proximally away from the bight or by pulling the suture 500 distally away from the foot 450. The suture ends 502, 504 have been passed through the bight 508 and pulled to form a stitch in the form of a hitch 512.

Referring to FIG. 38, instead of pulling the ends 502, 504 through the bight 508, the first end 502 has been pulled through the material 510 by pulling on one side of the bight 508 to form a simple stich 514.

Figure 39:
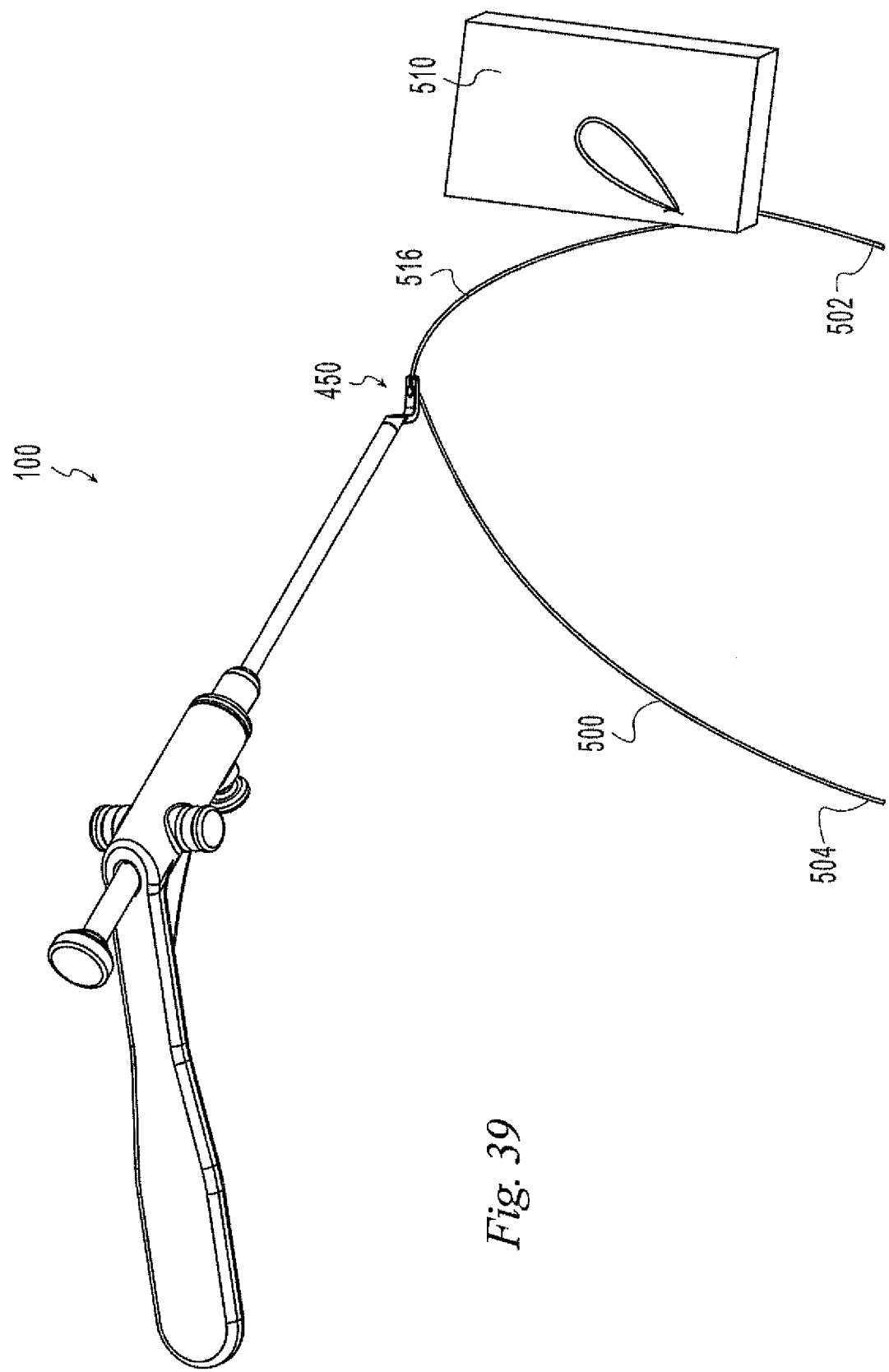
Figure 40:
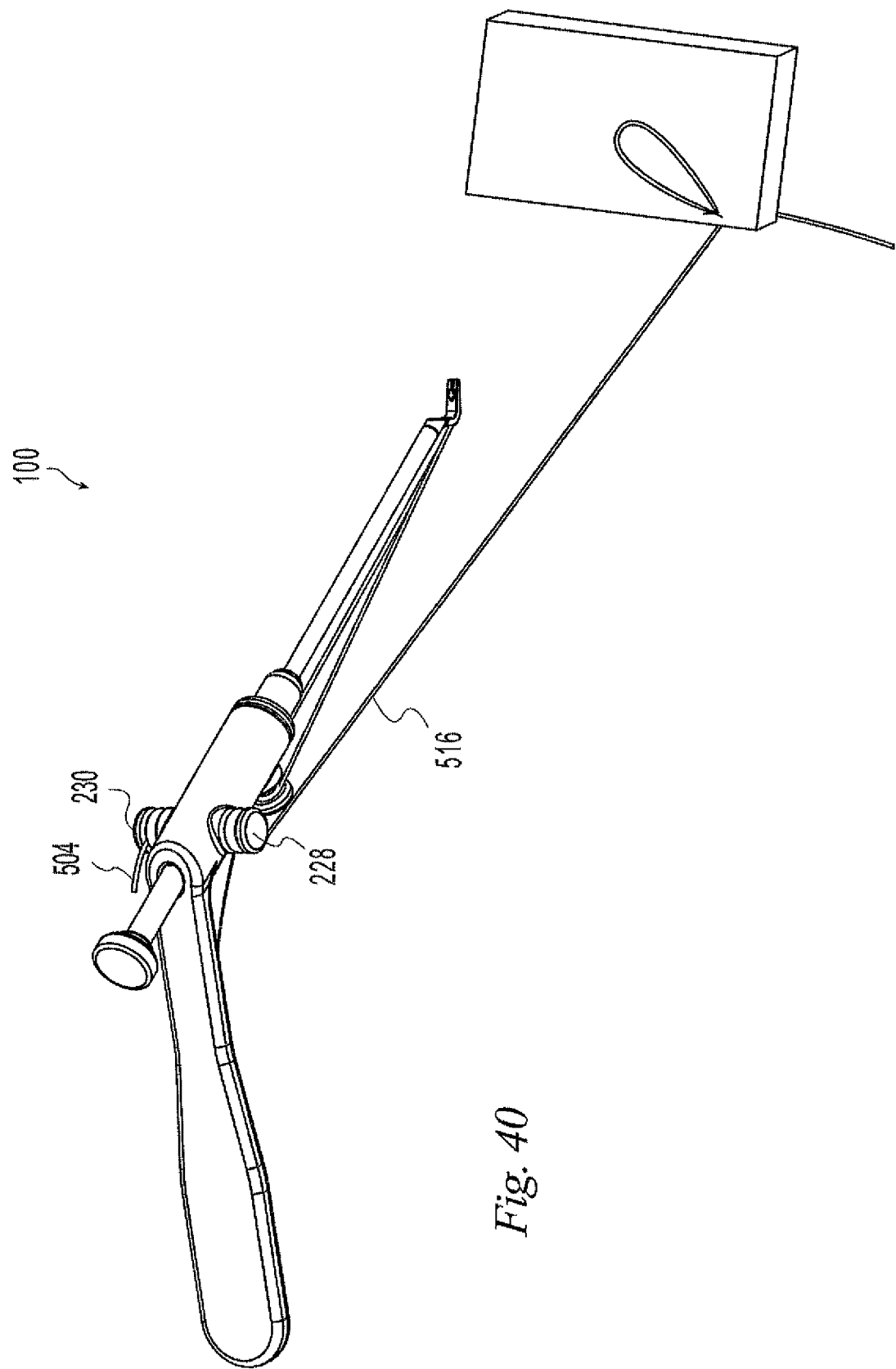
Figure 41:
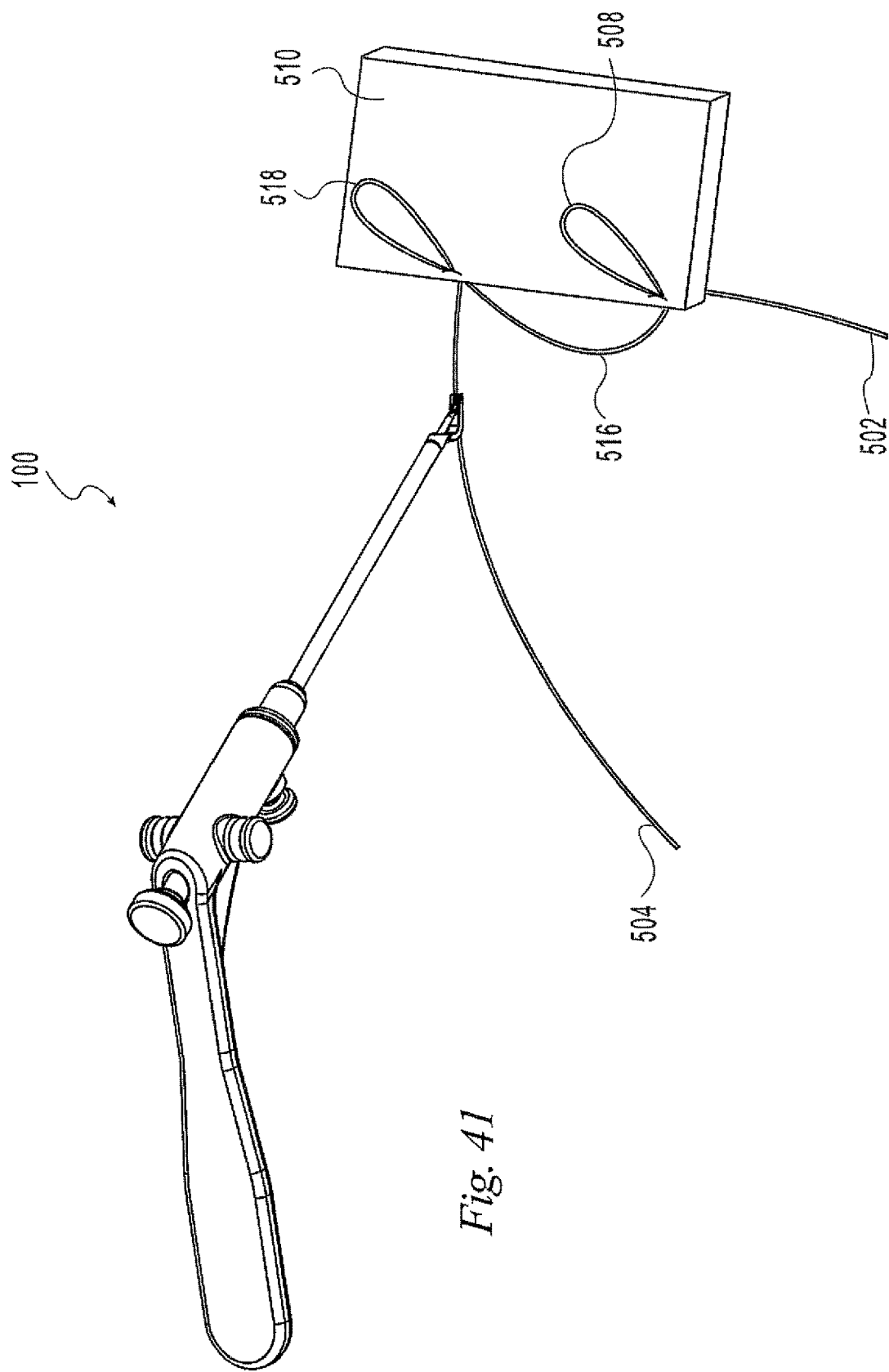

Referring to FIG. 39, the passer 100 is prepared for making a running stitch by pulling suture 500 distally through the foot to create slack 516 between the foot 450 and material 510. Referring to FIG. 40, the slack 516 and the second end 504 have been pulled proximally and secured to the knobs 228, 230. Referring to FIG. 41 a second bight 518 has been passed through the material 510 in the same manner as the first bight 508 and the slack 516 and second end 504 have been released from the passer 100.

Figure 42:
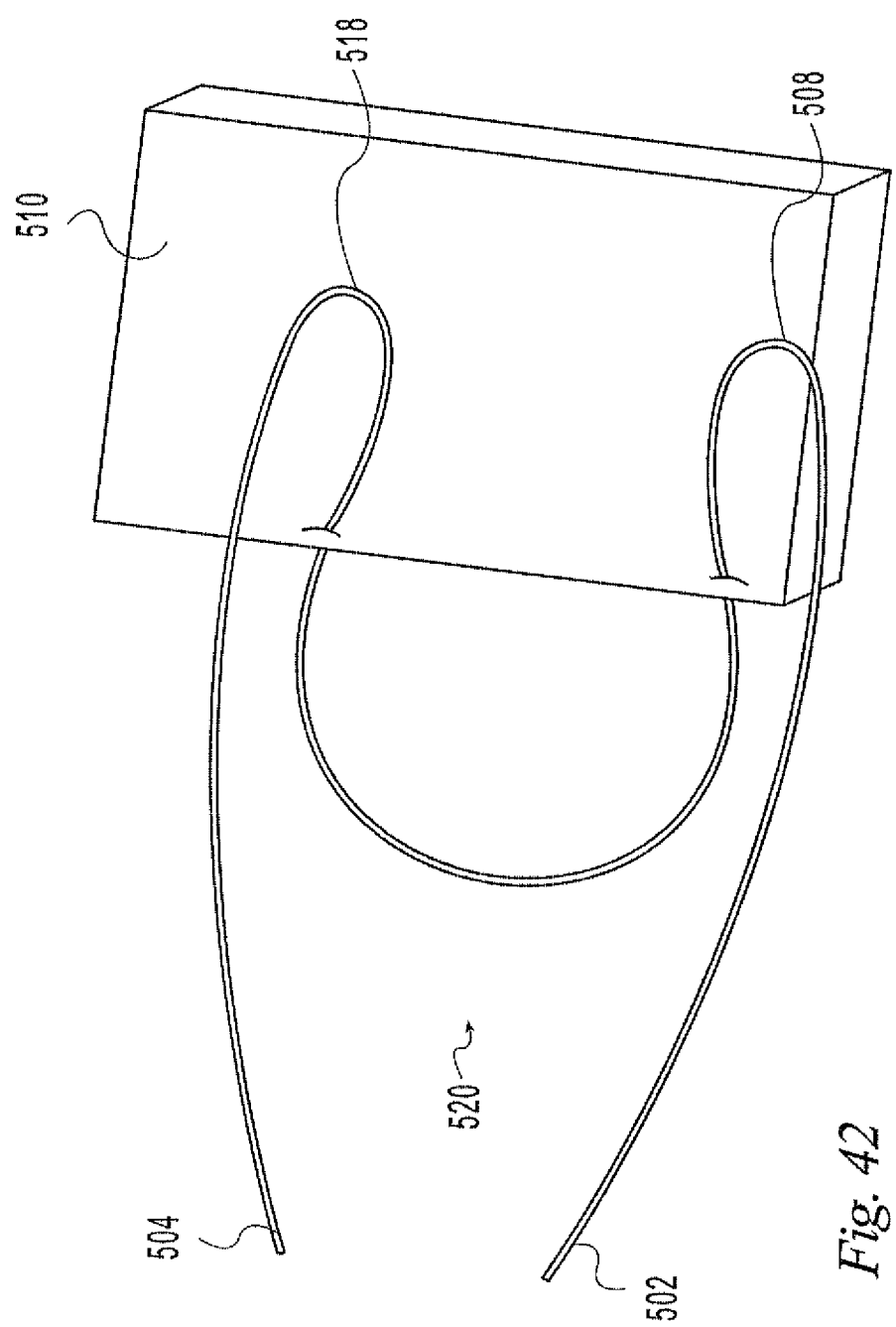

Referring to FIG. 42, the first and second ends 502, 504 have been pulled through to the front side of the material 510 by pulling on one side of each of the bights 508, 518 to form a mattress stitch 520 in the material 510.

Figure 43:
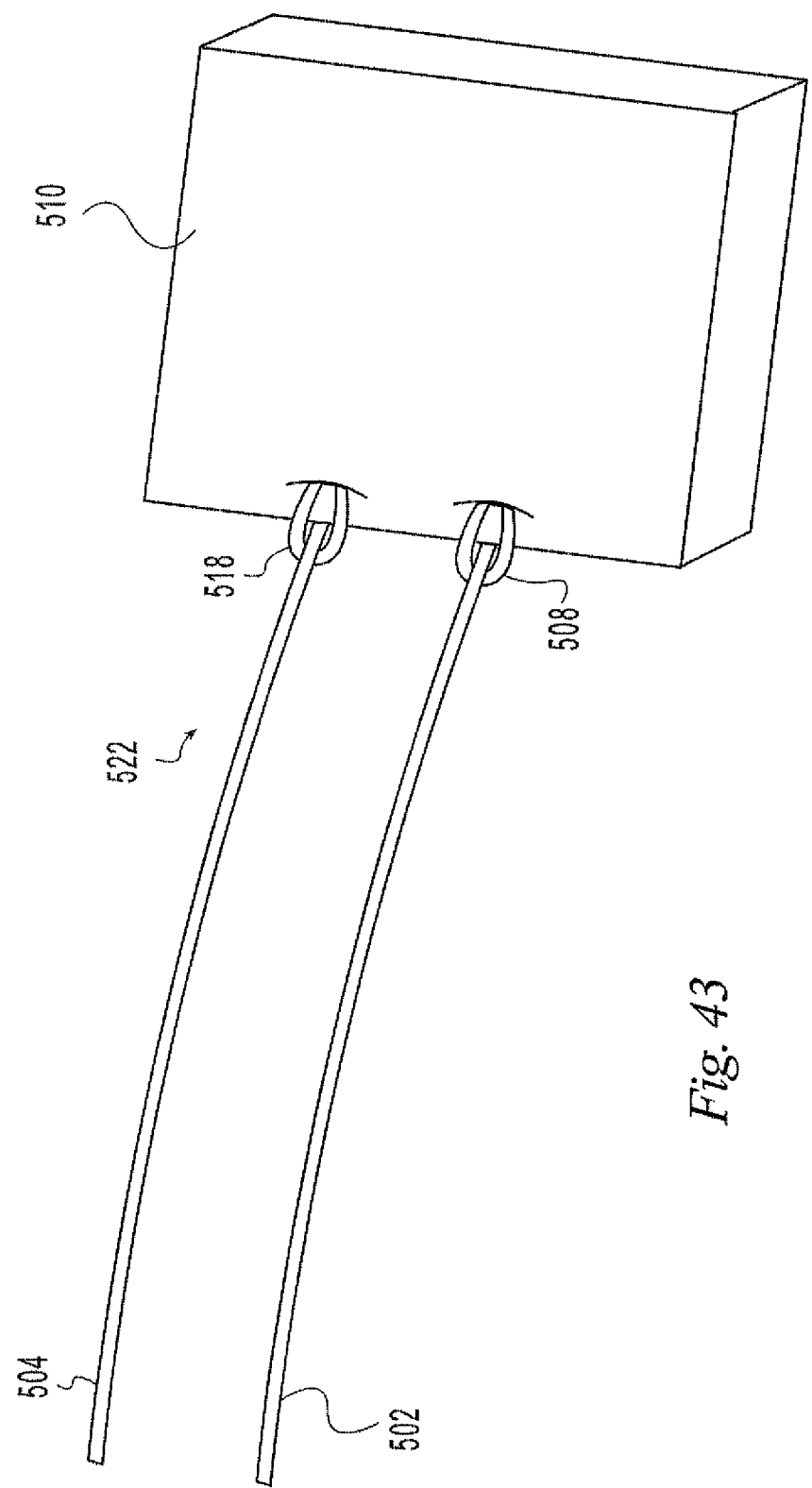

Referring to FIG. 43, instead of the ends 502, 504 being pulled through the material the first end 502 has been placed through the first bight 508 and the second end 504 has been placed through the second bight 518 to form a modified mattress stitch 522 with each end 502, 504 secured by a hitch.

Figure 44:
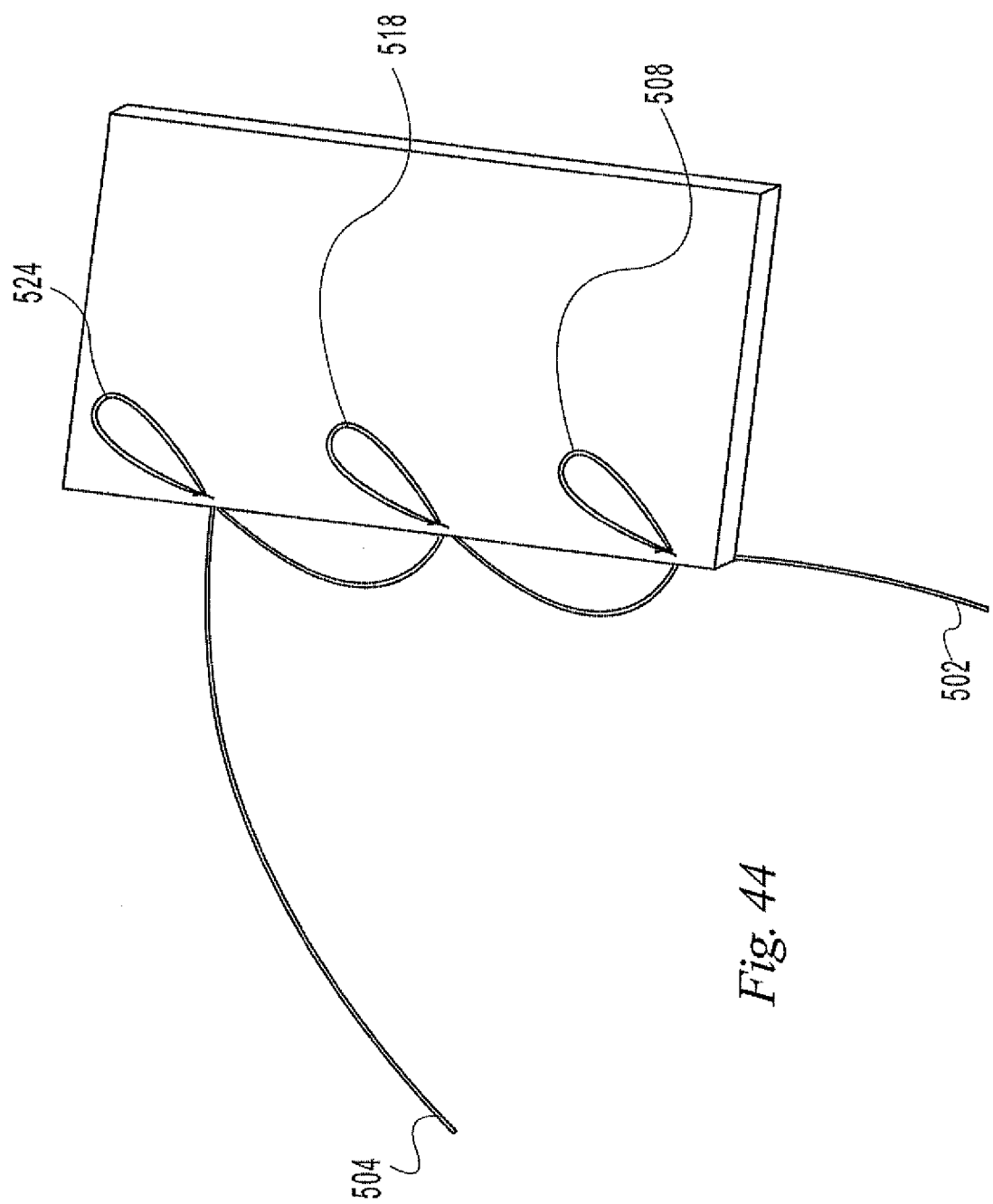
Figure 45:
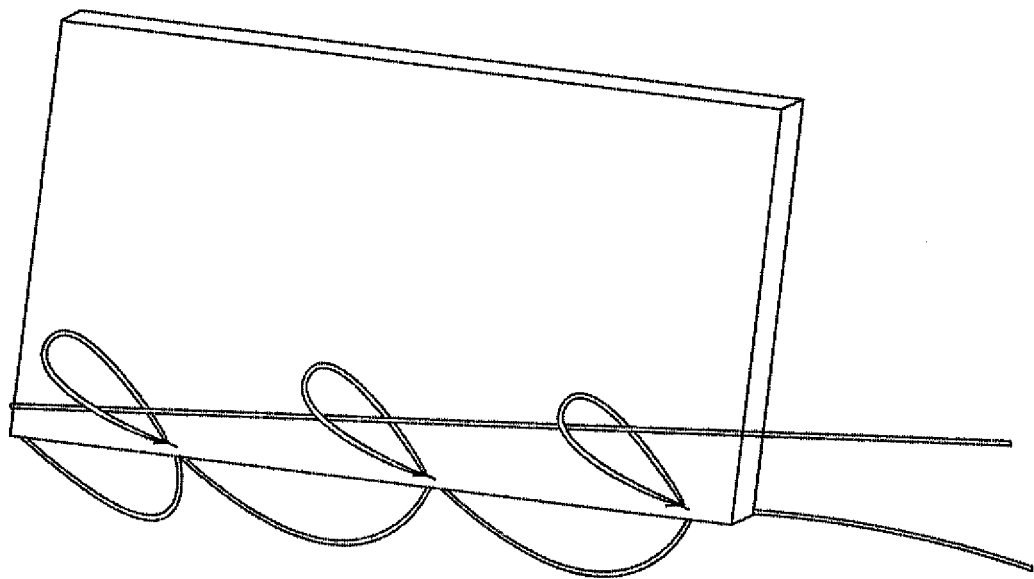

Referring to FIG. 44, a third bight 524 has been pulled through the material in the same manner as the first two bights 508, 518. A stitch may be formed by placing one or both ends 502, 504 through the bights 508, 518, 524 to lock the bights as shown in FIG. 45.

Figure 46:
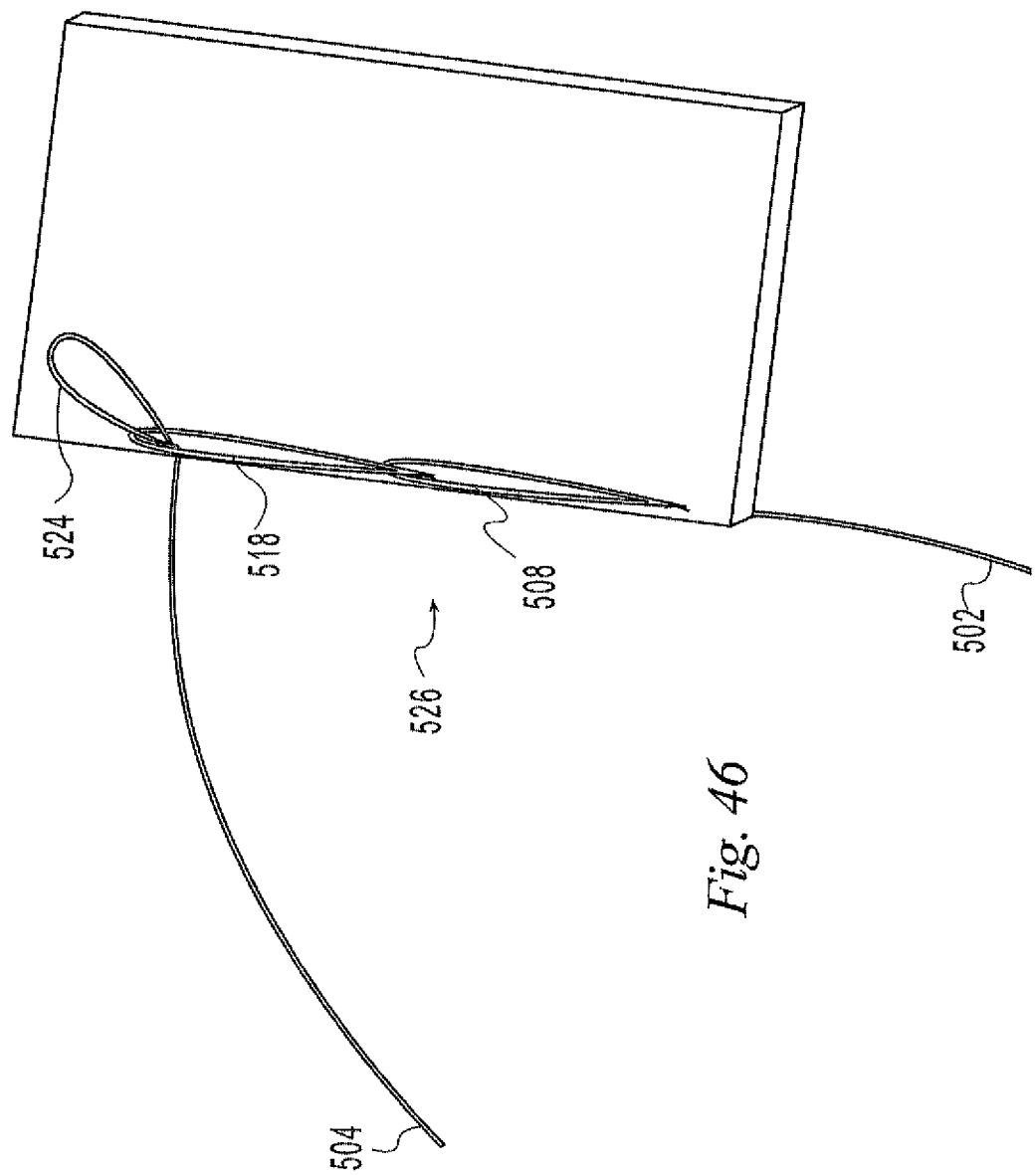

Referring to FIG. 46, instead of placing the ends through the bights, the second bight 518 has been looped through the first bight 508, and the third bight 524 has been looped through the second bight 518 to form a chain stitch 526.

Figure 47:
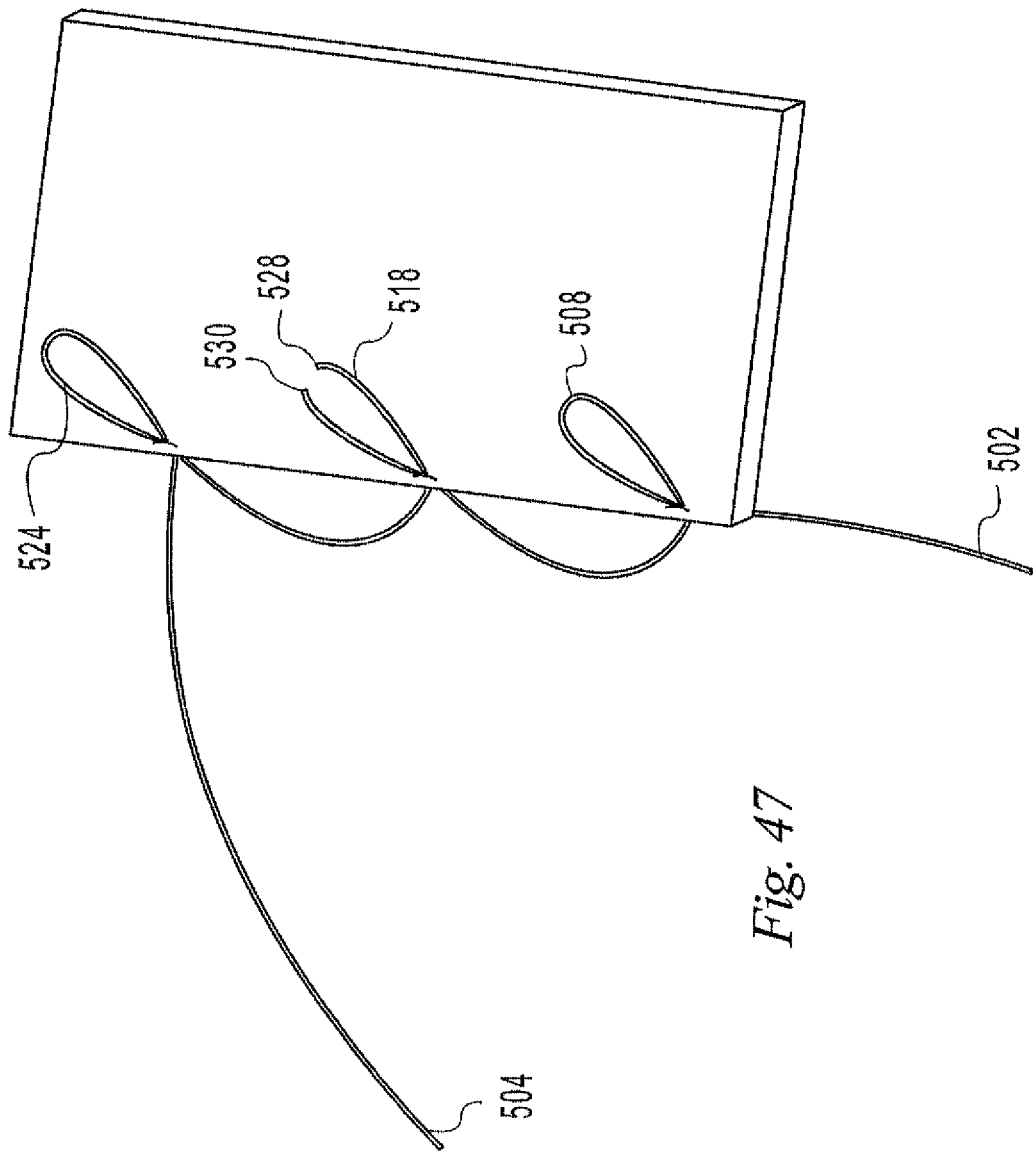
Figure 48:
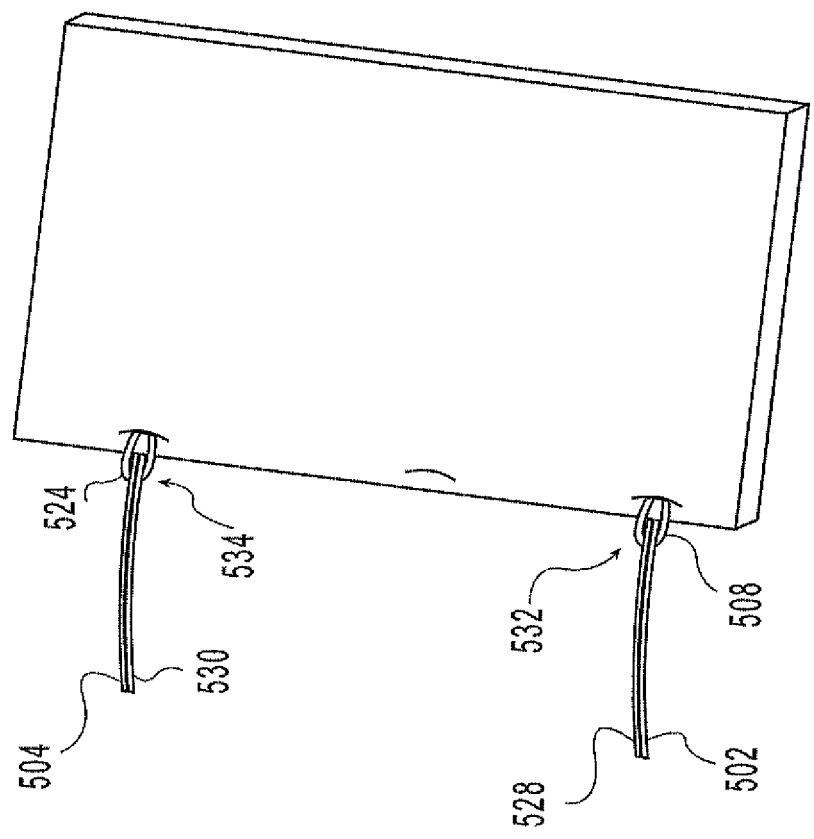

Referring to FIGS. 47 and 48, another alternative to forming stitches with three bights is shown. Here, the second bight 518 has been cut to form third and fourth ends 528, 530. The third and fourth ends 528, 530 are pulled back through the material 510 and then the first and third ends 502, 528 are placed through the first bight 508 to form a first hitch 532 and the second and fourth ends 504, 530 are placed through the third bight 524 to form a second hitch 534.

Alternatively, as shown in FIGS. 49 and 50, the same construct could be produced by forming two bights 508, 518, and cutting through the slack 536 on the back side of the material 510 to produce third and fourth ends 538, 540 which with the first and second ends 502, 504 are used to form hitches 542, 544.

The illustrative examples of FIGS. 5-50 have been shown in use to pass suture through material to form illustrative stitches. The invention is not limited to the specific instruments and methods depicted. Furthermore, it is to be understood that instruments and methods according to the invention may be used to pass any number of bights of suture through one or more materials and form any desirable construct.

The illustrative examples of FIGS. 51-77 depict instruments and techniques to pass a suture through a material. Instruments and techniques according to the illustrative examples of FIGS. 51-77 may be used to pass a suture through any material, at surgical sites anywhere in a patient's body, and for any purpose. Instruments and techniques according to the illustrative examples of FIGS. 51-77 are particularly useful to pass a suture through a bone tunnel in an orthopedic procedure. For example, it is often desirable to pass a suture through a bone tunnel which in turn is used to pass a graft into the tunnel or attach a graft in the tunnel. While suture passers in accordance with the illustrative examples of FIGS. 51-77 may be used with any material at any location, and in particular with any bone adjacent any joint within a patient's body, the illustrative examples are shown in use with a small bone joint such as in a hand or foot to form a tunnel in and pass a graft into a metacarpal or metatarsal bone. In particular, the illustrative examples are shown in use with a phalanx bone of the foot.

Figure 51:
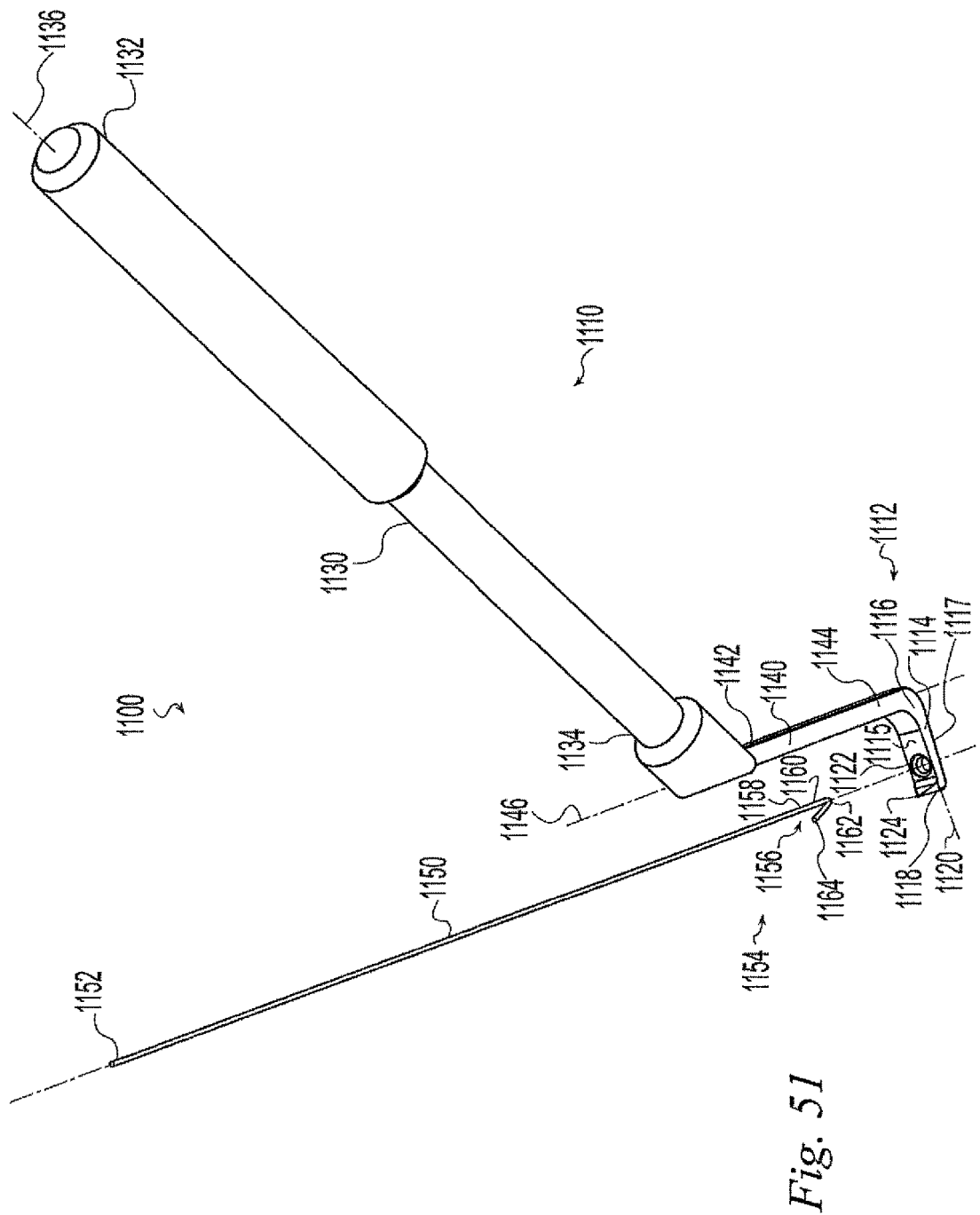
FIG. 51 is an exploded perspective view of an illustrative example of a suture passer according to the present invention.

FIG. 51 depicts an illustrative example of a suture passer 1100. The suture passer 1100 includes a suture retriever 1110 and a suture 1150. The retriever 1110 includes a receiver 1112 able to receive and retain a portion of the suture 1150. In the illustrative example of FIG. 51, the receiver 1112 includes a foot 1114 positionable on one side of a material through which the suture is to be passed. The foot 1114 has a proximal end 1116, a distal end 1118, a front surface 1115, a back surface 1117 and a longitudinal axis 1120 extending between the proximal and distal ends. The foot has an opening 1122 defining a passage through a portion of the receiver for receiving the suture 1150 and a sharp tip 1124 able to engage the material and aid in maintaining the foot 1114 in a desired location. In the illustrative example of FIG. 51, the retriever 1110 further includes a handle 1130 having a proximal end 1132, a distal end 1134, and a longitudinal axis 1136 extending between the proximal and distal ends. The receiver 1112 may be mounted directly to the distal end 1134 of the handle. In the illustrative example of FIG. 51, the receiver 1112 is offset from the handle. An extension 1140 having a proximal end 1142, a distal end 1144, and a longitudinal extension axis 1146 extends away from the distal end 1134 of the handle transverse to the handle axis 1136. The foot 1114 is mounted to the distal end 1144 of the extension 1140 and extends away from the extension 1140 transverse to the extension axis 1146.

The suture 1150 includes a proximal end 1152 and a distal end 1154. The distal end includes a stopper 1156. In the illustrative example of FIG. 51 the stopper 1156 includes a hook 1158 formed on the distal end 1154. For example, the distal end may be bent, molded, heat set, or otherwise formed into a hook shape. The hook 1158 includes a shank 1160, a bend 1162, and a barb 1164. The hook 1158 is receivable in the opening 1122. As the hook 1158 is advanced through the opening 1122, the barb 1164 and shank 1160 engage the sides of the opening 1122 and the barb 1164 moves toward the shank 1160. This movement changes the orientation of the hook to a receivable orientation in which the barb-shank maximum dimension is smaller than the opening 1122 maximum dimension and the hook passes through the opening. Once the hook 1158 is through the opening 1122, the barb 1164 springs away from the shank 1160 and the hook orientation changes to a retention orientation. Pulling the hook 1158 back toward the opening causes the barb 1164 to engage the back surface 1117 of the foot and resist withdrawal. The bend of the hook 1158 is such that relatively small movement of the barb 1164 is necessary for insertion of the hook through the opening 1122 but relatively large movement of the barb 1164, in the opposite direction, is necessary for removal. The hook 1158 may be withdrawn by forcing the barb to straighten or by clipping the hook 1158 off of the suture 1150.

The proximal end of the suture may be unmodified or it may include a loop, knot, hook, barb, or other feature for engaging another material.

In use, the receiver 1112 is positioned behind material through which the suture 1150 is to be passed. The distal end 1154 of the suture is advanced through the material and the stopper 1156 is engaged with the receiver 1112. The receiver 1112 is then withdrawn from behind the material to advance the suture further and retrieve it partially or fully through the material. The suture 1150 may be used to connect the material to another material. For example the suture 1150 may be used to attach soft tissue to bone. The suture 1150 may be used to retrieve something through the material. For example, the suture 1150 may be used to retrieve a graft through a bone tunnel. In the illustrative example of FIG. 51, the foot 1114 may be positioned adjacent a bone with the opening 1122 aligned with a tunnel formed in the bone and the tip 1124 engaged with the bone. The distal end 1154 of the suture 1150 may be advanced through the bone tunnel and opening 1122 until the hook 1158 engages the foot 1114. The proximal end 1152 of the suture may be secured to a graft such as by tying, stitching, looping, knotting, hooking, or other securing mechanism. The foot may then be withdrawn away from the bone tunnel to retrieve the distal 1154 end of the suture and pull the graft with it. Further pulling of the suture advances the graft into the bone tunnel.

FIGS. 52-59 depict an illustrative example of a suture passer 1200 similar to that of FIG. 51 and including a suture retriever 1300 and a suture 1400. In the illustrative example of FIGS. 52-59, the suture retriever 1300 includes a handle 1310, a receiver 1320, and a guide 1380. The handle 1310 includes a proximal end 1312, a distal end 1314, and a longitudinal axis 1316 extending between the proximal and distal ends. The receiver 1320 includes a foot 1324 positionable on one side of a material through which the suture is to be passed. The foot 1324 has a proximal end 1326, a distal end 1328, a front surface 1325, a back surface 1327 and a longitudinal axis 1330 extending between the proximal and distal ends. The foot 1324 has an opening 1332 having an opening axis and able to receiving the suture 1400. The opening 1332 includes an enlarged counterbore 1333. The foot further includes a sharp tip 1334 able to engage the material and aid in maintaining the foot 1324 in a desired location. The receiver 1320 is offset from the handle 1310. An extension 1340 having a proximal end 1342, a distal end 1344, and a longitudinal extension axis 1346 extends away from the distal end 1314 of the handle transverse to the handle axis 1316. The foot 1324 is mounted to the distal end 1344 of the extension 1340 and extends away from the extension 1340 transverse to the extension axis 1346.

The guide 1380 includes a tube 1382 having an inner surface 1384, an outer surface 1386, a proximal end 1388, and a distal end 1390. The inner surface 1384 defines an inner diameter and a longitudinal axis 1392. The tube 1382 is mounted to the distal end 1314 of the handle 1310 with the tube axis 1392 transverse to the handle axis 1316 and coaxial with the opening 1332 in the foot 1324. The handle 1310 axis 1316 forms an angle 1317 with the tube axis 1392. The angle 1317 facilitates manipulating the retriever 1300 while maintaining a line of sight for the user and to prevent interference with tissues surrounding the surgical site. The angle 1317 may have any suitable value. Preferably the angle 1317 is in the range of 90 to 270 degrees. The handle 1310 may also be mounted at any location around the circumference of the tube 1382. In the illustrative embodiment of FIGS. 52-59, the handle is coplanar with the foot 1324. The tube 1382 includes a slot 1394 through the sidewall of the tube from the inner surface 1384 to the outer surface 1386 and extending from the proximal end 1388 to the distal end 1390. The guide 1380 and foot 1324 define a space 1396 between them for receiving a bone.

The suture 1400 includes a proximal end 1402 and a distal end 1404. The distal end includes a stopper 1406. In the illustrative example of FIGS. 52-59 the stopper 1406 includes a pledget 1408. The pledget 1408 is mounted to the suture 1400 such as by adhering, welding, crimping, molding or other suitable mounting method. The pledget 1408 may also be formed as a unitary part of the suture. The pledget is resilient to allow it to bend or compress to fit through the opening 1332. It may also be toggled to one side such as for example by bending the suture adjacent the pledget 1408 to fit through the opening 1332. In the illustrative example of FIGS. 52-59, the pledget 1408 includes radially extending tabs 1410, 1412 that bend from substantially perpendicular to the suture 1400 to substantially parallel to the suture 1400 to reduce the radial dimension of the pledget 1408 and allow it to pass through the opening in a receivable orientation. Once the pledget 1408 is through the opening 1332, the tabs 1410, 1412 spring back to their initial position and resume a retention orientation. The proximal end of the suture 1400 includes a loop 1420. The loop may be formed by tying a knot in a bight of a single or multiple strand suture 1400, tying the ends of multiple strands together, splitting a monofilament strand, molding, or other suitable loop formation method. In the illustrative example of FIGS. 52-59, the loop is formed by molding a loop on a monofilament strand.

Figure 60:
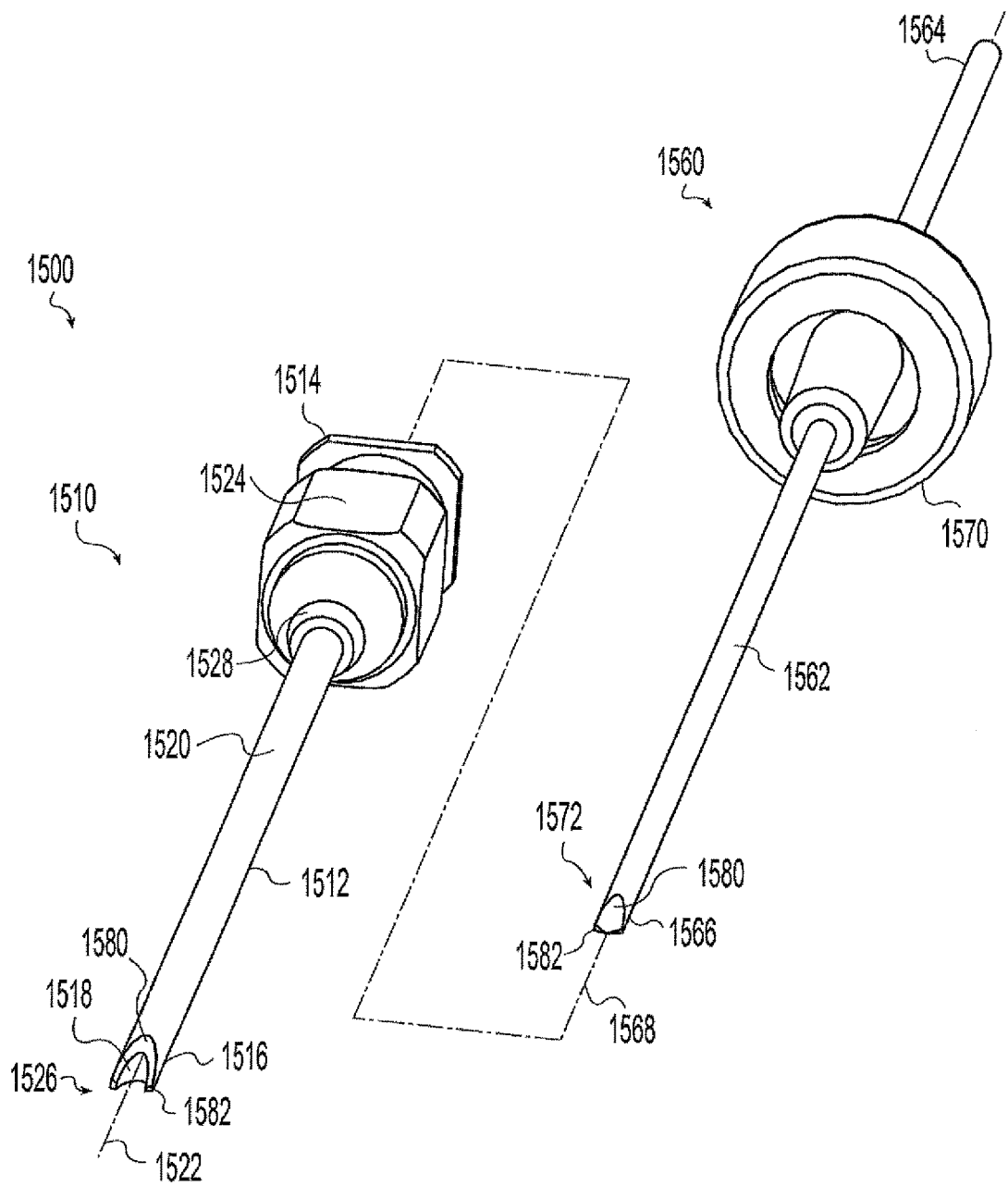
FIG. 60 is a perspective view of a drill assembly useable with the suture passer of FIG. 52.

FIG. 60 illustrates a drill assembly 1500 useable with the suture passer 200. The drill assembly 1500 includes a drill tube 1510 and an obturator 1560. The drill tube 1510 includes a tubular body 1512 having a proximal end 1514, a distal end 1516, an inner surface 1518, and an outer surface 1520. The inner surface 1518 defines an inner diameter and a longitudinal axis 1522 extending between the proximal and distal ends. In the illustrative embodiment of FIG. 60, a connector 1524 is mounted to the drill tube 1510 near the proximal end 1514. In the illustrative example of FIG. 60, the connector 1524 is a female Luer-type fitting. A stop 1528 extends radially outwardly from the body 1512.

The obturator 1560 includes an elongated body 1562 having a proximal end 1564, a distal end 1566, and a longitudinal axis 1568 extending between the proximal and distal ends. In the illustrative embodiment of FIG. 60, a connector 1570 is mounted to the obturator 1560 intermediate the proximal and distal ends. In the illustrative example of FIG. 60, the connector 1570 is a male Luer-type fitting. The obturator 1560 is receivable in the drill tube 1510 by inserting the distal end 1566 of the obturator 1560 into the proximal end 1514 of the drill tube 1510 and advancing the obturator until the connectors engage. The obturator 1560 and drill tube 1510 are locked together by rotating the connectors relative to one another. The drill tube 1510 and obturator 1560 have drilling tips 1526, 1572 that align when the obturator is inserted into the drill tube and locked. For example, the drilling tips 1526, 1572 may be formed by assembling the obturator 1560 and drill tube 1510, locking them together, and then grinding the cutting tips on the drill tube 1510 and obturator 1560 simultaneously. In the illustrative example of FIG. 60, when the drill tube 1510 and obturator 1560 are assembled, the drilling tips 1526, 1572 form a diamond drill tip having primary bevels 1580 formed on opposed first and second sides and secondary bevels 1582 to provide relief and improve cutting. The outer diameter of the drill tube 1510 and the counterbore 1333 of the opening 1332 are sized so that the drill tube 1510 may be received in the counterbore 1333.

Figure 61:
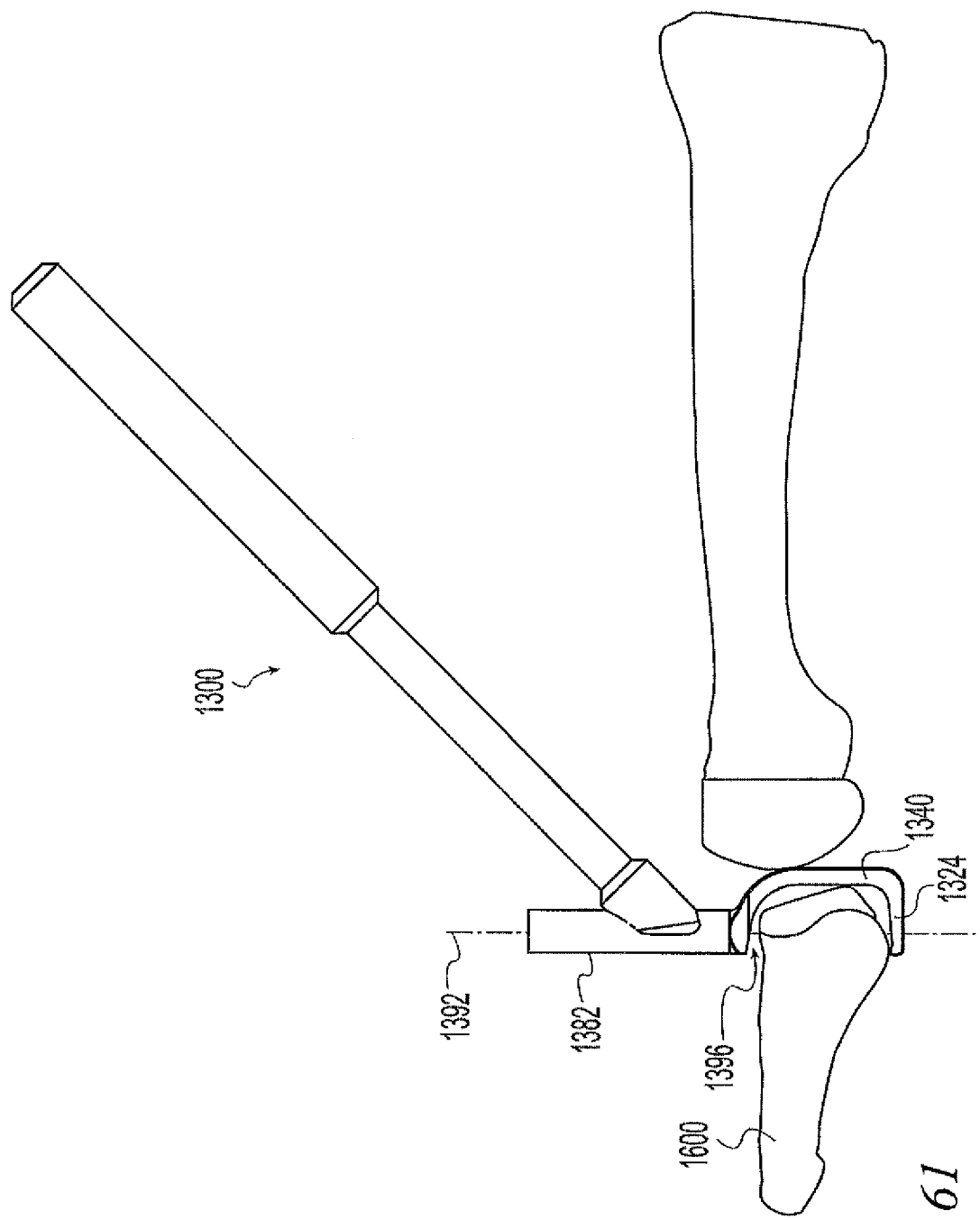
FIGS. 61-70 are side elevation views illustrating the suture passer of FIG. 2 in use.

FIGS. 61-70 illustrate the illustrative suture passer 200 of FIGS. 52-59 and the illustrative drill assembly of FIG. 60 in use to form a bone tunnel and load a graft into the tunnel. In FIG. 61, the suture retriever 1300 has been positioned adjacent a bone 1600 with the foot 1324 on one side of the bone with the opening 1332 aligned with a desired exit location for a bone tunnel and the guide axis 1392 aligned with the desired tunnel axis. By viewing through the tube 1382 along the axis 1392, the location of the tunnel entrance can be visualized. The retriever 1300 is shown positioned adjacent a phalanx bone with the extension 1340 in the joint space and the guide positioned to form a tunnel from dorsal to plantar through the proximal phalanx. The guide may be positioned at any location around the joint to create bone tunnels at any desired location in the phalanx or the metatarsus. For example, the guide may be positioned to create tunnels for repairing or replacing a proper collateral ligament, accessory plantar ligament, plantar plate, or other structure in or around the joint.

Figure 62:
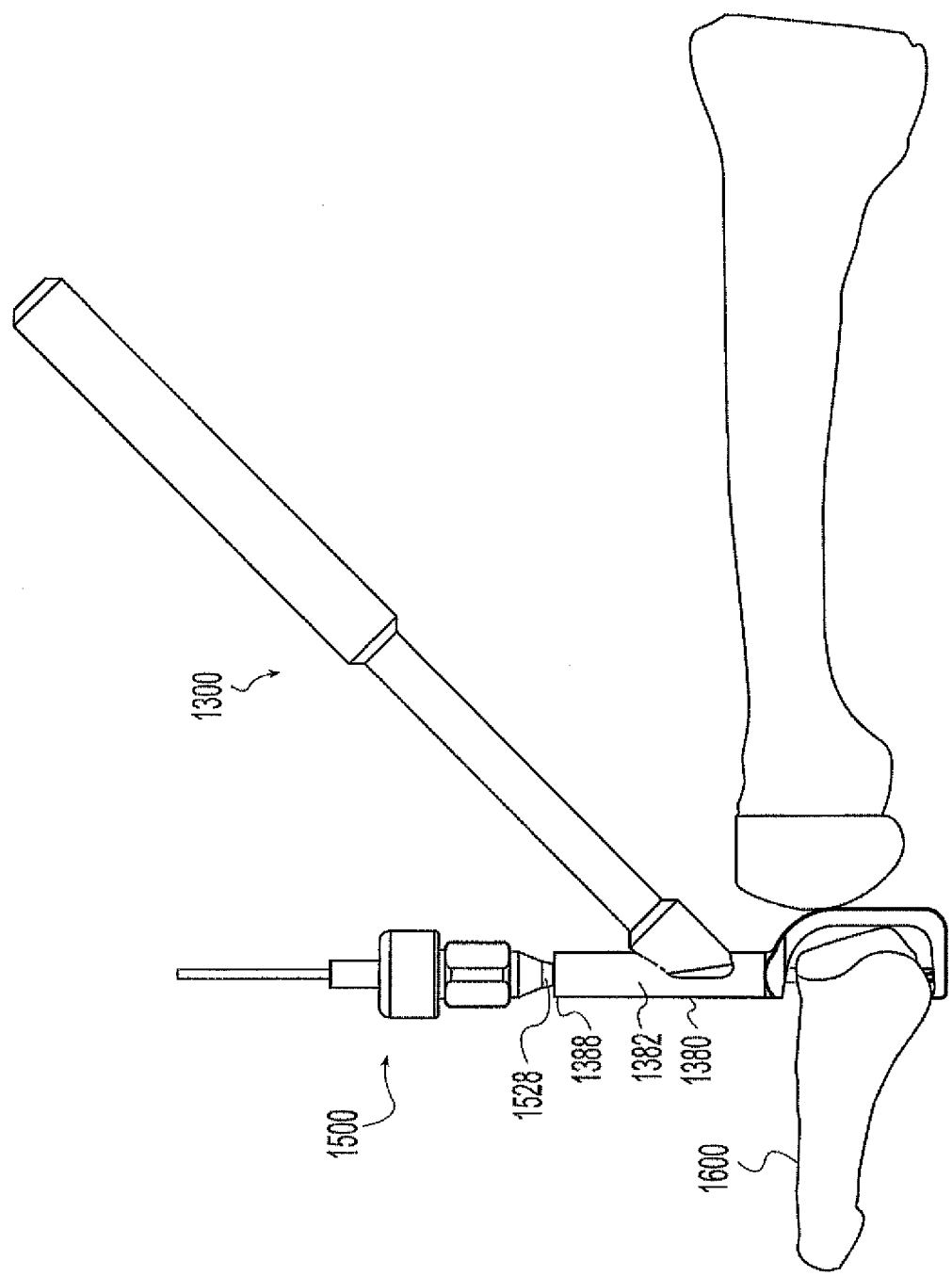

In FIG. 62, the drill assembly 1500 has been guided via the inner surface 1384 of the guide tube 1382 to form a tunnel through the bone 1600. Stop 1528 abuts the proximal end 1388 of the guide 1380 to limit the drilling depth. In the illustrative examples of FIGS. 52-60, the stop 1528 abuts the proximal end 1388 when the drill tube 1510 is received in the counterbore 1333. Alternatively, the opening in the foot may be sized to engage the tip of the drill to limit the depth or a depth stop may be omitted.

Figure 63:
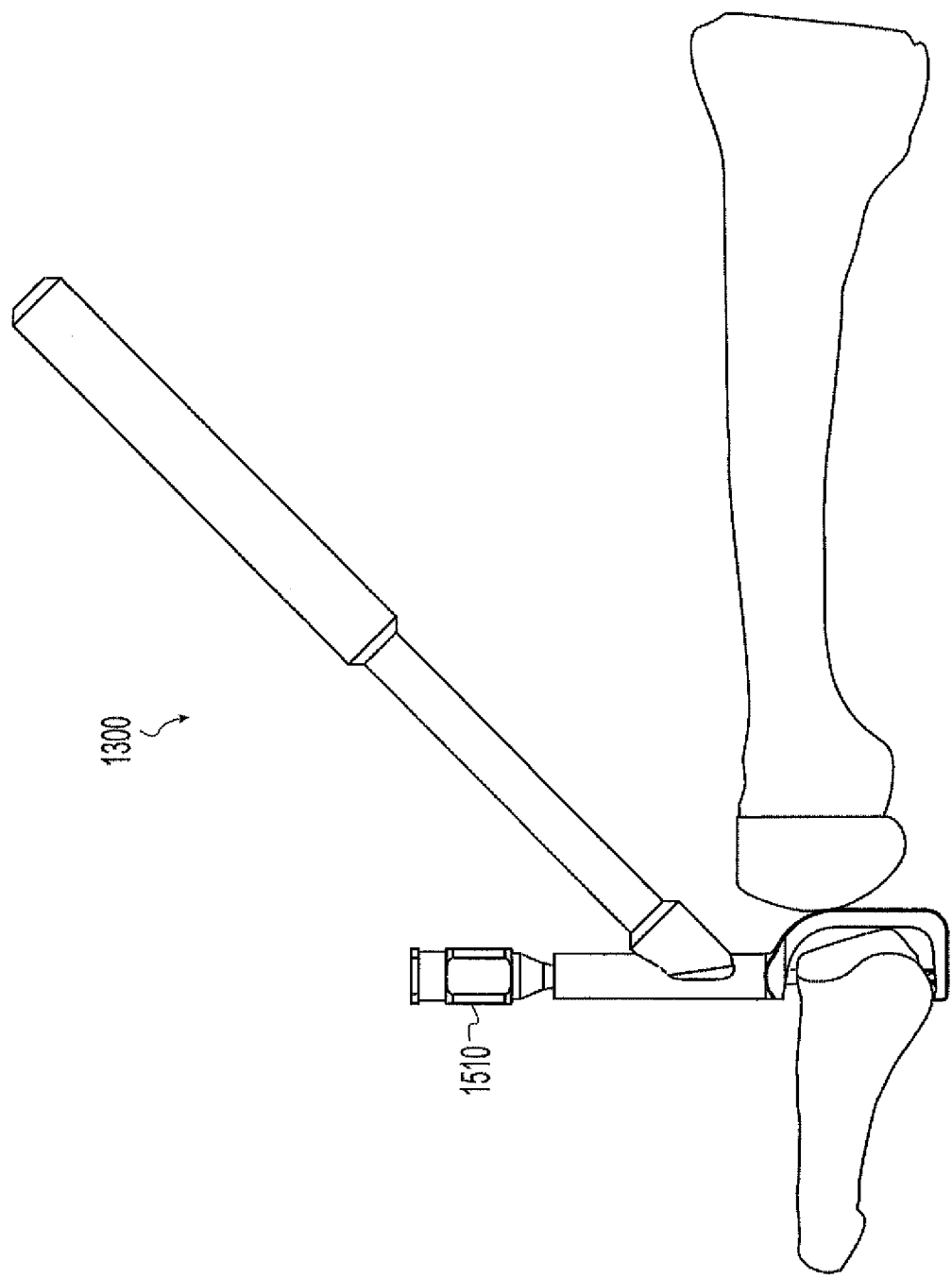

In FIG. 63, the obturator 1560 has been removed leaving the drill tube 1510 in place. Optionally, the drill tube 1510 could be removed or a one-piece drill could be substituted for the drill assembly 1500. However, by leaving the drill tube 1510 in place, the drill tube 1510 locks the retriever 1300 in place on the bone, provides guidance for the suture, and provides a smooth passage for the suture.

Figure 64:
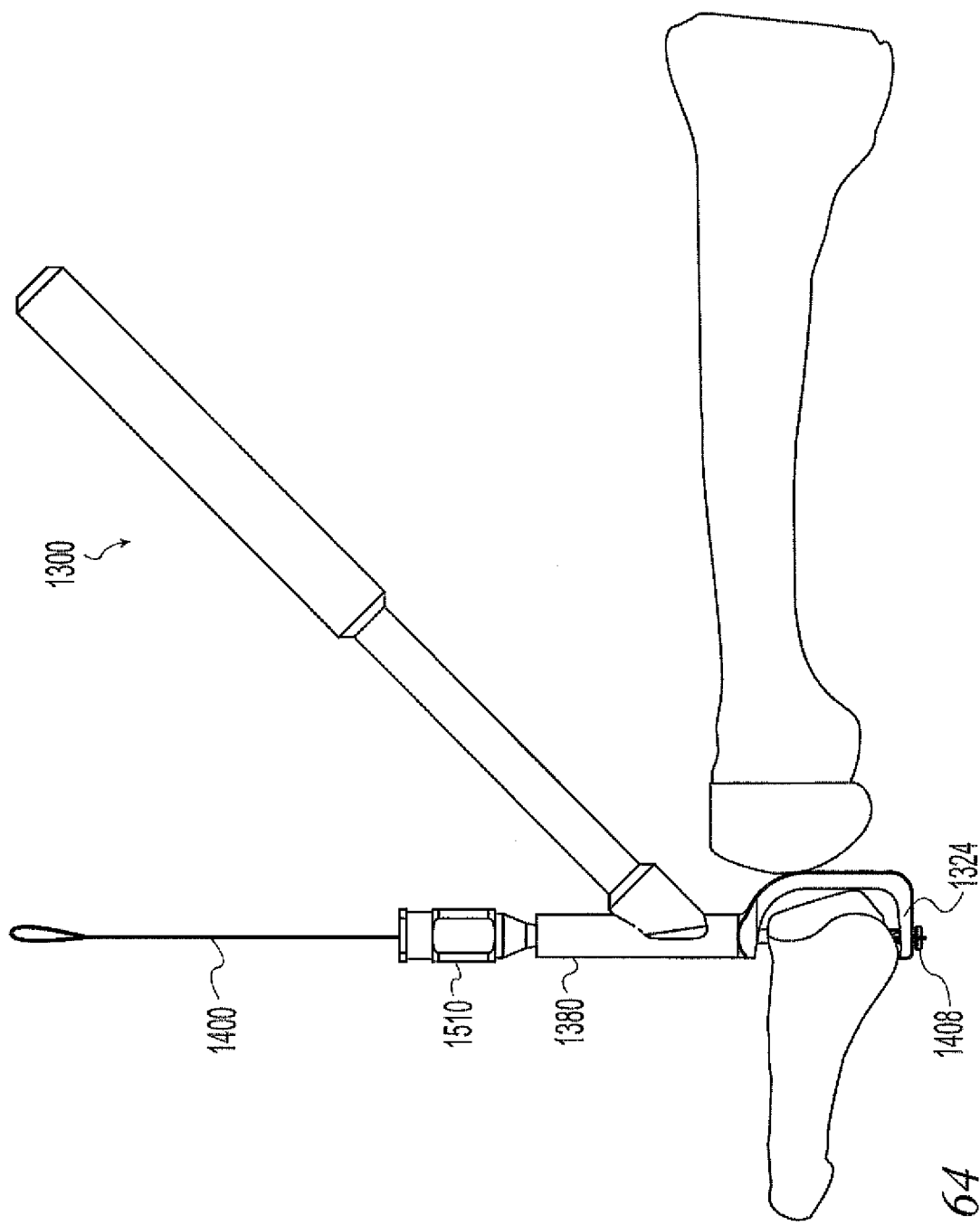

In FIG. 64, the suture 1400 has been inserted until the stopper 1406 engages the receiver 1320. In the example of FIG. 64, the pledget 1408 has been forced through the opening 1332 in the foot 1324.

Figure 65:
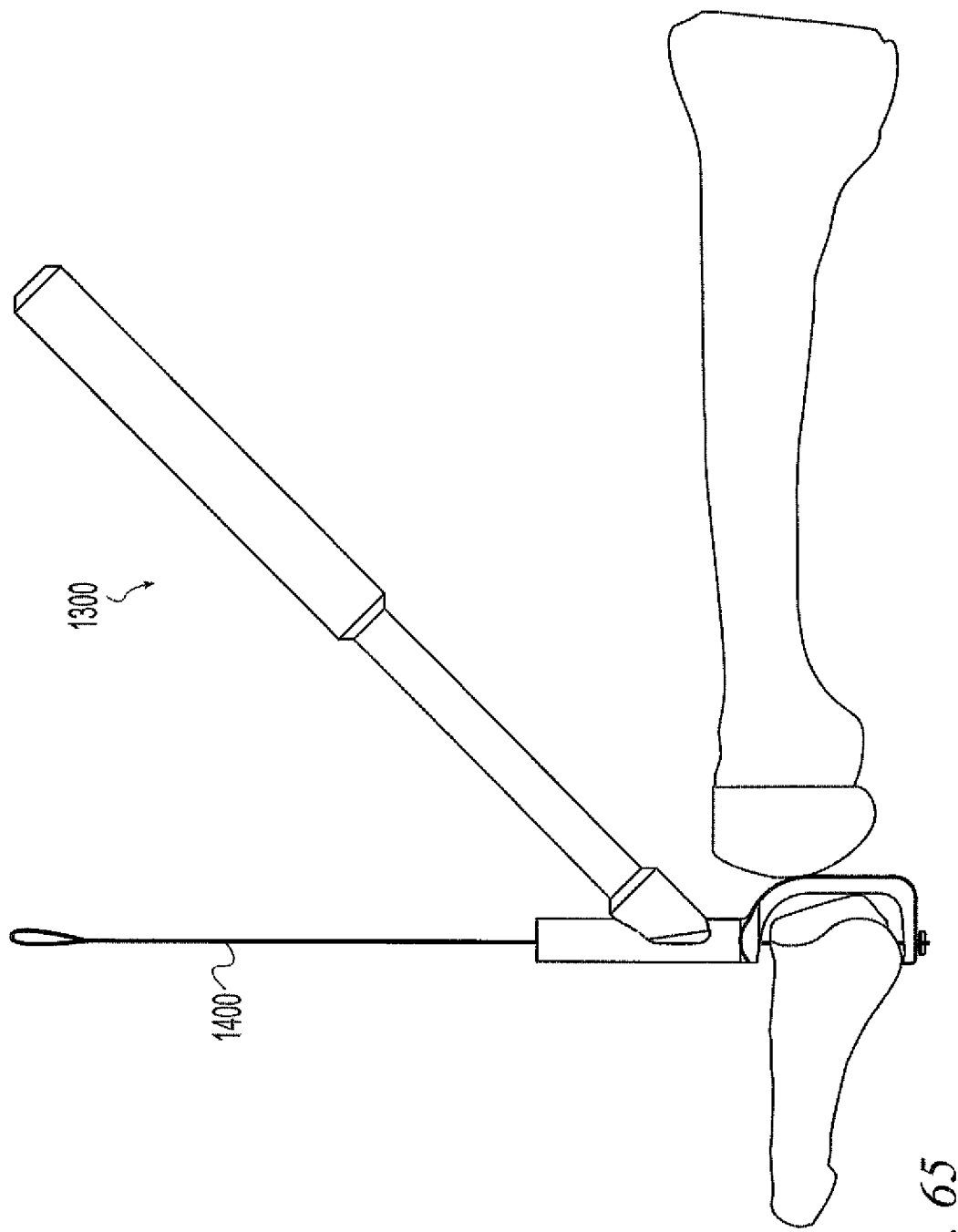

In FIG. 65, the drill tube 1510 has been removed leaving the suture 1400 in place.

Figure 66:
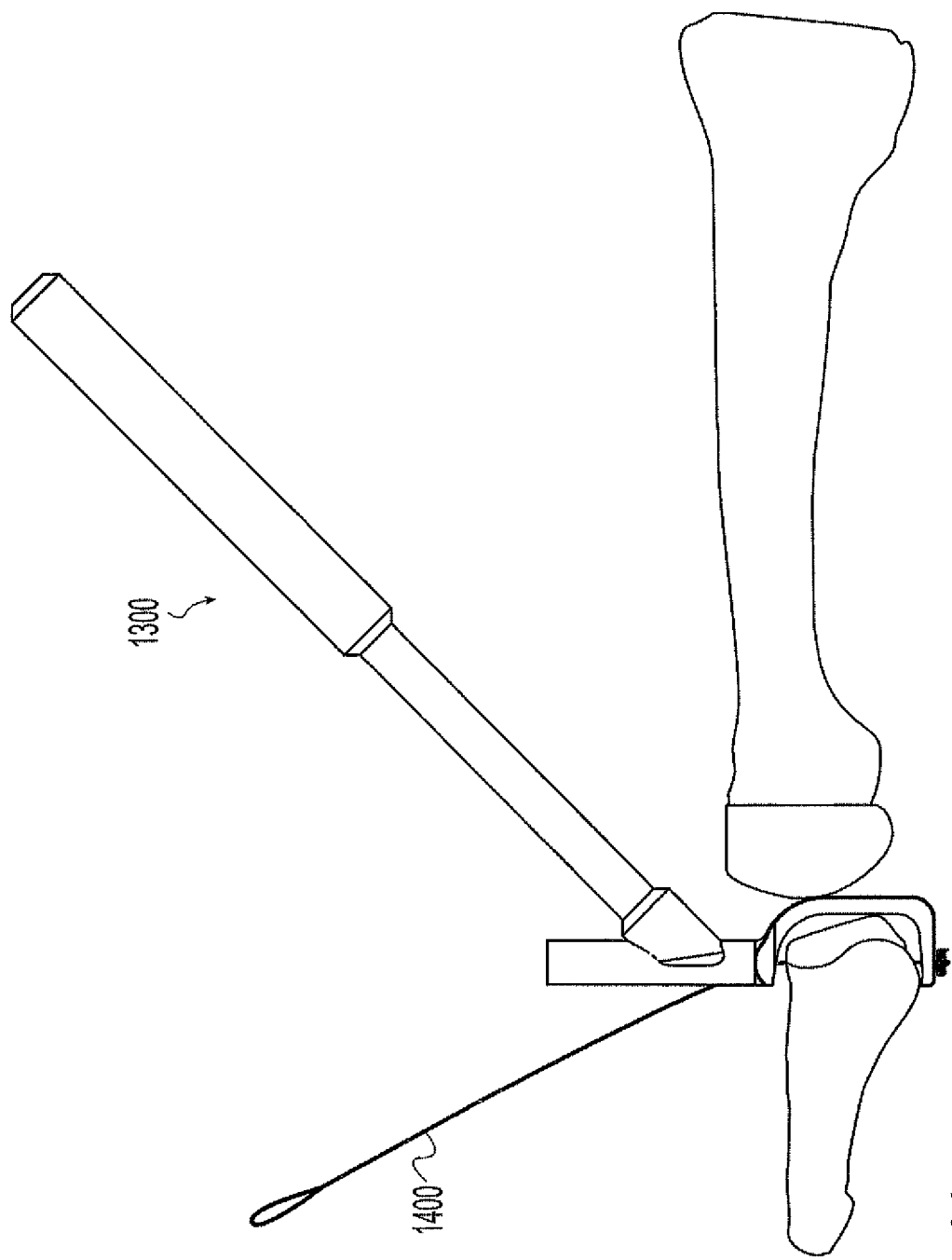

In FIG. 66, the suture 1400 has been pulled through the slot 1394 to free the proximal end 1402 from the guide tube 1382. The slot 1394 simplifies withdrawing the retriever 1300 from the surgical site. However, the slot 1394 may be omitted and the proximal end 1402 of the suture threaded through the guide tube 1382 as the retriever 1300 is withdrawn.

Figure 67:
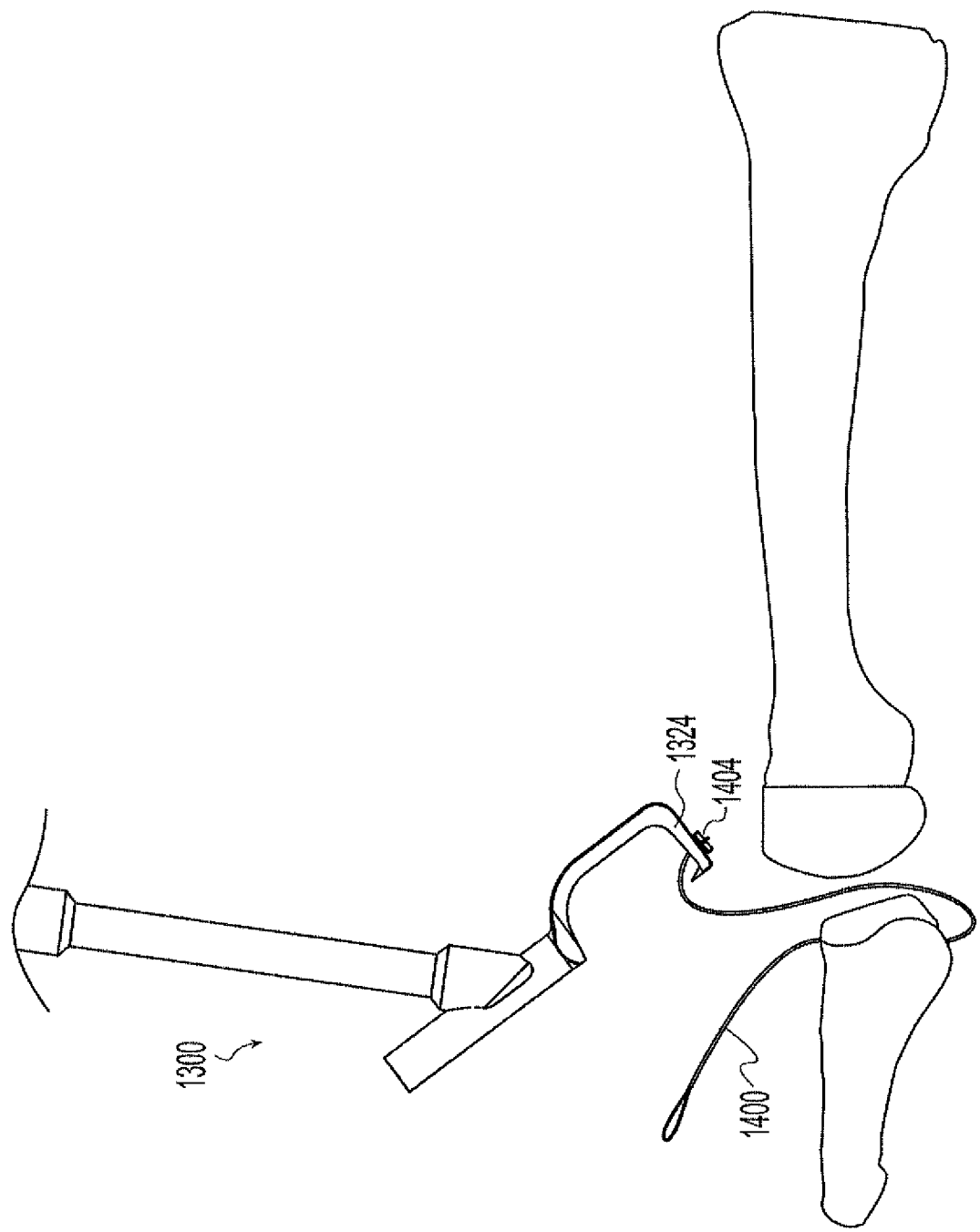

In FIG. 67, the retriever 1300 has been withdrawn from the surgical site taking the distal end 1404 of the suture 1400 with it and thereby further advancing the suture 1400 into the bone tunnel. The suture 1400 may be left attached to the retriever 1300 or it may be separated from the retriever by pulling the distal end 1404 back through the foot or cutting off the distal end 1404 of the suture.

Figure 68:
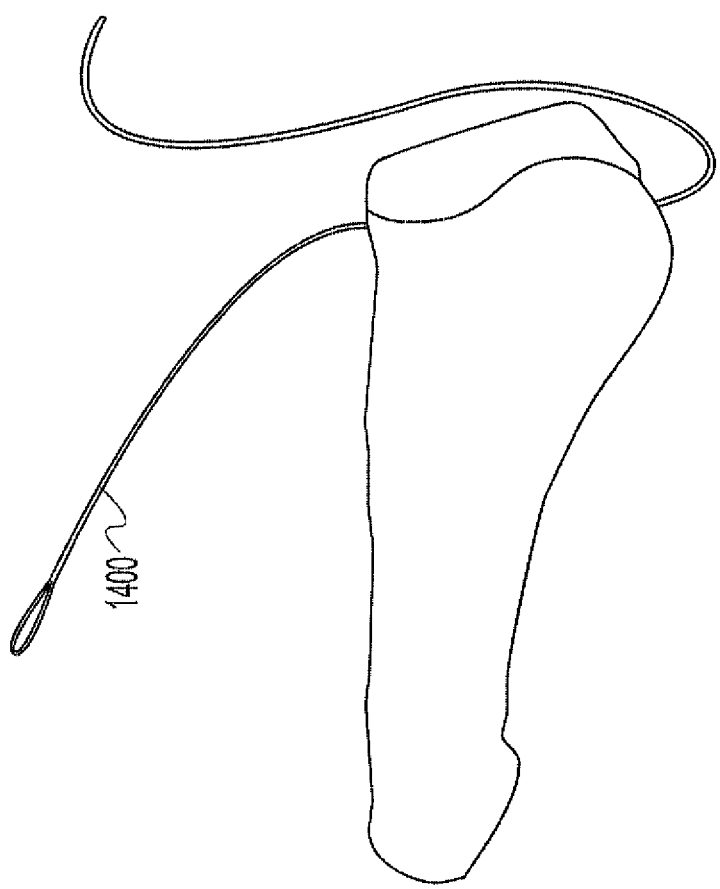

In FIG. 68, the distal end 1404 of the suture 1400 has been cut off to free it from the retriever 1300 and the retriever 1300 removed.

Figure 69:
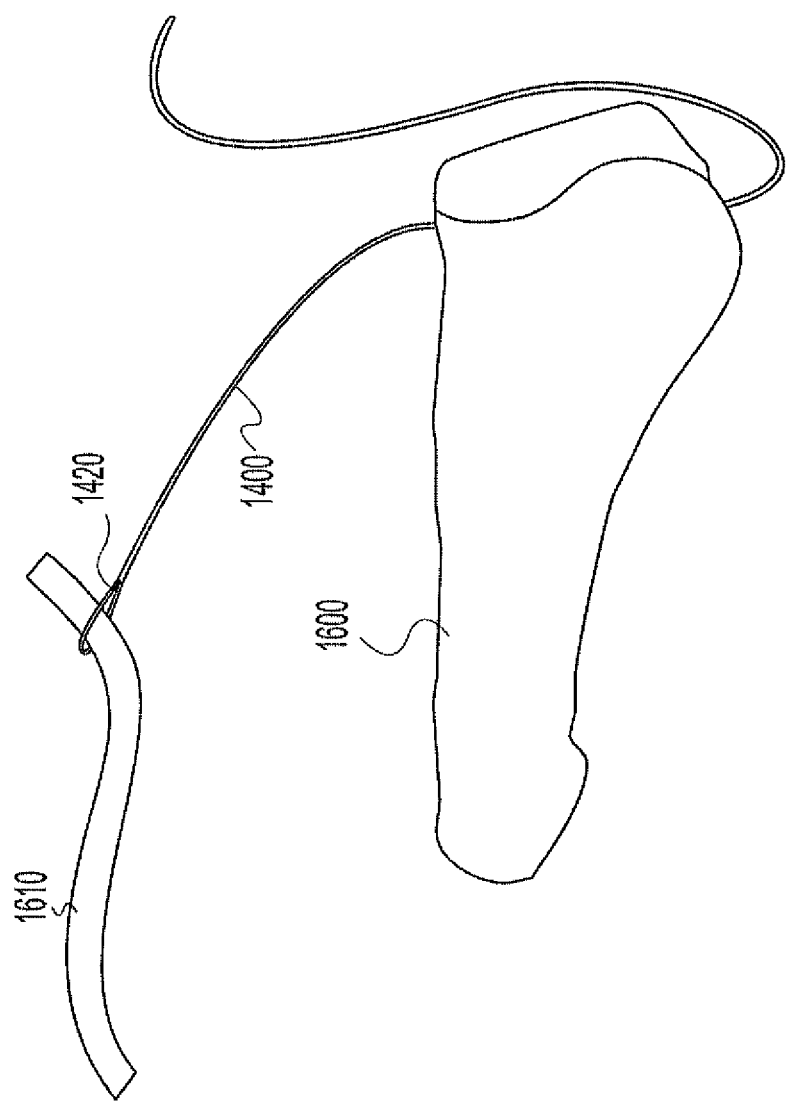

In FIG. 69, a graft 1610 has been engaged with the proximal end 1402 of the suture 1400 by threading it through the loop 1420. Alternatively, a graft or any other material may be attached to the distal end for pulling in the opposite direction. In addition to being used to retrieve a graft, the suture 1400 may be used as a definitive suture in a repair or reconstruction. Also, the suture 1400 may be used to pull another graft retrieval strand such as, for example, a larger or more flexible strand.

Figure 70:
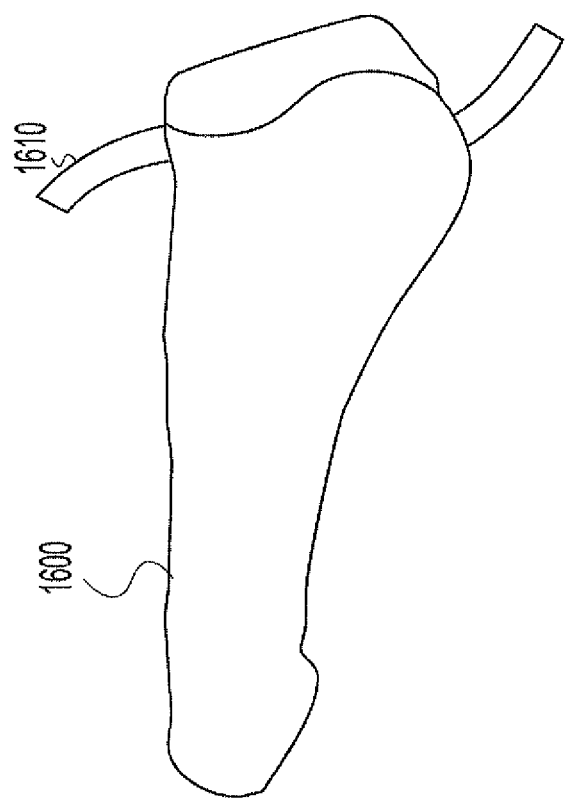

In FIG. 70, the suture 1400 has been pulled to advance it through the bone tunnel and pull the graft 1610 along with it to position the graft 1610 in the bone tunnel and the suture 1400 has been removed.

Figure 71:
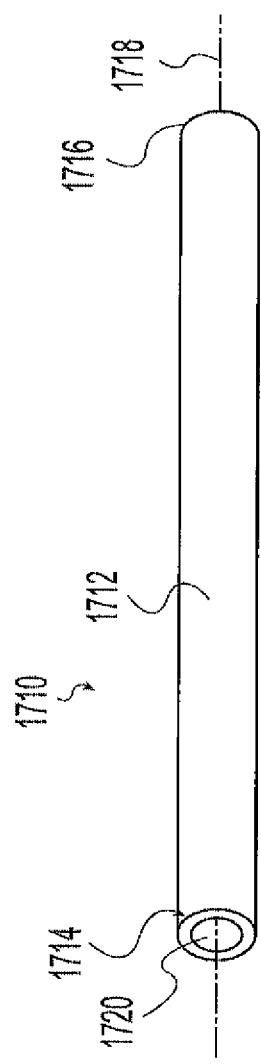
FIG. 71 is a perspective view of an optional component useable with the suture passers of FIG. 51 and FIG. 52.

FIG. 71 illustrates a suture inserter 1710 having an elongated body 1712 with a proximal end 1714, a distal end 1716, and a longitudinal axis 1718. The suture inserter 1710 may be used to advance the suture 1400 into engagement with the receiver 1320 by pushing the stopper 1406. The suture inserter 1710 or the suture inserter 1710 in combination with the suture may have a higher columnar strength than the suture alone and facilitate advancing the suture 1400. In the illustrative example, the suture inserter includes a longitudinal passage 1720 for receiving the suture 1400 with the stopper 1406 adjacent the distal end 1716.

Figure 72:
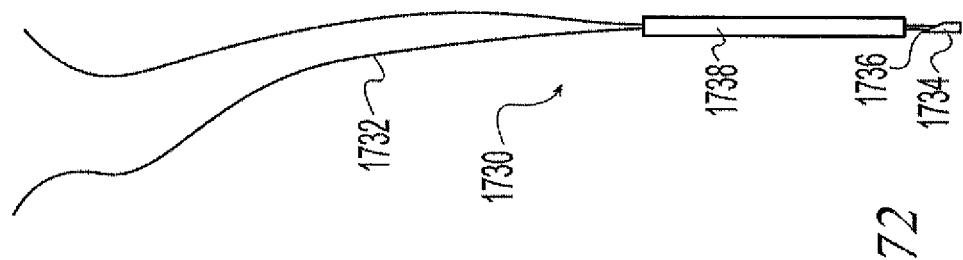
FIG. 72 is a side elevation view of an alternative suture useable with the suture passers of FIG. 51 and FIG. 52.

FIG. 72 illustrates a suture 1730 having two strands 1732 joined to a stopper 1734 having a proximal end 1736 formed at an angle to the suture strands 1732 so that the proximal end 1736 will hook onto the retriever 1320. The suture 1730 is also shown with the suture inserter 1710 of FIG. 51 useable to push the stopper 1734. For use in passing a graft, the suture strands 1732 may be tied to form a loop, stitched to the graft, wrapped around the graft, or otherwise connected to the graft. The suture ends may also be used directly to attach hard or soft tissue, implants, or other materials at a surgical site. The suture strands may also be used directly as a ligament or tendon replacement.

Figure 73:
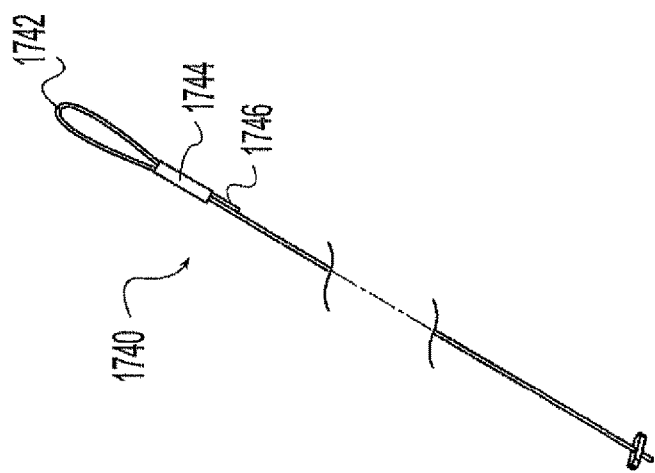
FIG. 73 is a side elevation view of an alternative suture useable with the suture passers of FIG. 51 and FIG. 52.
Figure 78:
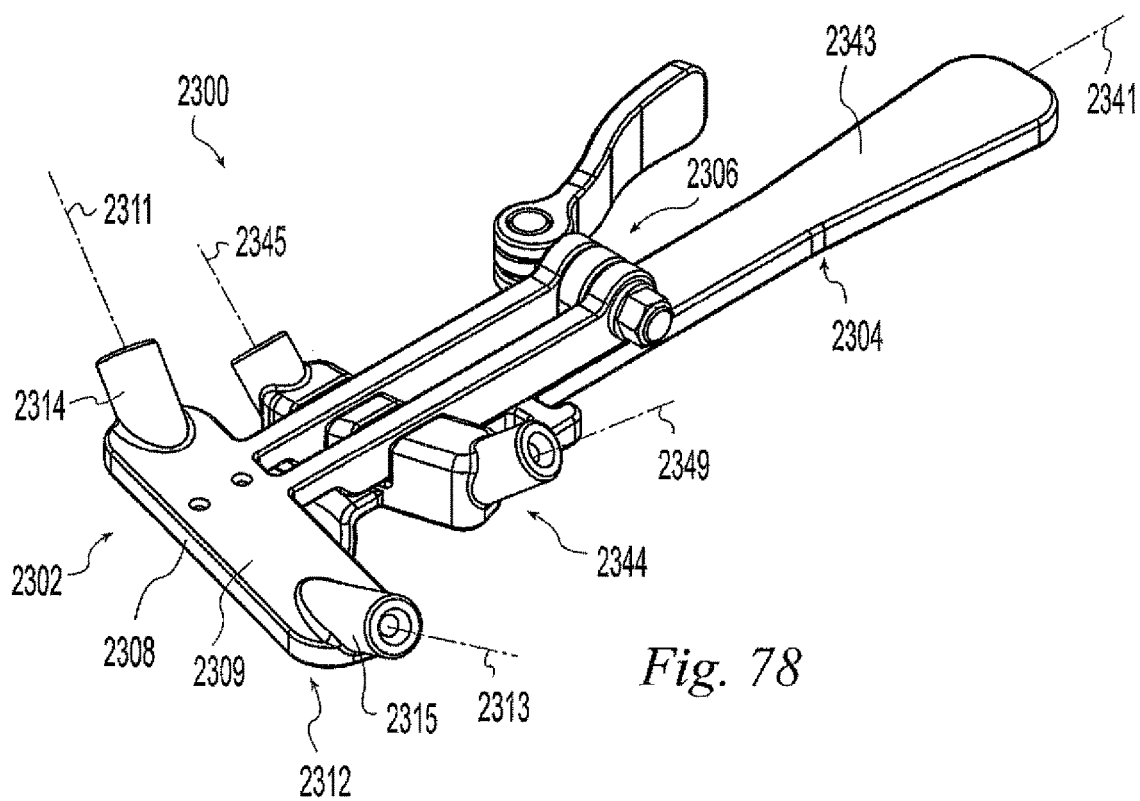
FIG. 78 is a perspective view of an illustrative example of a guide according to the present invention.
Figure 79:
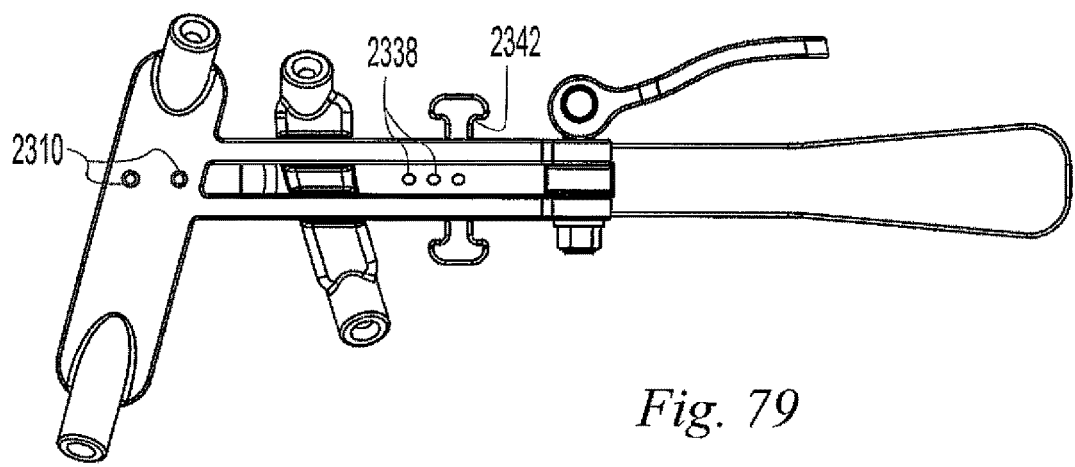
FIG. 79 is a top plan view of the guide of FIG. 78.
Figure 80:
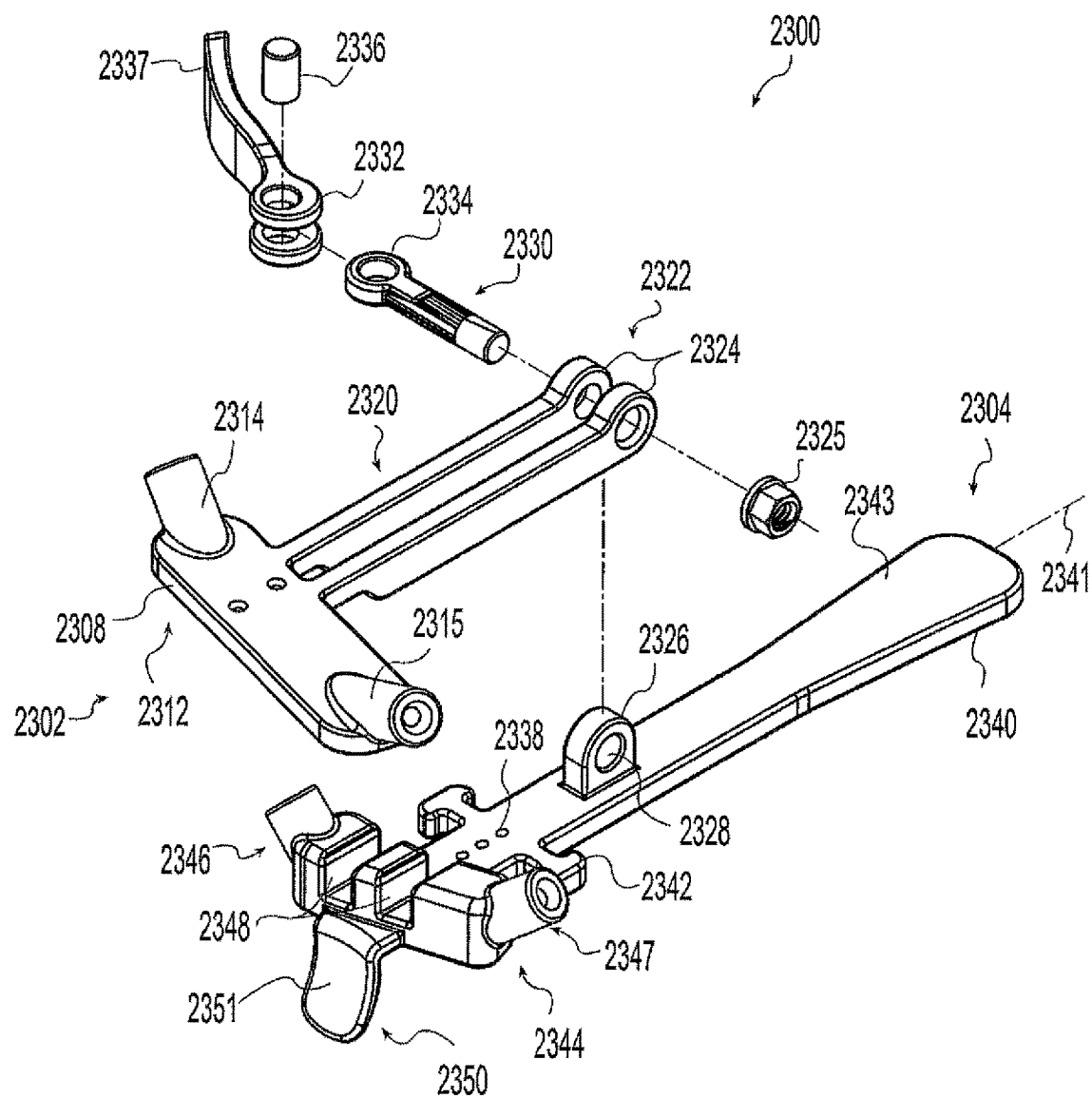
FIG. 80 is an exploded perspective view of the guide of FIG. 78.
Figure 81:
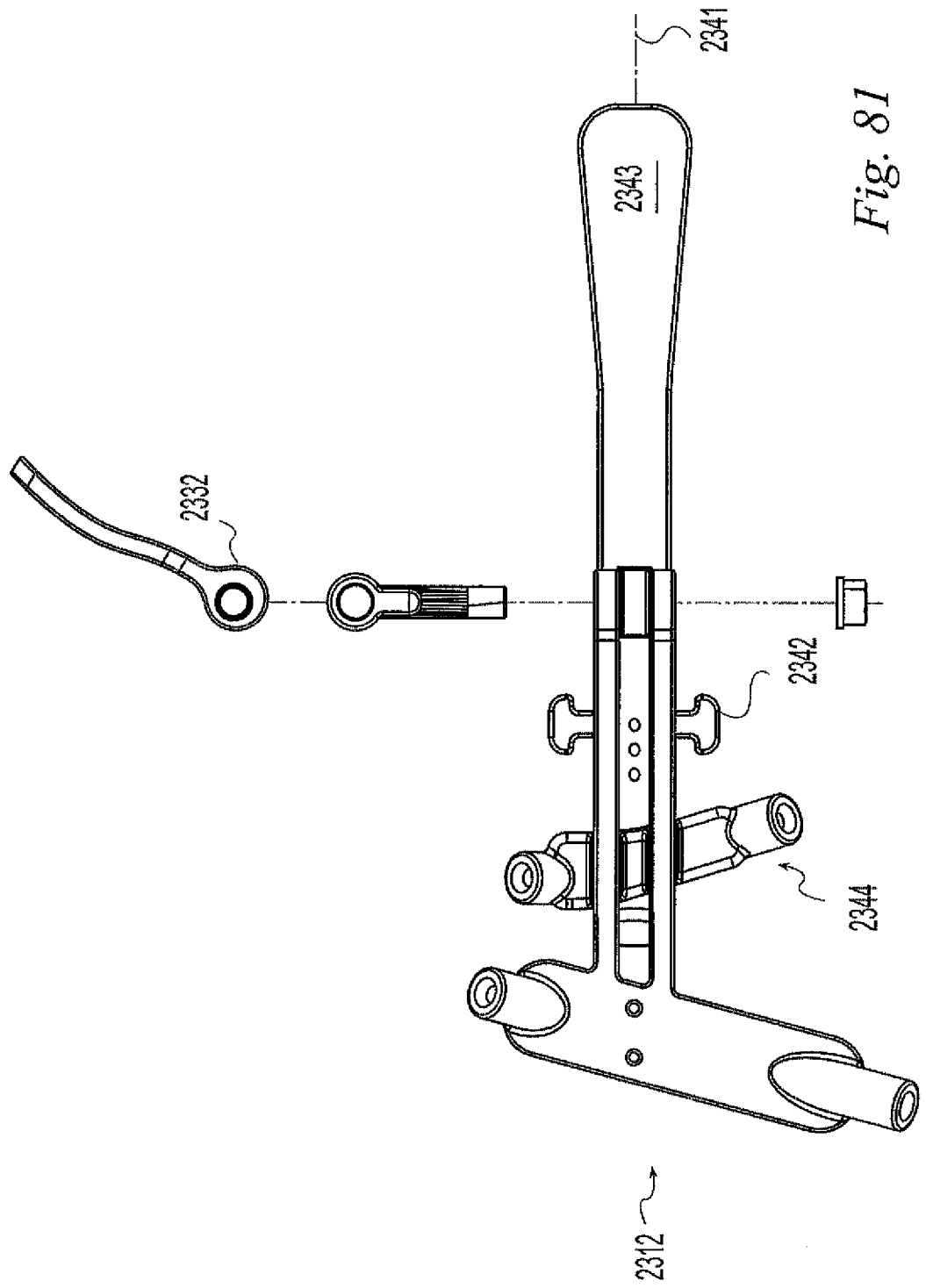
FIG. 81 is an exploded top plan view of the guide of FIG. 78.

FIG. 73 illustrates a suture 1740 having a loop 1742 retained by swaging a ferrule 1744 to retain the proximal end 1746 of the suture 1740.

Figure 74:
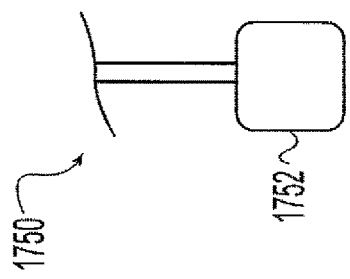
FIG. 74 is a side elevation view of an alternative stopper useable with the sutures of FIG. 51 and FIG. 52.

FIG. 74 illustrates a suture 1750 having a stopper 1752 formed of a block of resilient material such as, for example, a closed cell foam.

Figure 75:
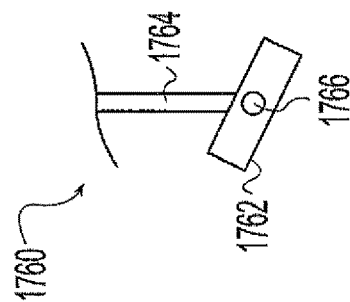
FIG. 75 is a side elevation view of an alternative stopper useable with the sutures of FIG. 51 and FIG. 52.

FIG. 75 illustrates a suture 1760 having a stopper 1762 joined to a strand 1764 at a pivot 1766 so that the stopper 1762 can toggle between a receiving position generally more parallel to the strand 1764 and a retaining position generally more perpendicular to the strand 1764.

Figures 52, 53:
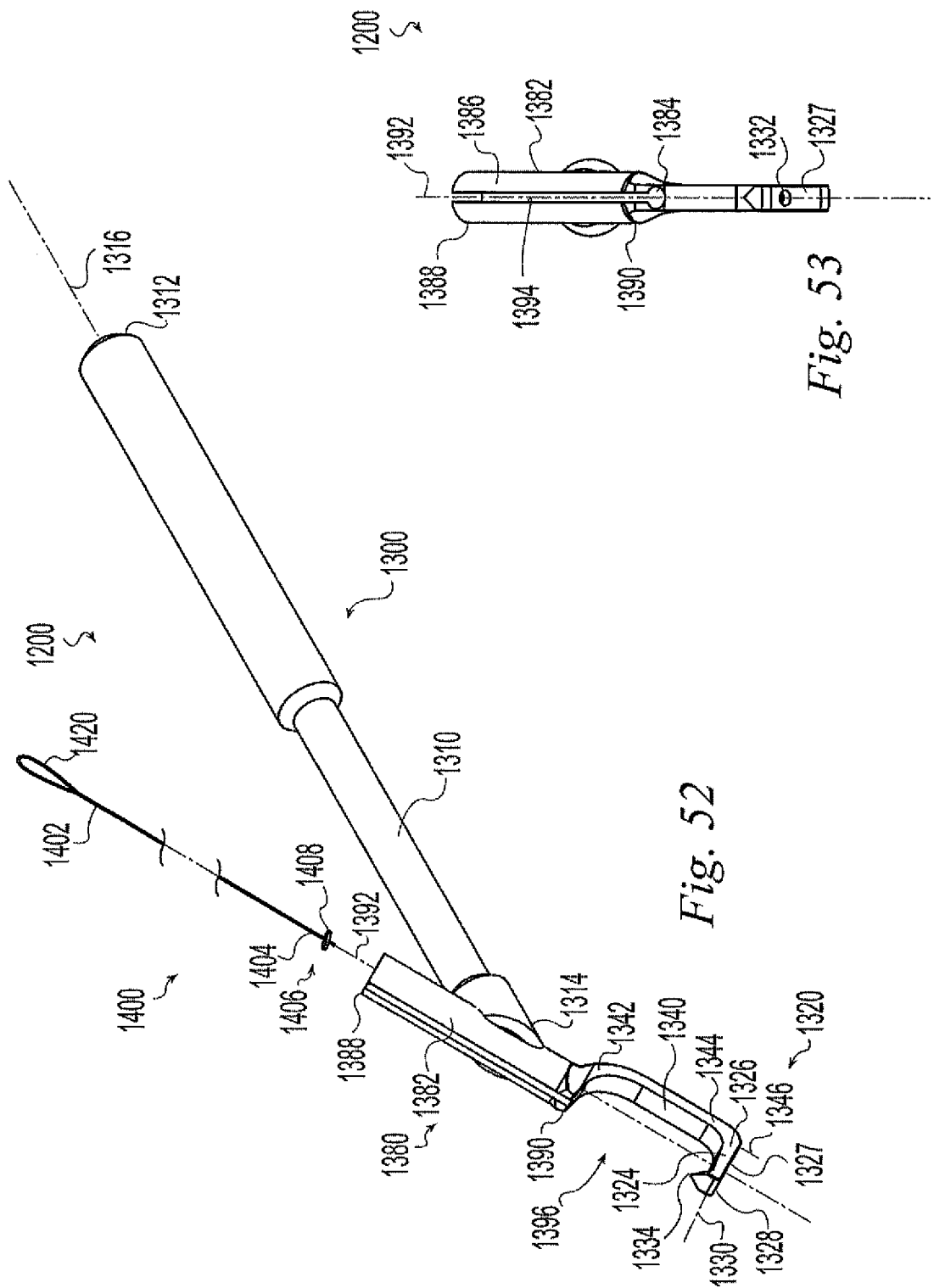
FIG. 52 is an exploded perspective view of an illustrative example of a suture passer according to the present invention.
FIG. 53 is a front elevation view of a component of the suture passer of FIG. 52.
Figure 54:
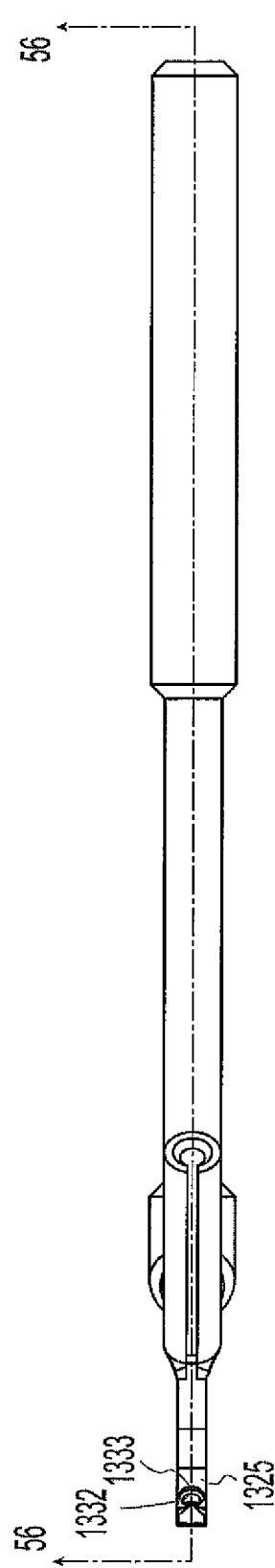
FIG. 54 is a top plan view of the component of FIG. 53.
Figure 55:
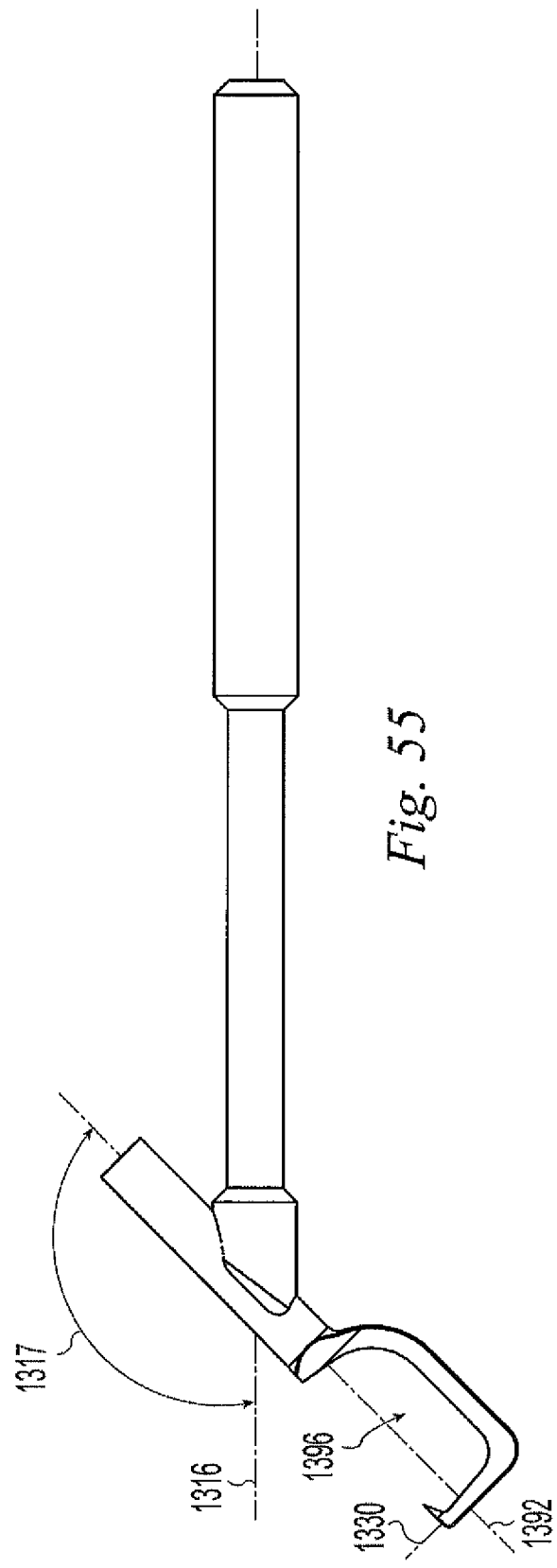
FIG. 55 is a side elevation view of the component of FIG. 53.

FIG. 76 illustrates an alternative foot 1770 to the foot 1324 of FIG. 52. The foot 1770 has first and second opposable jaws 1772, 1774. The first jaw 1772 is mounted for rotation relative to the second jaw about a pivot 1776. The jaws 1772, 1774 are moveable between a first closed, position (shown) in which the jaw faces are adjacent one another and a second, open position (not shown) in which the first jaw 1772 is pivoted away from the second jaw 1774 to create a space between the jaws 1772, 1774 for receiving a suture 1778. The jaws may be closed on the suture 1778 to retain the suture and allow it to be retrieved. Any suitable mechanism may be used to move the first jaw relative to the second jaw. For example, a control cable 1779 may be mounted in the foot and moveable by a remote actuator to move the first jaw 1772 between the first and second positions.

FIG. 77 illustrates an alternative foot 1780 to the foot 1324 of FIG. 52. The foot 1780 has moveable member 1782 mounted for movement relative to an opening 1784 between a first position in which the opening is not blocked and a suture 1786 may be received in the opening and a second position in which the member 1782 and edge of the opening 1784 grasp the suture. Any suitable mechanism may be used to move the member 1782. For example, a control cable 1788 may be mounted in the foot and moveable by a remote actuator to move the member 1782 between the first and second positions.

The illustrative examples of FIGS. 51-77 have shown the suture passer 1200 in use to pass a suture used to pull a graft into a tunnel. However, a suture passed by the suture passer may be used in any way that sutures are known to be used. For example a suture may be used as a shuttle for pulling another suture, graft, or anything else from bottom to top rather than from top to bottom as depicted in the illustrative examples. Single strands, double strands, or any number of strands may be passed. Likewise one or more loops may be passed. Any of these may be used as a definitive suture in a repair or reconstruction, as a shuttle for pulling another material into a desired position, or for any other purpose.

FIGS. 78-86 illustrate an exemplary guide 2300 for guiding a cutter to cut a bone. In this illustrative example, the guide 2300 is configured as a drill guide to guide a drill, punch, pin, broach or the like to form holes in the bones adjacent the second MTP joint of the right human foot. The drill guide 2300 includes a pair of plate-like members 2302, 2304 joined at a hinge 2306 allowing a single degree of freedom such that the members may be pivoted between a first position and a second position. The members include a plurality of fixation holes for receiving fixation devices, e.g. fixation pins or screws, to secure the members to underlying bones and guide holes to guide the formation of tunnels in the underlying bones to facilitate soft tissue repair, replacement, and/or augmentation around the joint. The first member 2302 is configured to overlie the metatarsus and the second member 2304 is configured to overly the phalanx.

The first member 2302 includes a planar top surface 2309, a first end 2308 having fixation holes 2310, and a metatarsal guide portion 2312. The metatarsal guide portion 2312 has a feature for guiding a cutter. In the illustrative example of FIGS. 78-86, the metatarsal guide portion 2312 includes medial and lateral spaced apart, hollow, tubular extensions 2314, 2315 each projecting upwardly and outwardly from the top surface 2309 and configured as a drill guide able to guide a drill, punch, broach, pin or the like. The tubular extensions 2314, 2315 are oriented so that their axes 2311, 2313 intersect below the metatarsal guide portion 2312. A mounting yoke 2320 having opposed spaced apart arms extends from the first end 2308 to a second end 2322 defining a pair of eyelets 2324 which straddle a block 2326 mounted on the second member 2304. The block 2326 has a hole 2328 aligned with the eyelets 2324. A bolt 2330 and nut 2325 join the eyelets 2324 and block 2326. A locking cam 2332 is pinned to the head 2334 of the bolt 2330 for relative rotation about a pin 2336 and includes a lever 2337 extending from the cam for rotating the cam 2332 between a locked and unlocked position. The bolt 2330 and locking cam 2332 are operable to press the eyelets 2324 together against the block 2326 to frictionally lock the members 2302, 2304 in relative angular relationship.

The second member 2304 includes an elongated handle 2340 having a longitudinal axis 2341, a planar top surface 2343, fixation holes 2338 and a phalangeal guide portion 2344. The phalangeal guide portion 2344 has a feature for guiding a cutter. In the illustrative example of FIGS. 78-86, the phalangeal guide portion 2344 includes medial and lateral spaced apart, hollow, tubular extensions 2346, 2347 each projecting upwardly and configured as a drill guide able to guide a drill, punch, broach, pin or the like along axes 2345, 2349. The phalangeal guide portion 2344 includes a pair of grooves 2348 for receiving the yoke 2320 of the first member to increase the relative positional accuracy and stability of the members relative to one another when the members are locked in the second coaxial position. The second member 2304 further includes a head referencing member 2350 having a reference surface 2351 for engaging an anatomic landmark. In the illustrative example of FIGS. 78-86, the head referencing member 2350 has a concave spherical surface able to engage the articular surface of the metatarsal head. Opposite the concave surface is a convex back surface able to engage the articular surface of the phalangeal head. The second member further includes a pair of oppositely, laterally extending bosses 2342 for receiving a band to secure the guide 2300 to the phalanx.

Figure 82:
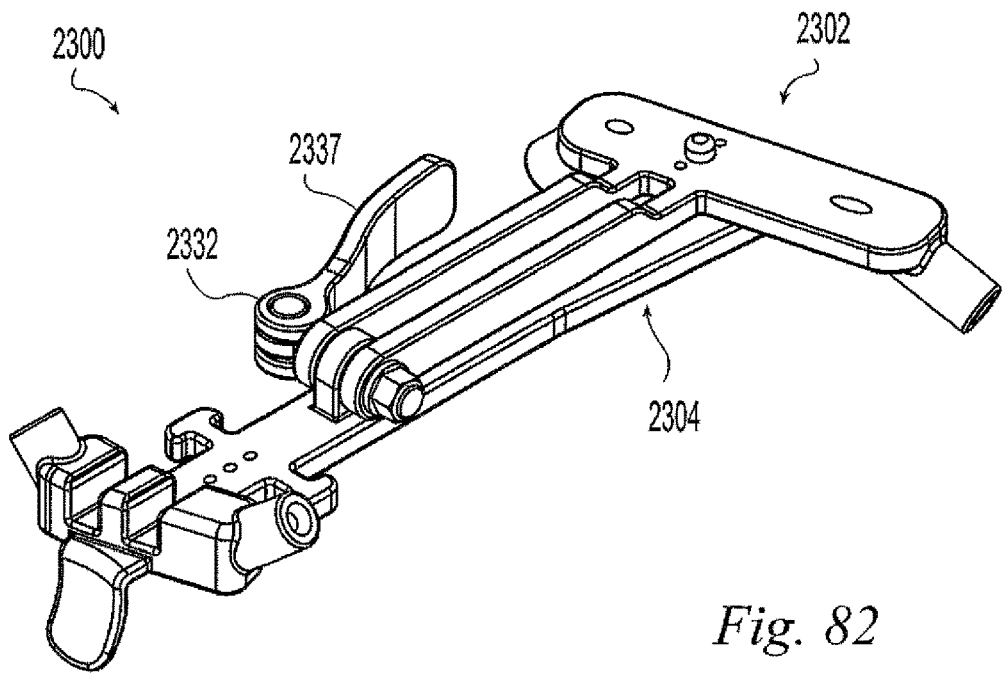
FIG. 82 is a perspective view of the guide of FIG. 78 showing a position of the guide.
Figure 83:
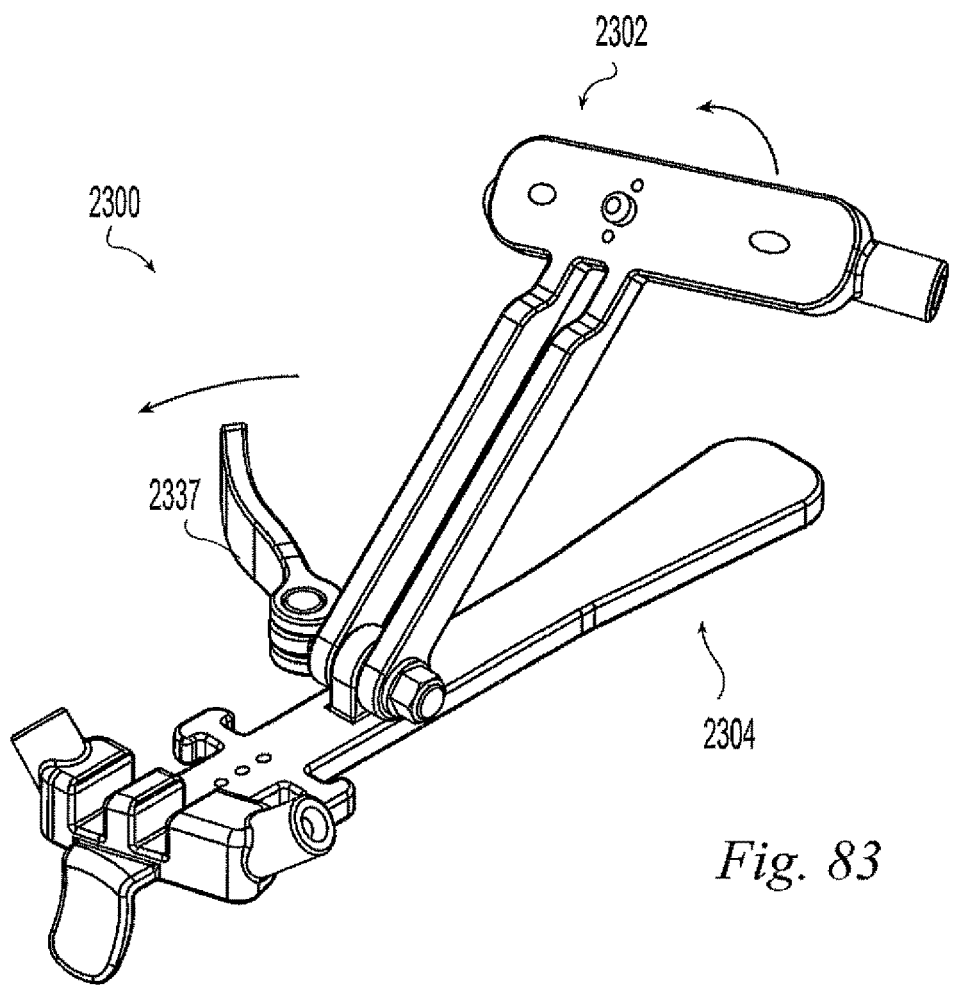
FIG. 83 is a perspective view of the guide of FIG. 78 showing a position of the guide.
Figure 84:
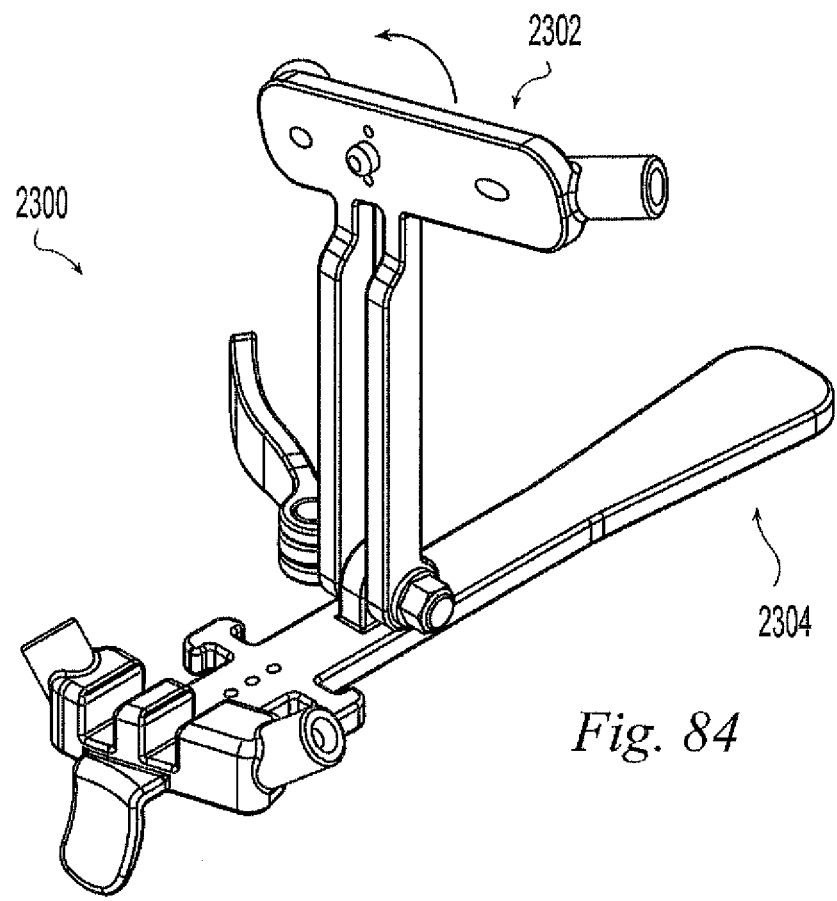
FIG. 84 is a perspective view of the guide of FIG. 78 showing a position of the guide.
Figure 85:
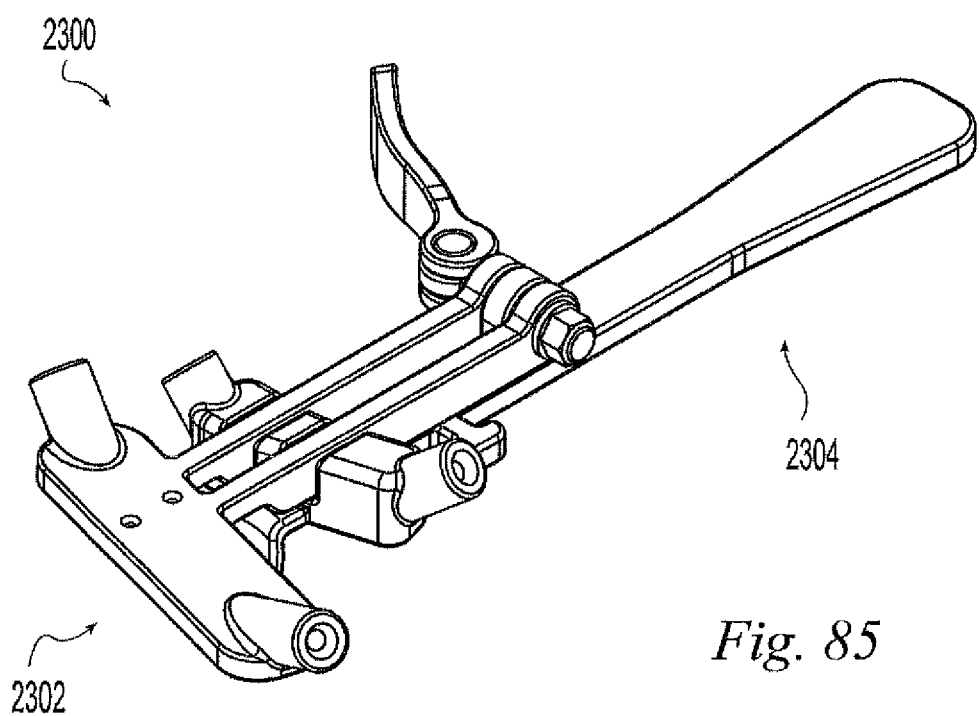
FIG. 85 is a perspective view of the guide of FIG. 78 showing a position of the guide.
Figure 86:
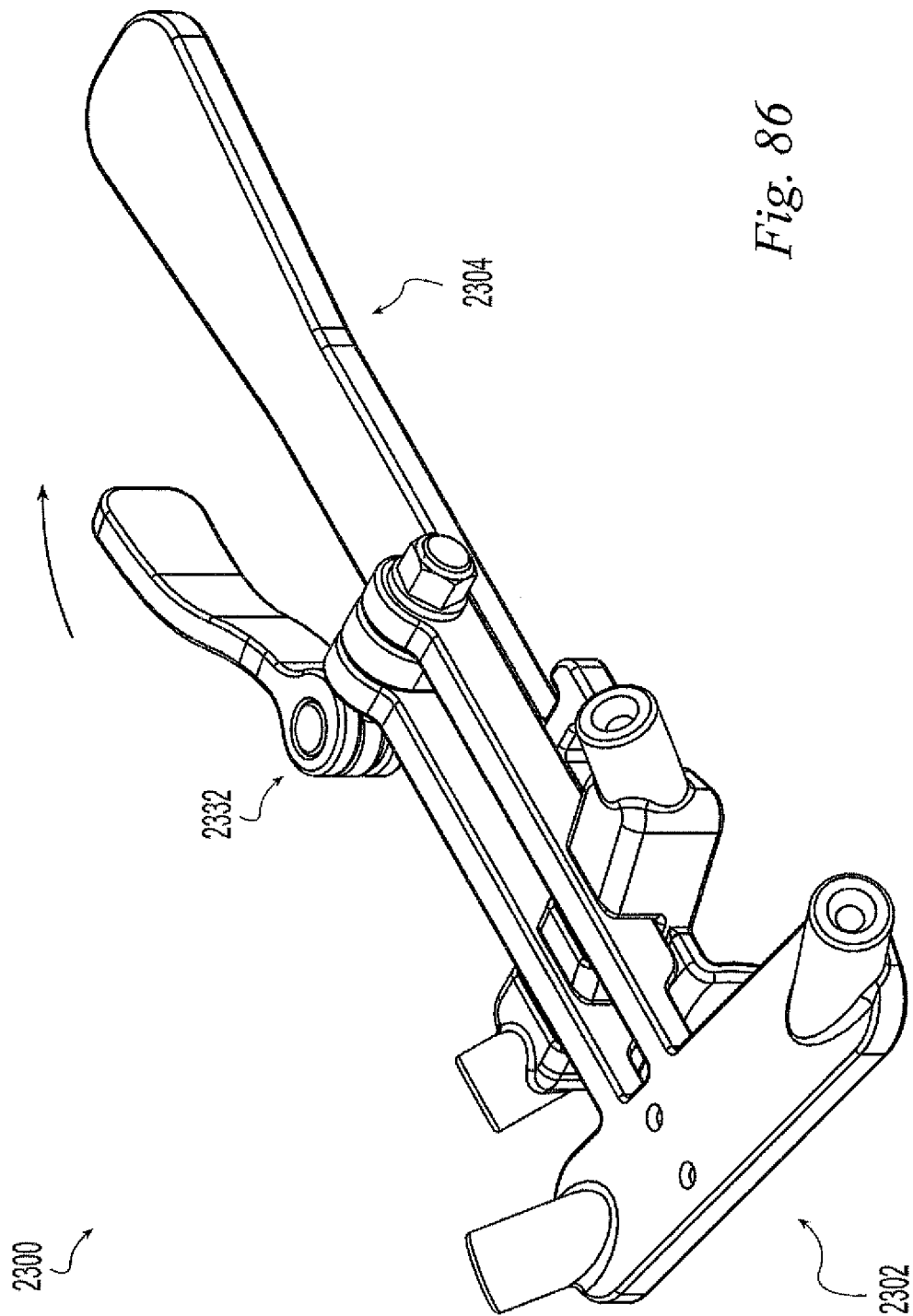
FIG. 86 is a perspective view of the guide of FIG. 78 showing a position of the guide.

FIG. 82 depicts the guide 2300 locked in the first parallel position. FIG. 83 depicts the guide 2300 with the cam 2332 unlocked by rotating lever 2337 and the first member 2302 rotated part-way toward the second position. FIG. 84 depicts the guide 2300 with the first member 2302 rotated further toward the second position. FIG. 85 depicts the guide 2300 with the first member rotated fully into the second position. FIG. 86 depicts the guide 2300 with the cam 2332 locked to fix the first and second members 2302, 2304 in the second position.

The relative position and orientation of the reference surface 2351 of the head referencing member 2350, the handle axis 2341, the handle top surface 2343, the phalangeal extensions 2346, 2347, and the metatarsal extensions 2314, 2315 are determined from averaged anthropometric data relating the metatarsal head articular surface, metatarsal longitudinal axis, and transverse plane of the human body to the medial and lateral PCL origins and insertions when the guide 2300 is locked in the second position and placed on the bone with the reference surface 2350 engaged with the metatarsal head 2106, the handle axis 2341 parallel to the axis 110 of the metatarsus, and the handle top surface 2343 parallel to the transverse plane such that the metatarsal extension axes 2311, 2313 intersect the PCL origins and the phalangeal extension axes 2345, 2349 intersect the PCL origins.

Figure 87:
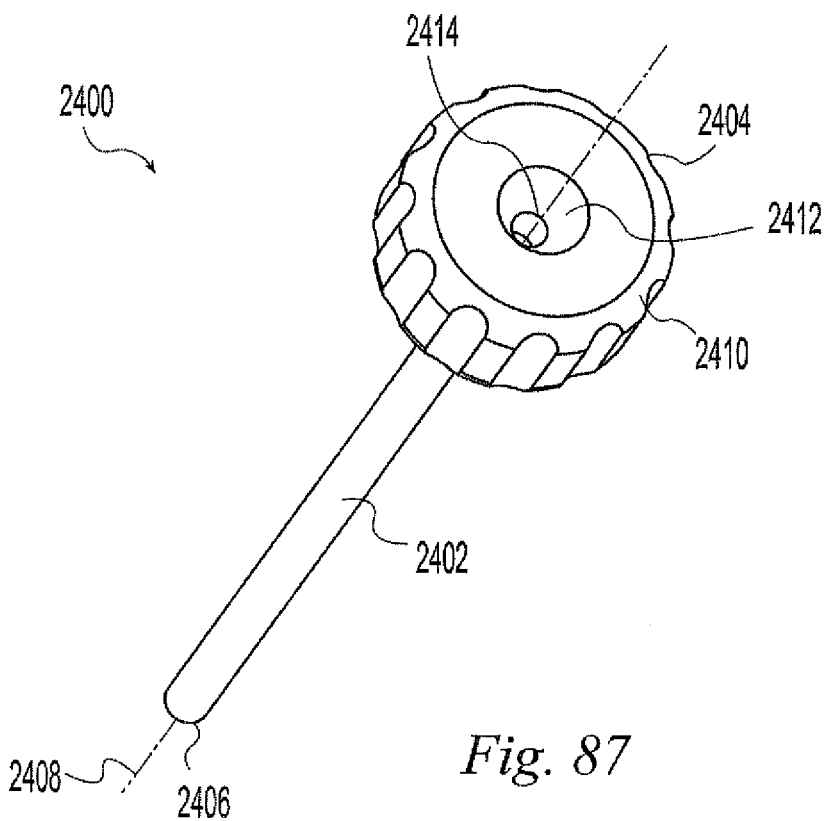
FIG. 87 is a perspective view of a tube useable with the guide of FIG. 78.
Figure 88:
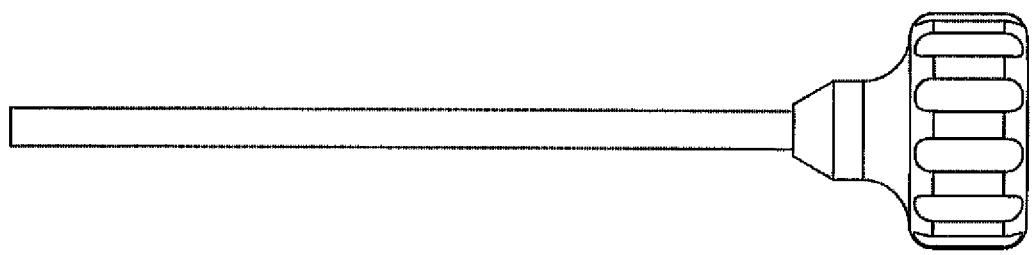
FIG. 88 is a side elevation view of the tube of FIG. 14.

FIGS. 87 and 88 illustrate an elongated tube 2400 that may be used with guide 2300 to protect soft tissue, facilitate engaging a cutter with the guide, and stabilize the cutter. For example, a long narrow drill, punch, pin, broach, or the like may be difficult to align with the extensions 2314, 2315, 2346, 2347 and/or may be so flexible that it tends to skive off the bone surface. The tube 2400 includes a tubular shaft 2402 having a proximal end 2404, a distal end 2406, and a longitudinal axis 2408 extending from the proximal end 2404 to the distal end 2406. The proximal end is radially enlarged to form a knob 2410. The knob 2410 includes a counter sink 2412 forming a funnel-like lead-in to the inner bore 2414 of the tubular shaft 2402. The outside of the shaft 2402 is sized to slide into the extensions of the guide 2300 and extend through the guide 2300 to contact the underlying bone. The shaft 2402 provides positive guidance of the cutter to the bone surface. The knob 2410 provides the user with a gripping surface spaced away from the inner bore 2414 to protect the user from being pricked by the cutter as the cutter is engaged with the inner bore 2414. The countersink 2412 guides the cutter into the inner bore 2414.

Figure 89:
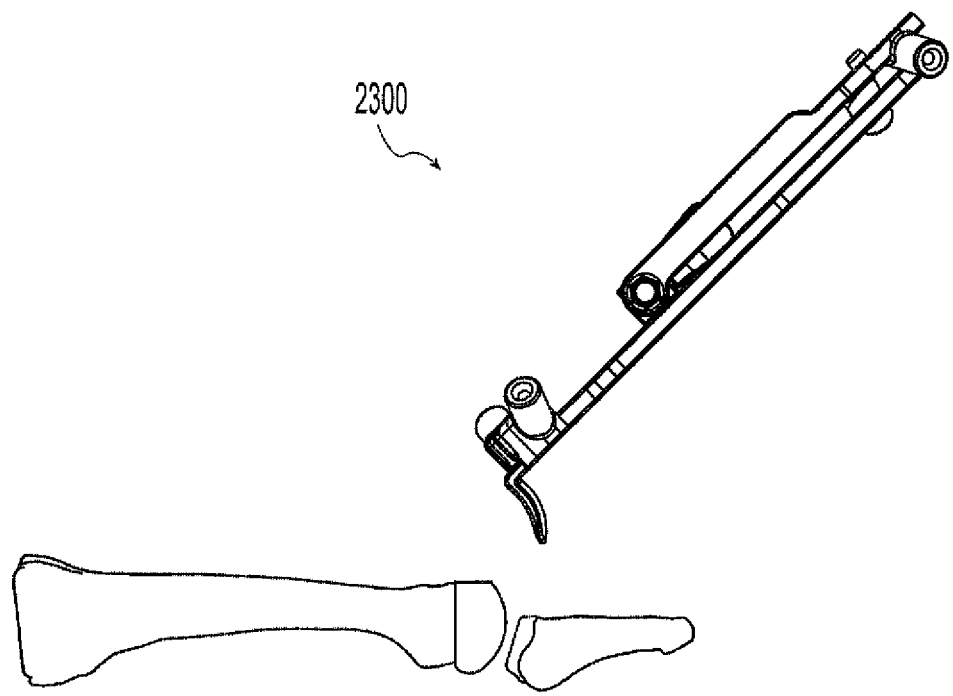
FIG. 89 is a side elevation view of the guide of FIG. 78 in use with an MTP joint.
Figure 90:
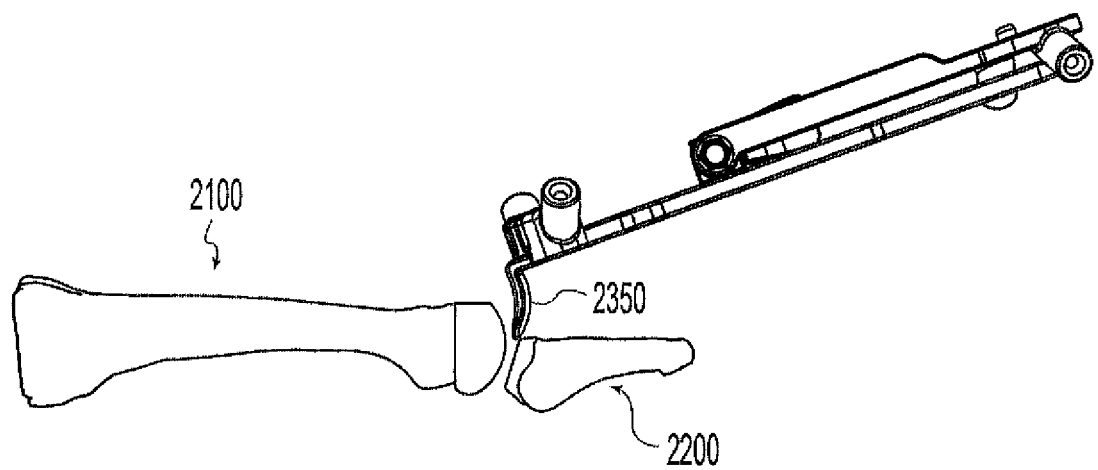
FIG. 90 is a side elevation view of the guide of FIG. 78 in use with an MTP joint.
Figure 91:
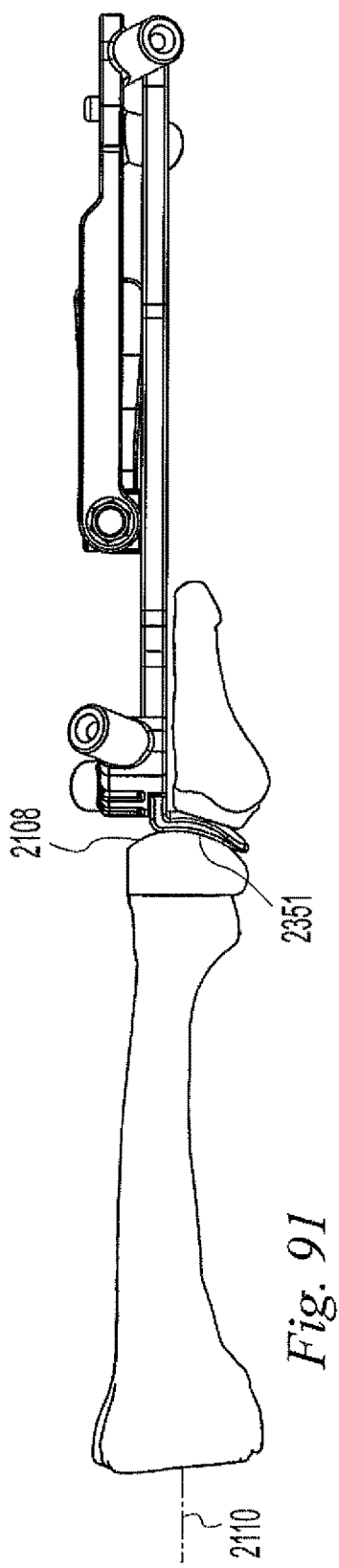
FIG. 91 is a side elevation view of the guide of FIG. 78 in use with an MTP joint.
Figure 92:
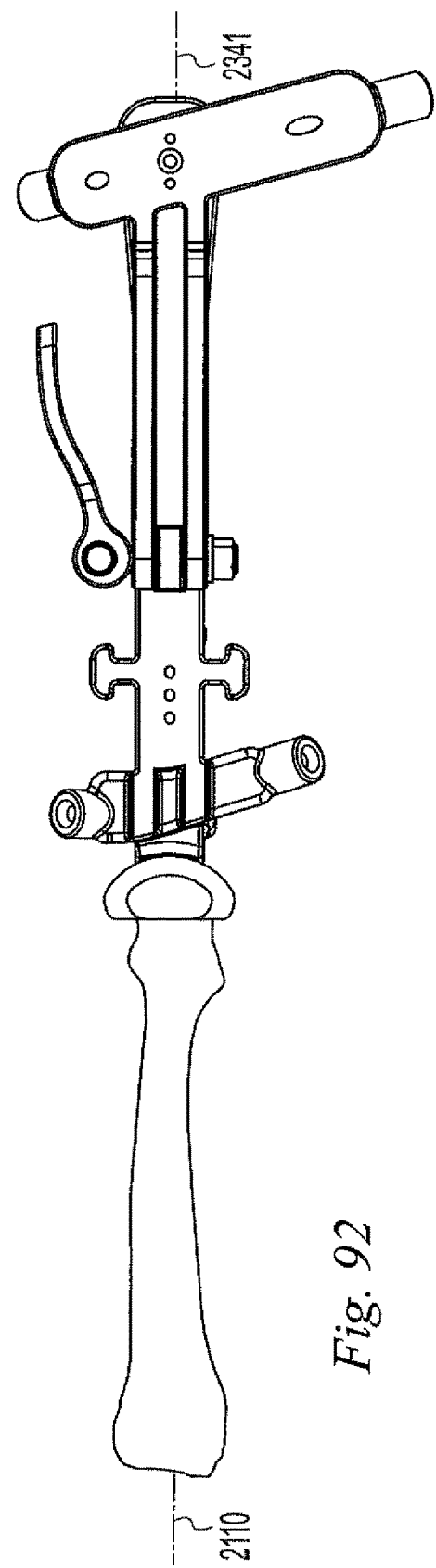
FIG. 92 is a top plan view of the guide of FIG. 78 in use with an MTP joint.
Figure 93:
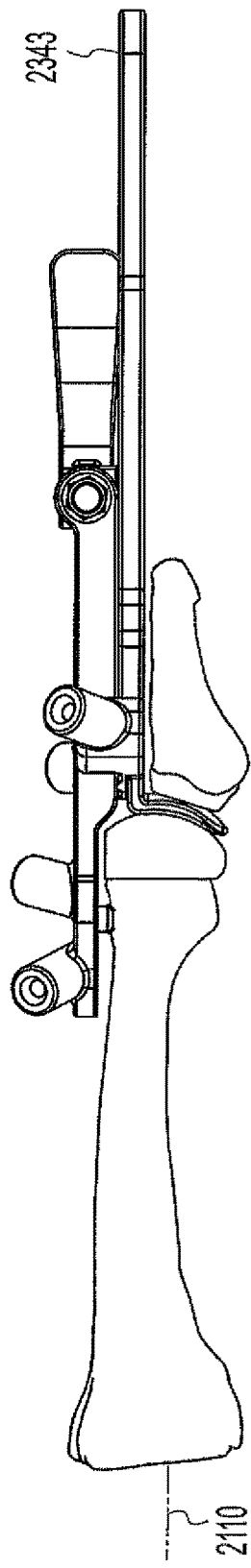
FIG. 93 is a side elevation view of the guide of FIG. 78 in use with an MTP joint.
Figure 94:
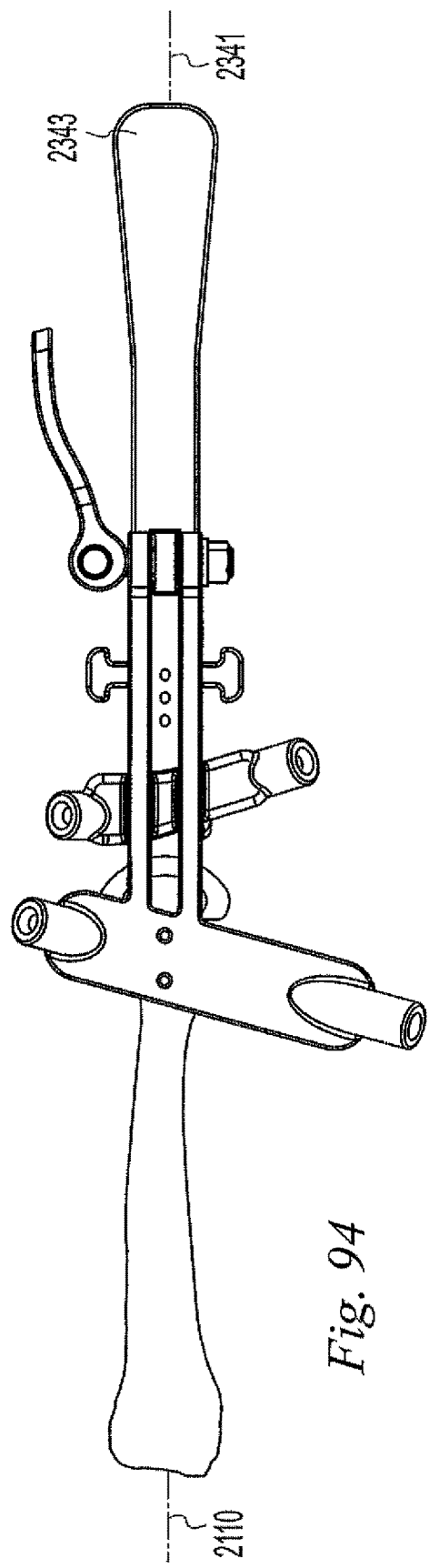
FIG. 94 is a top plan view of the guide of FIG. 78 in use with an MTP joint.
Figure 95:
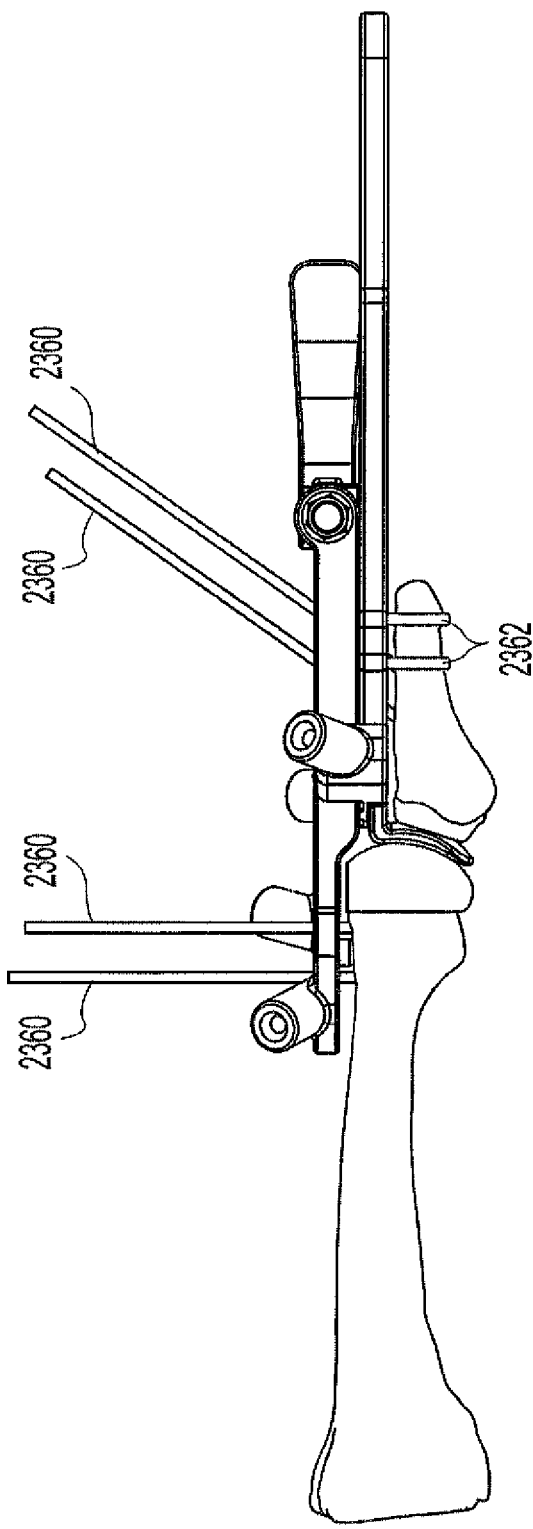
FIG. 95 is a side elevation view of the guide of FIG. 78 in use with an MTP joint.
Figure 96:
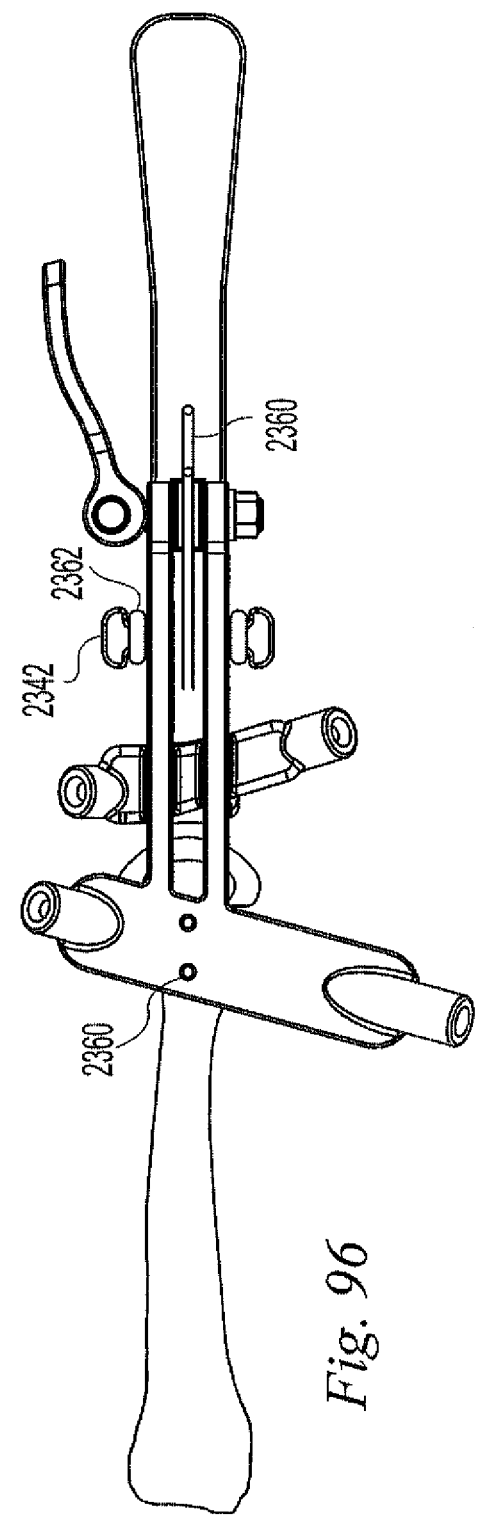
FIG. 96 is a top plan view of the guide of FIG. 78 in use with an MTP joint.

FIGS. 89-98 illustrate the guide 2300 in use to guide a cutter to form holes in the bones of the second MTP joint to facilitate, e.g., the reconstruction of the joint. The guide 2300 is brought near the joint with the first and second members folded in the first position as shown in FIG. 89. The head referencing member 2350 is inserted into the joint space between the metatarsus 2100 and phalanx 2200 as shown in FIG. 90. The concave reference surface 2351 is registered with the convex articular surface 2108 of the metatarsal head and the convex reference surface opposite the concave reference surface is registered with the concave articular surface of the proximal phalanx. The guide handle axis 2341 is oriented parallel to the axis 110 of the metatarsus and the guide handle top surface 2343 is oriented parallel to the transverse plane as shown in FIGS. 91 and 92. The first member is then pivoted into the second position as shown in FIGS. 93 and 94. The orientation of the guide 2300 may be checked again. The cam is actuated to lock the members relative to one another and fixation devices, e.g. pins 2360, may be placed in the guide fixation holes to fix the members to the bones as shown in FIGS. 95 and 96. An elastic band 2362 may be wrapped around the phalanx and engaged with the bosses 2342 to secure the second member 2304 to the phalanx in addition to, or as an alternative to, the fixation pins 2360.

Once the members are aligned and secured, the guide is used to guide a cutter to form one or more tunnels in the bones as shown in FIGS. 97 and 98. The cutter 2364 may be engaged directly with an extension of a guide portion and advanced into the bone. Alternatively, an elongated tube 2400 may first be engaged with the guide portion and extended to the bone surface. The cutter may then be engaged with the elongated tube 2400 and advanced into the bone.

FIGS. 99-101 illustrate bone tunnels formed using guide 2300 and ligaments reconstructed using the tunnels. The metatarsal guide portion 2312 has guided a cutter to form a medial-dorsal tunnel 2500 extending from the medial PCL origin into the metatarsus and a lateral-dorsal tunnel 2502 extending from the lateral PCL origin into the metatarsus. The tubular extensions 2314, 2315 of the metatarsal guide portion 2312 are oriented so that their axes intersect below the dorsal surface of the metatarsus. Thus, the tunnels 2500, 2502 intersect within the metatarsus and provide a path for fixing grafts 2501, 2503 to reconstruct one or both of the PCLs. A graft may be attached to the metatarsus by, e.g., pulling a traction suture through the tunnels and using it to pull the graft into the appropriate tunnel. For example, to attach a medial graft 2501, the traction suture may be threaded into the medial tunnel 2500 and out the lateral tunnel 2502. The suture is then tensioned to draw the graft into the medial tunnel. The graft may be fixed by tying the suture, with a suture anchor, with an interference anchor, or with other suitable methods of fixation. A lateral graft 2503 may be similarly positioned and both medial and lateral grafts may be simultaneously positioned.

The phalangeal guide portion 2344 has guided a cutter to form a tunnel 2510 extending from the medial-dorsal surface 2512 of the phalanx to the insertion 2514 of the lateral PCL on the lateral-plantar surface of the phalanx. The guide has also guided a cutter to form a tunnel 2520 extending from the lateral-dorsal surface 2522 of the phalanx to the insertion 2524 of the medial PCL on the medial-plantar surface of the phalanx. These two phalangeal tunnels cross each other without intersecting. Grafts may be pulled into these tunnels by, e.g., passing a traction suture through one of the tunnels and drawing the graft into the tunnel. The holes 2560 are formed by fixation members 2360 used to hold the guide in place.

Figure 102:
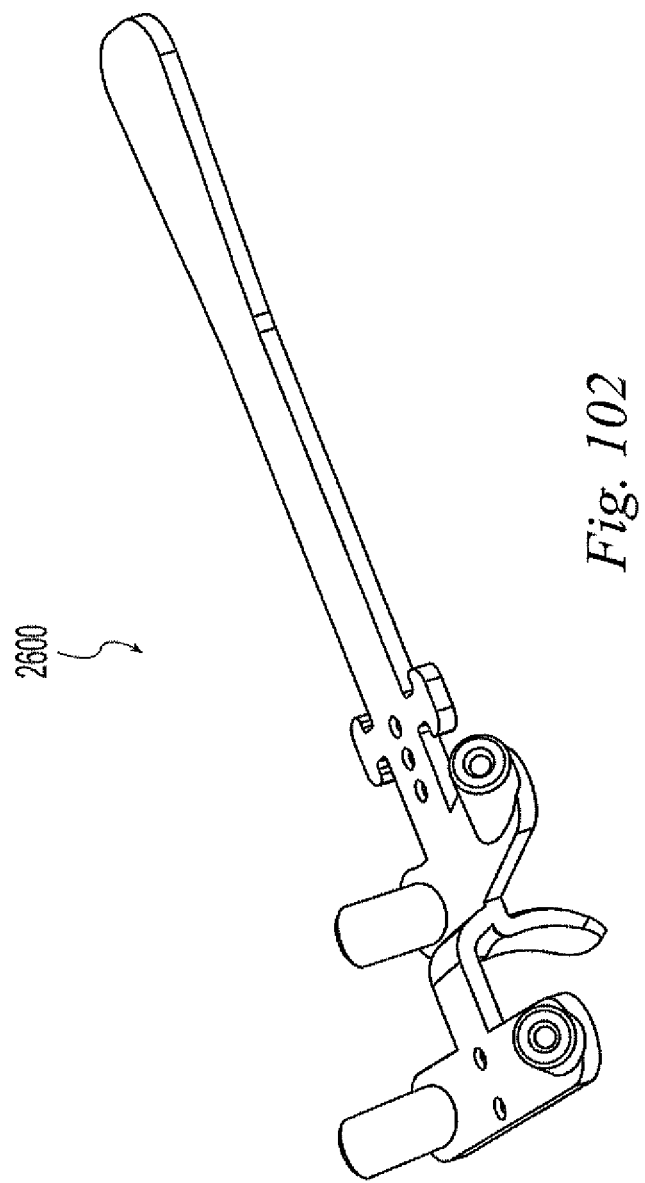
FIG. 102 is a perspective view of an illustrative example of a guide according to the present invention.
Figure 103:
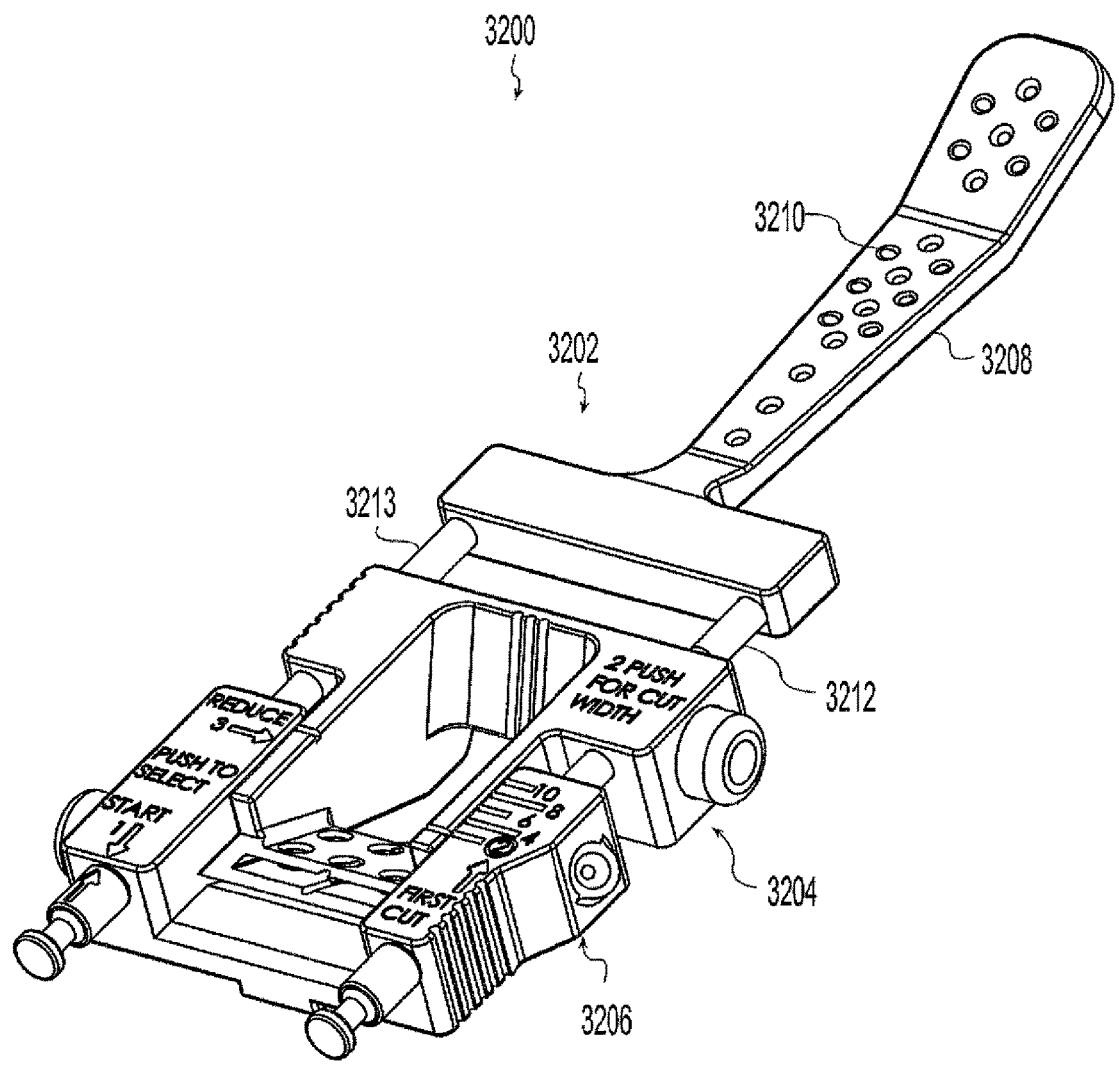
FIG. 103 is a perspective view of an illustrative example of a guide according to the present invention.
Figure 104:
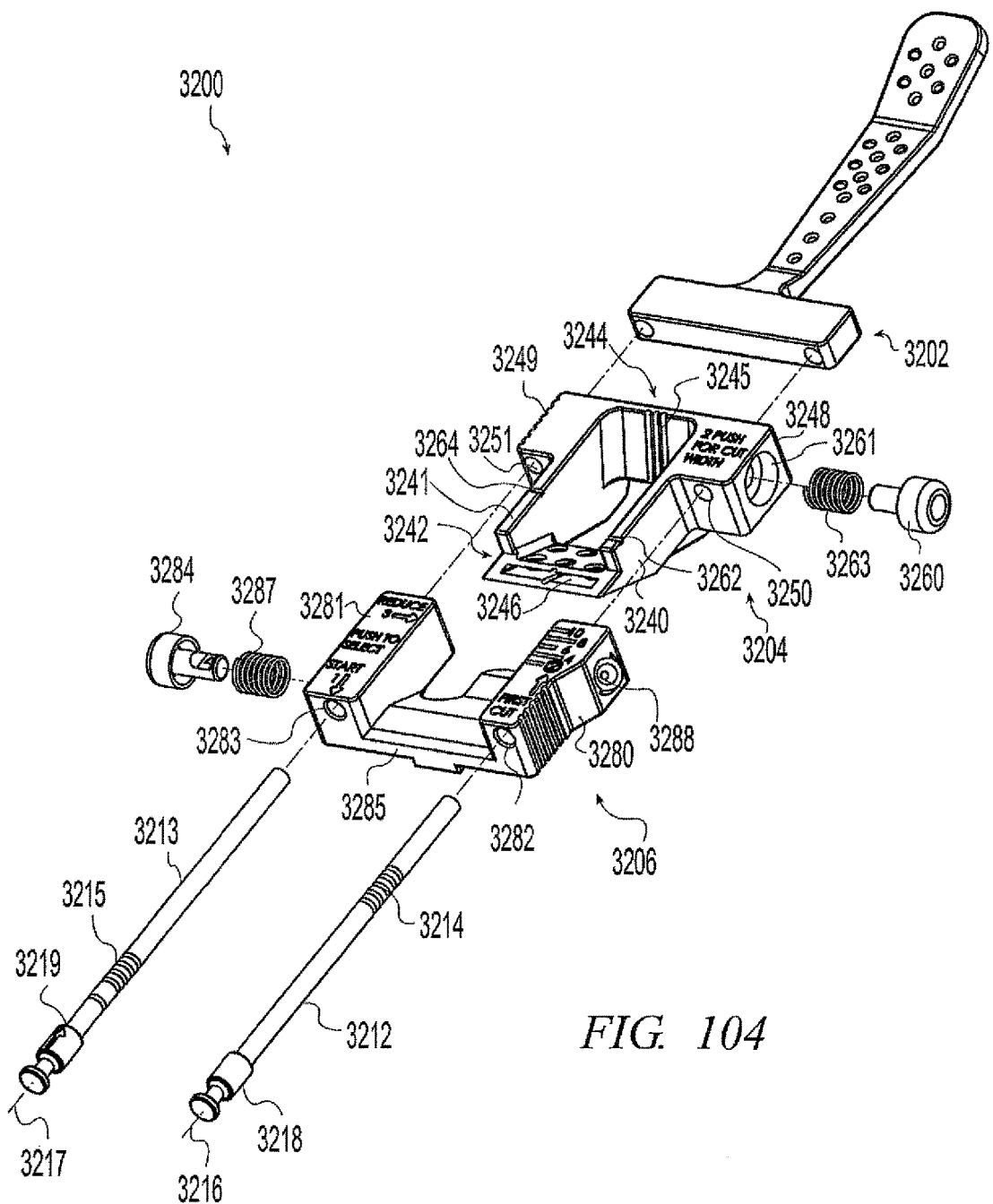
FIG. 104 is an exploded perspective view of the guide of FIG. 103.
Figure 105:
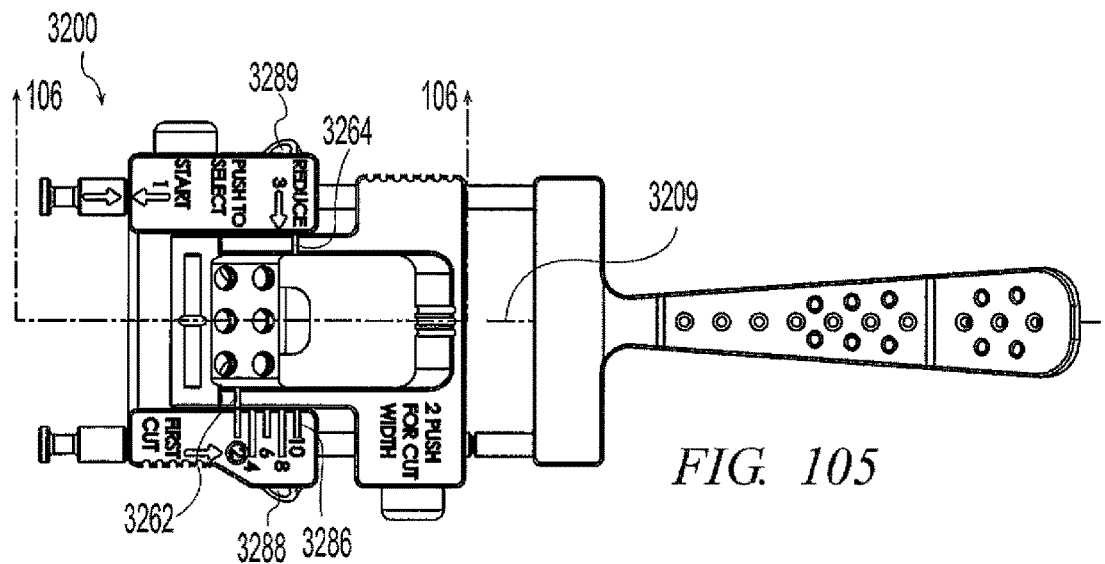
FIG. 105 is a top plan view of the guide of FIG. 103.

The illustrative guide of FIGS. 78-86 includes two separate members hinged together. Alternatively, the guide may be provided as two separate guides each having a joint reference surface and useable independently to drill tunnels in the metatarsus and proximal phalanx. Alternatively, the hinge may be removed and the two members combined into one non-movable unitary structure 2600 as shown in FIG. 102.

The illustrative guide of FIGS. 78-86 is configured to reference to the anatomy of the right second MTP joint of the human foot to guide a cutter to form tunnels in the metatarsus and phalanx that intersect the medial and lateral PCL origins and insertions to facilitate routing and attaching ligaments to reconstruct the PCLs. The guide may be mirrored for use on the left foot and the guide may be provided in sizes for different MTP joints and various sized feet. However, it has been found that the variation of the PCL origin and insertion anatomy is surprisingly small for the second MTP joint across a wide range of foot sizes and it is possible to provide a single sized guide for all left second MTP joints and another for all right MTP joints for feet from at least a woman's US size 7 to a man's US size 11.

The medial and lateral ACLs of the MTP joint have origins that are co-located with the medial and lateral PCL origins on the metatarsus. The ACLs then fan out to insert into the plantar plate close to where the plantar plate transitions into the intermetatarsal ligament (IML). Therefore, the same tunnels used to reconstruct the PCL origins may be used to reconstruct the ACL origins such that the illustrative guide 2300 configured for PCL reconstruction may also be used for ACL reconstruction.

The drill guide may have any number of cutter guides targeted at any desired anatomical feature. While the illustrative examples have depicted a guide configured for ACL and PCL reconstruction of the right human MTP joint, the guide may be similarly configured to target other ligament reconstructions or other surgical procedures at other locations throughout the body.

FIGS. 103-111 depict an illustrative example of a cut guide for cutting a material into two relatively moveable portions and relatively repositioning the portions. For example, the guide may be used as an osteotomy guide 3200 and used, e.g., in relatively repositioning first and second portions of a bone. For example, the guide 3200 may be used to shorten a metatarsal bone by moving proximal and distal portions of the bone closer together. The illustrative osteotomy guide 3200 provides a stable base with a cutter guide operable to guide a cutter to separate the bone into two, relatively moveable portions. The cutter guide is further operable to guide a cutter to form two parallel cuts transverse to the bone axis to remove a predetermined portion of the bone. The illustrative osteotomy guide 3200 provides a reduction mechanism operable to reduce a gap between the two bone portions with motion along a predefined axis.

The guide 3200 includes a proximal base member 3202, an intermediate inner stage 3204, and a distal outer stage 3206 all mounted in relative translating relationship. The base member 3202 includes an elongated plate-like handle 3208 including a plurality of fixation holes 3210. First and second spaced apart, parallel guide arms 3212, 3213 are rigidly joined to the base member and extend opposite the elongated handle 3208.

The arms include annular notches 3214, 3215 for controlled positioning of the stages at discrete locations along the arms. The arms define parallel translation axes 3216, 3217. Each arm has a radially enlarged stop 3218, 3219 near its distal end against which the outer stage 3206 may abut to define a distal limit of travel of the outer stage 3206 on the arms 3212, 3213.

The inner stage 3204 is a generally box-like member having first and second opposed sides 3240, 3241 joined at one end by a first end wall defining a cutter guide 3242 and at an opposite end by a second end wall 3244. The second end wall 3244 includes fixation guide grooves 3245 formed in a plane transverse to the translation axes 3216, 3217. In the illustrative example of FIGS. 103-111, the cutter guide 3242 is in the form of a saw guide having a saw blade guiding slot 3246. The sides 3240, 3241 include outwardly extending bosses 3248, 3249 having through holes 3250, 3251 for receiving the guide arms 3212, 3213 in sliding engagement so that the inner stage 3204 may be moved axially along the translation axes 3216, 3217.

The saw blade guiding slot 3246 defines a plane oriented relative to the translation axes 3216, 3217 to guide a saw blade in a predetermined orientation relative to the axes 3216, 3217. In the illustrative example of FIGS. 103-111, the slot 3246 forms an angle 3252 (FIG. 106) relative to the plane defined by the axes 3216, 3217. This angle 3252 is selected to minimize the shear stresses on the healing osteotomy. For example, in the illustrative example of FIGS. 103-111, the angle is chosen based on typical metatarsal anatomy. In a typical patient standing upright on a level floor, the metatarsal axis 3108 forms an angle of approximately 10-40 degrees relative to the floor. It is desirable for the osteotomy cut surfaces to be parallel to the floor such that when the patient is standing upright there is little or no shear force in the plane of the healing bone surfaces. In use, the guide axes, 3216, 3217 are oriented parallel to the metatarsal axis 3108. Therefore, the blade guiding slot 3246 is preferably oriented at an angle 3252 of 10-40 degrees relative to the guide axes 3216, 3217 to produce the desire cut. More preferably, the angle 3252 is 15-30 degrees. In the illustrative example of FIGS. 103-111, the angle 3252 is 25 degrees.

A button 3260 is received in a hole 3261 formed in the first side 3240 and biased by a spring 3263. The button 3260 includes a feature engageable with the annular notches 3214 of the first arm 3212 to selectively lock the position of the inner stage 3204 relative to the arm as will be explained more fully below. The feature may be, e.g., a ring, notch, pin, or other feature engageable with the annular notches 3214. The first side 3240 includes a reference mark 3262 to indicate the position of the inner stage relative to the outer stage to indicate cut width as will be explained more fully below. The second side 3241 includes a reference mark 3264 to indicate the position of the inner stage relative to the outer stage to indicate bone reduction as will be explained more fully below.

Figure 106:
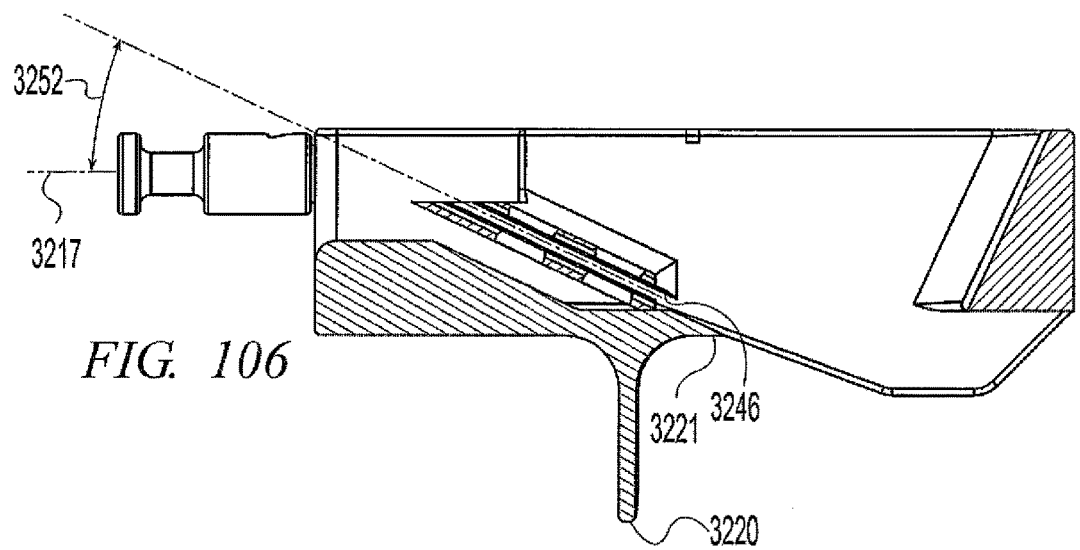
FIG. 106 is a side sectional view of the guide of FIG. 103 taken along line 106-106 of FIG. 105.
Figure 107:
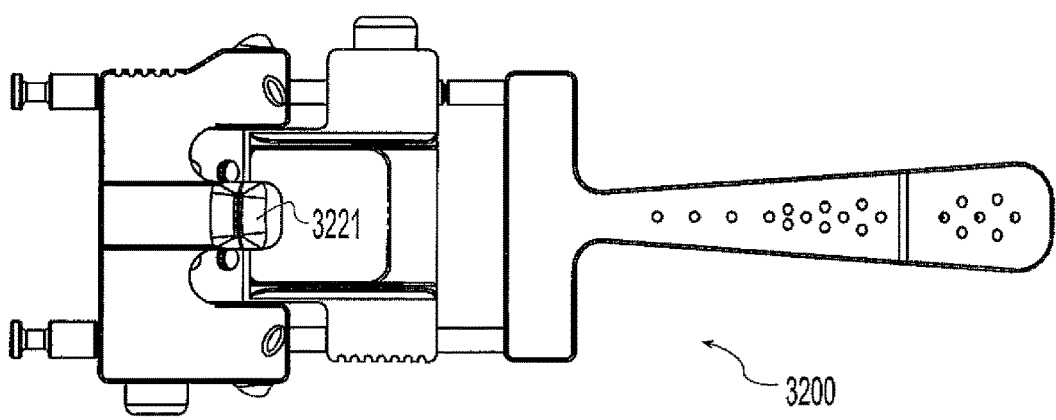
FIG. 107 is a bottom plan view of the guide of FIG. 103.
Figure 108:
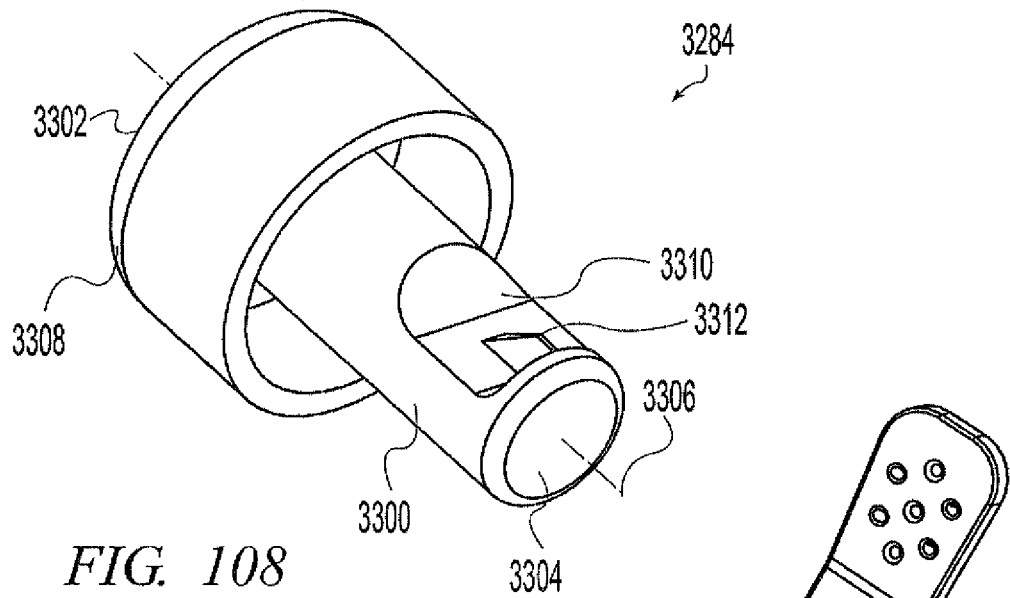
FIG. 108 is a perspective view of a component pushbutton of the guide of FIG. 103.
Figure 109:
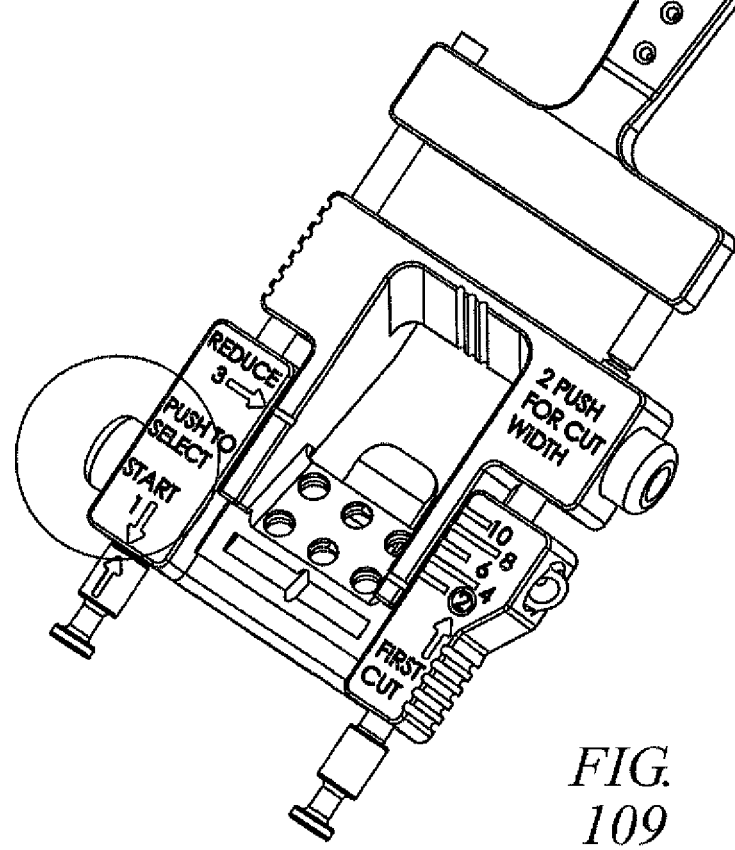
FIG. 109 is a perspective view of the guide of FIG. 103 highlighting a portion.

The outer stage 3206 is a generally U-shaped member having first and second sides 3280, 3281 joined at a first end by a first end wall 3285 and open at the second end. The outer stage 3206 includes fixation holes 3288, 3289 for receiving fixation devices, e.g. pins, screws or the like, to attach the outer stage to the metatarsal bone near the head. The outer stage 3206 further includes a first reference member 3220 extending downwardly away from the stage as best seen in FIG. 106 and a second reference member 3221 extending proximally between the first and second sides. The sides 3280, 3281 include through holes 3282, 3283 for receiving the guide arms 3212, 3213 in sliding engagement so that the outer stage 3206 may be moved axially along the translation axes 3216, 3217. A button 3284, similar to button 3260, is received in a hole (not shown) in the second side 3281 and is biased by a spring 3287. The button 3284 is engageable with the annular notches 3215 to selectively lock the axial position of the outer stage relative to the arms. The first side 3280 includes reference marks, or indicia 3286, indicating the relative position of the inner stage relative to the outer stage. The indicia 3286, reference mark 3262, and annular notches 3214, 3215 are arranged so that the reference mark 3262 aligns with indicia 3286 to indicate the relative position of the inner stage, and thus the saw slot 3246, relative to the outer stage.

Figure 110:
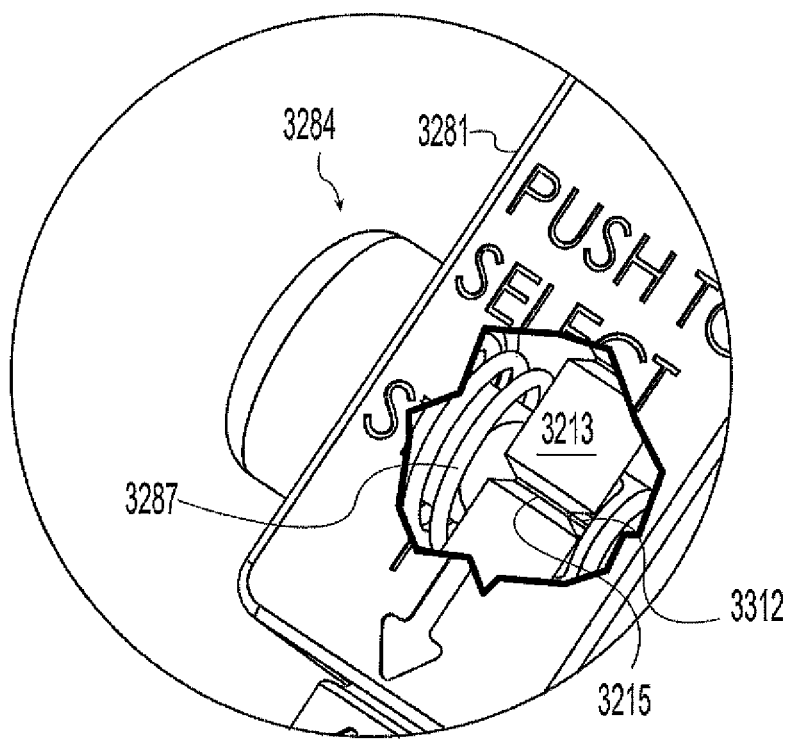
FIG. 110 is a cutaway perspective view of the guide of FIG. 103 detailing the portion highlighted in FIG. 109 showing the operation of the pushbutton of FIG. 108.
Figure 111:
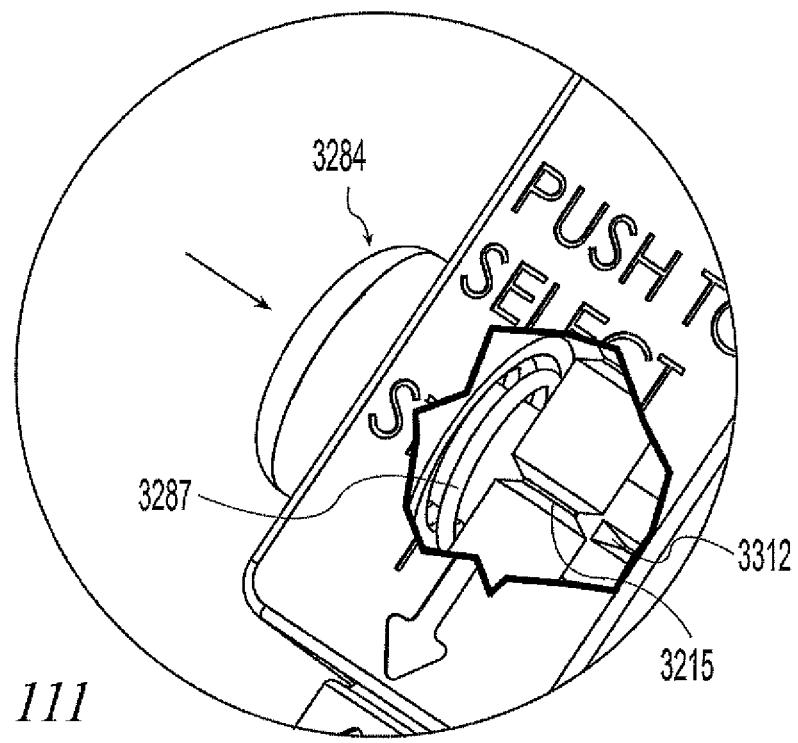
FIG. 111 is a cutaway perspective view of the guide of FIG. 103 detailing the portion highlighted in FIG. 109 showing the operation of the pushbutton of FIG. 108.

Further detail of buttons 3260 and 3284 and their operation is illustrated in FIGS. 108-111 using button 3284 as an example. The button 3284 includes a shaft 3300 extending from a first end 3302 to a second end 3304 along an axis 3306. The first end 3302 defines an enlarged head 3308. The shaft includes a notch 3310 transverse to the axis 3306 and able to receive a portion of the second guide arm 3215 in transverse sliding relationship. A key 3312 projects into and blocks a portion of the notch 3310. The button 3284 and spring 3287 are placed into the hole in the second side 3281 of the outer stage 3206. The second arm 3213 is inserted through the hole 3283 in the second side 3281 of the outer stage 3206 and through the notch 3310 in the button shaft 3300. The arm 3213 abuts a portion of the button 3284 and retains the button in the outer stage 3206. The spring 3287 biases the button 3284 outwardly causing the key 3312 to press against the arm 3213. When the key 3312 is aligned with an annular notch 3215, the spring biases the key 3312 into the notch 3215 and prevents the arm 3213 from sliding in the hole 3283 relative to the stage 3206 as shown in FIG. 110. Pressing the button 3284 inwardly compresses the spring 3287 and moves the key 3312 out of the groove allowing the stage 3206 to translate along the arm 3213 as shown in FIG. 111.

Figures 112, 113, 114:
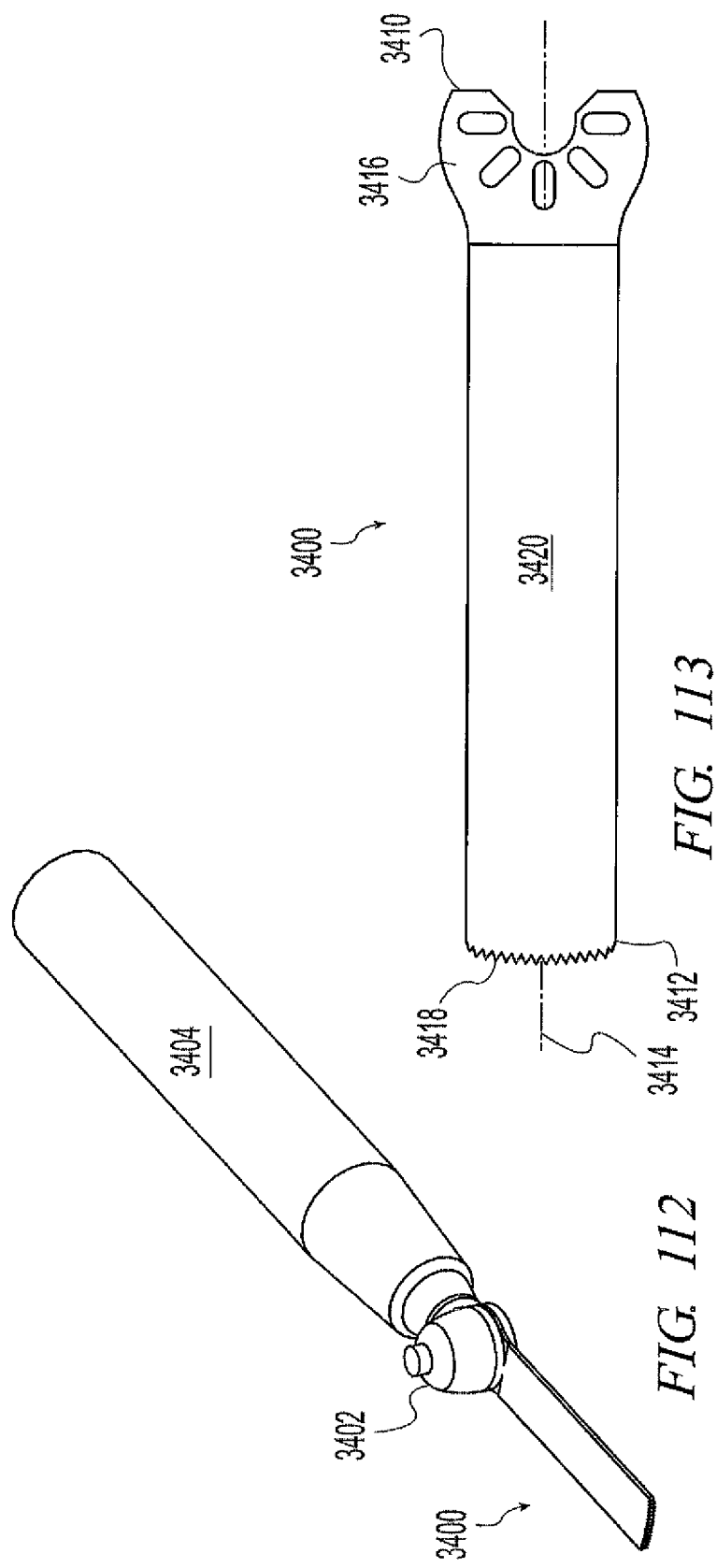
FIG. 112 is perspective view of an illustrative example of a saw blade according to the present invention useable with the guide of FIG. 103 and shown with a powered handpiece.
FIG. 113 is a top plan view of the saw blade of FIG. 112.
FIG. 114 is a side elevation view of the saw blade of FIG. 112.

FIGS. 112-114 illustrate a saw blade 3400 useable with the guide 3200. The blade may, e.g., be gripped in a chuck 3402 of a powered handpiece 3404 to drive the blade to cut a bone. In the illustrative example of FIGS. 112-114, the blade 3400 is an oscillating blade used with a powered oscillating saw. The blade 3400 is a generally plate-like member having a first end 3410, a second end 3412, and a longitudinal axis 3414 extending from the first end 3410 to the second end 3412. The first end 3410 defines a hub 3416 adapted for engagement with the powered handpiece 3404. The second end 3412 defines cutting teeth 3418 adapted to cut bone. An intermediate portion 3420 having parallel, planar top and bottom surfaces 3422, 3424 connects the hub 3416 and teeth 3418. The teeth have a thickness 3426 defined perpendicular to the top and bottom surfaces 3422, 3424. In use, the blade produces a cut having a width, or kerf, equal to the thickness 3426. In order for the blade to produce a cut that results in an osteotomy reduction that is in whole units, the thickness 3426 is related to the angle of the cut relative to the direction of reduction of the osteotomy which is parallel to the axes 3216, 3217 of the guide arms. To produce an osteotomy and resulting reduction of one unit length, the thickness 3426 is made equal to one unit length times the sine of angle 3252. In the illustrative example of FIGS. 103-111, the minimum osteotomy is two millimeters which corresponds to a single cut with the saw blade 3400. Therefore, the thickness 3426 is equal to two millimeters times the sine of 25 degrees or 0.845 mm. In the illustrative saw blade of FIGS. 112-114, the intermediate portion 3420 has a thickness 3428 equal to the thickness 3426 of the teeth and the saw slot 3246 in the inner stage 3204 is sized to receive the intermediate portion 3420 in close fitting relationship to provide support to the blade 3400. In the illustrative embodiment of FIGS. 112-114, the hub 3416 has a thickness 3430 less than the thickness 3428.

Figure 115:
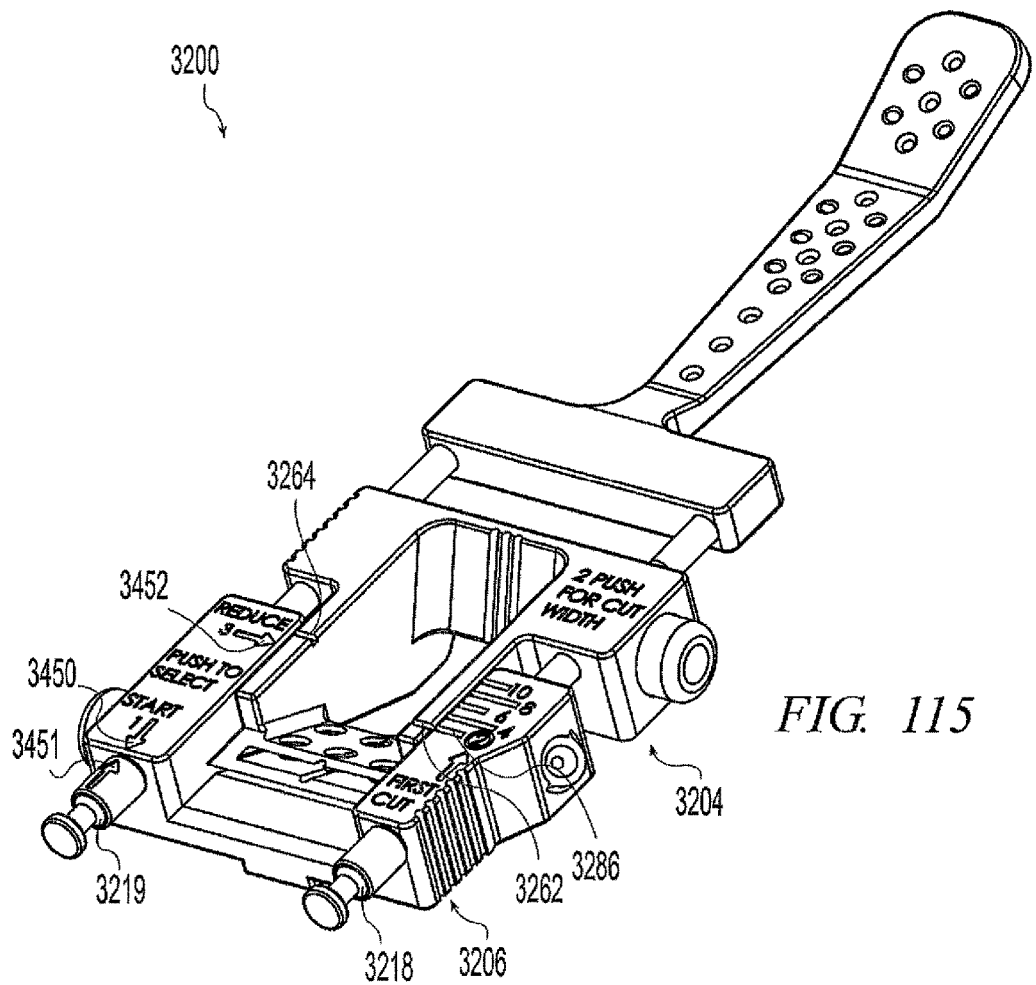
FIG. 115 is a perspective view of the guide of FIG. 103 showing a position of the guide.
Figure 116:
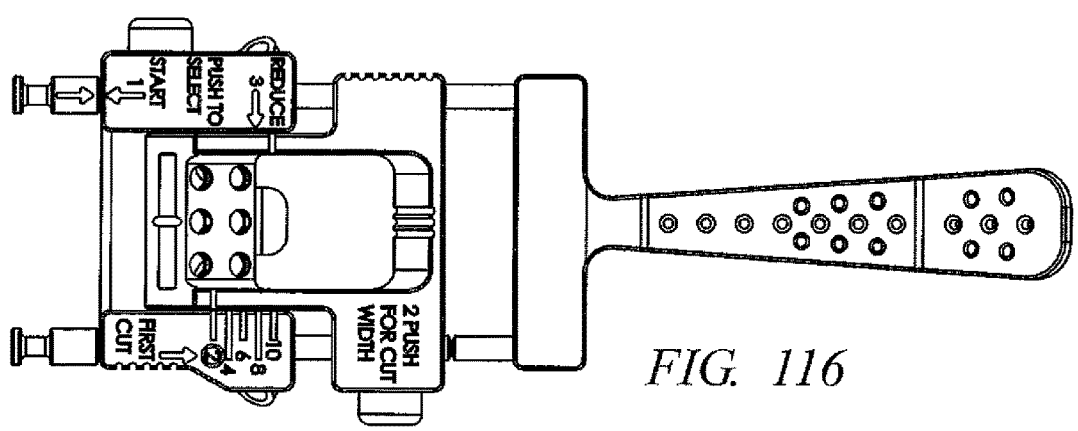
FIG. 116 is a top plan view of the guide of FIG. 103 showing the position of FIG. 115.

FIGS. 115-120 illustrate various positions of the illustrative guide 3200 of FIGS. 3-11. FIGS. 115 and 116 illustrate the guide 3200 in an initial position in which the outer stage 3206 abuts the stops 3218, 3219 and the inner stage 3204 is positioned for a minimal cut. Indicia may be provided to indicate the initial position. In the illustrative example shown, engraved arrows 3450, 3451 indicate the initial position of the outer stage 3206. An arrow 3450 on the top surface of the second side 3281 of the outer stage 3206 points distally at the distal edge of the surface. An arrow 3451 on the top of the stop 3219 points proximally at the proximal edge of the stop 3219. The outer stage 3206 is in the first, initial, or start position when the arrows are brought together until the stage 3206 abuts the stop 3219. The inner stage 3204 is in the initial position when the reference mark 3262 is aligned with the first of the indicia 3286 labeled "2" indicating that a single cut will remove bone resulting in 2 mm of reduction. Note that from this position, the outer stage 3206 can be moved 2 mm proximally relative to the inner stage 3204 to reduce the osteotomy, or in other words close the gap, created by a single cut with the illustrative saw blade of FIGS. 112-114. This is indicated by an arrow 3452 labeled "REDUCE" on the top surface of the outer stage 3206 and aligned 2 mm distal of the reference mark 3264 on the inner stage 3204. In the illustrative example, the stages 3204, 3206 and annular notches 3214, 3215 of the guide arms are arranged to allow positive relative positioning of the stages 3204, 3206 in 2 mm increments.

Figure 117:
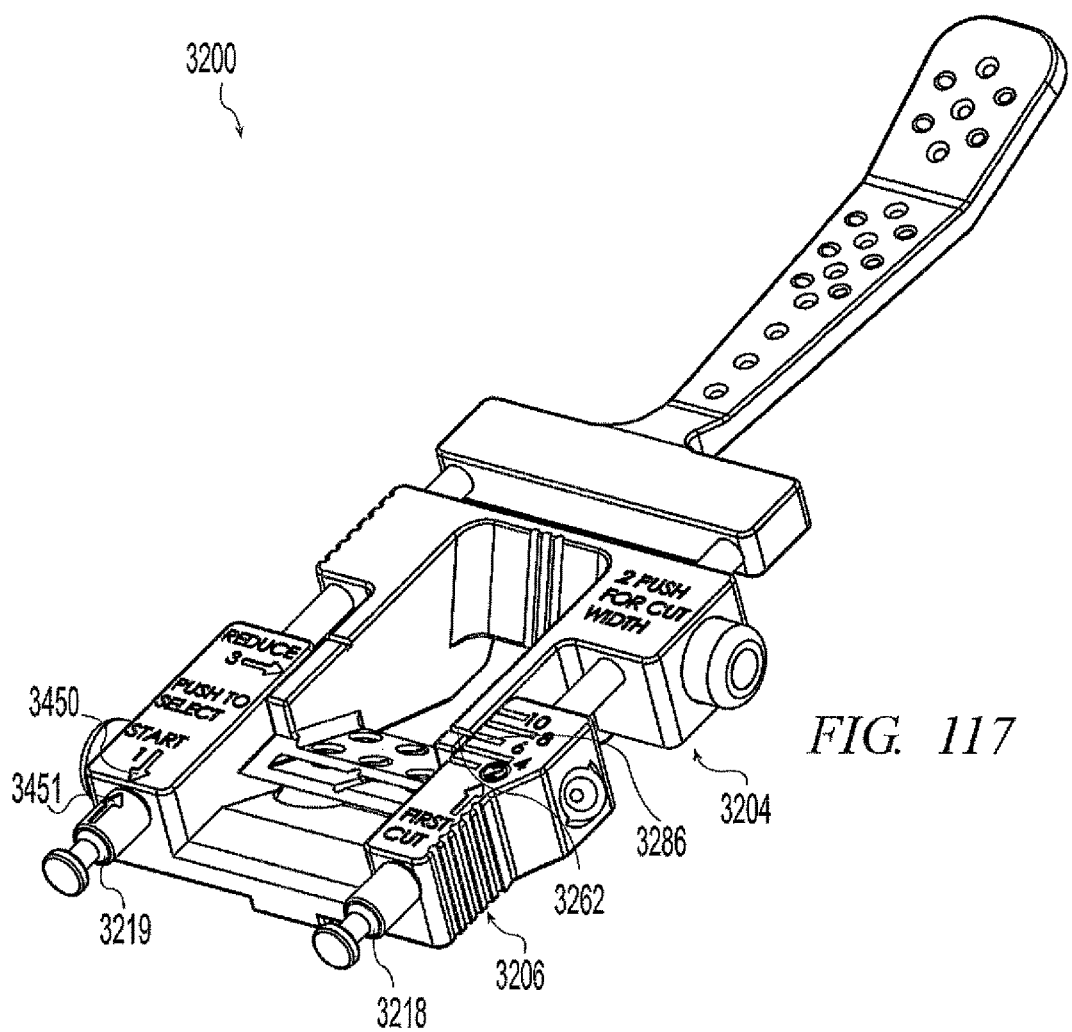
FIG. 117 is a perspective view of the guide of FIG. 103 showing a position of the guide.
Figure 118:
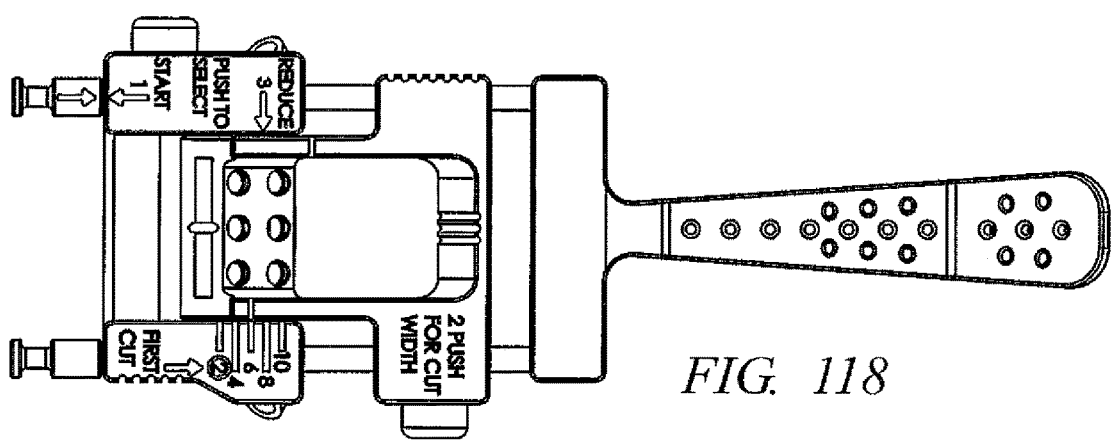
FIG. 118 is a top plan view of the guide of FIG. 103 showing the position of FIG. 117.

FIGS. 117 and 118 illustrate the guide in a second position in which the inner stage 3204 has been translated relative to the outer stage 3206 and base 3202 until the reference mark 3262 is aligned with one of the indicia 3286 indicating the desired osteotomy reduction if more than 2 mm is desired. In FIGS. 117 and 118, the reference mark 3262 is aligned with the indicia labeled "6" indicating that a second cut made with the guide in this position will, in combination with the first cut, remove a section of bone 6 mm long as measured parallel to the guide axes 3216, 3217 and will thus result in a 6 mm reduction parallel to the guide axes 3216, 3217.

Figure 119:
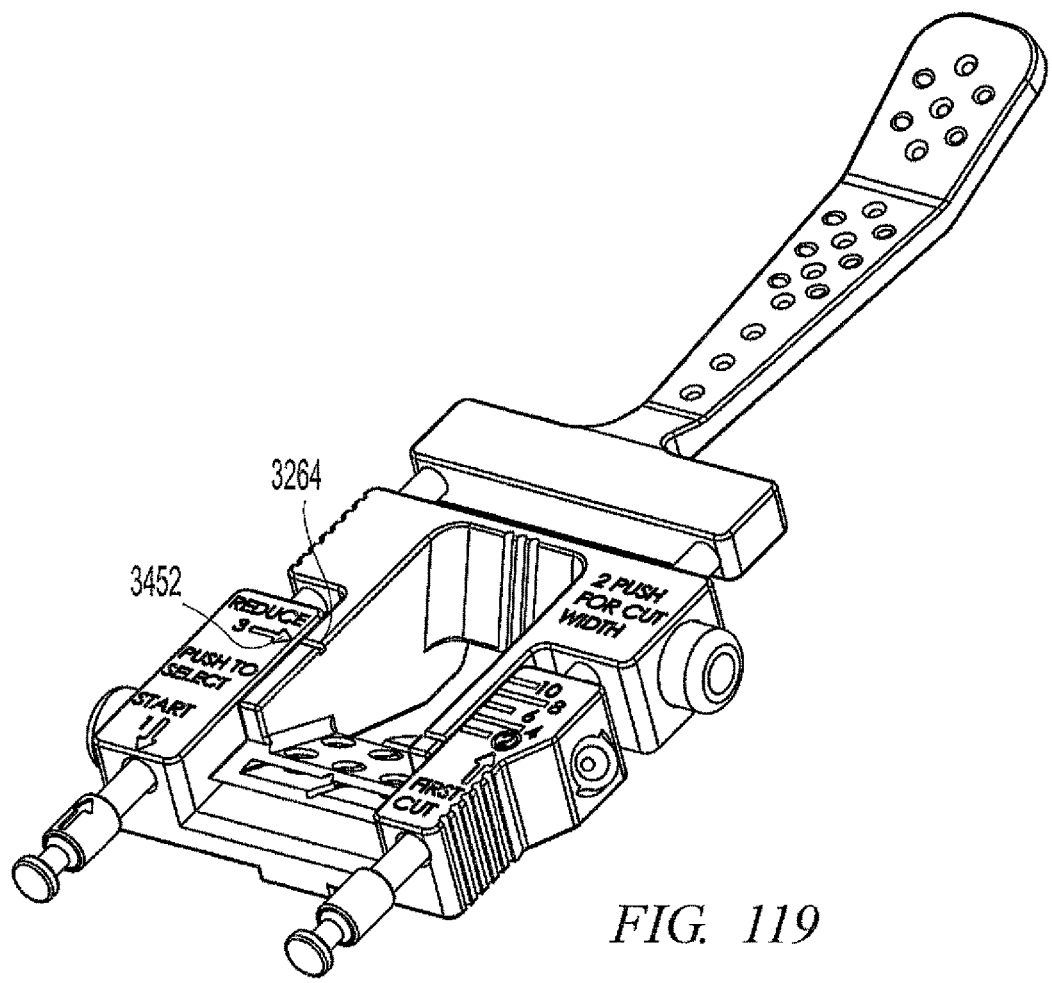
FIG. 119 is a perspective view of the guide of FIG. 103 showing a position of the guide.
Figure 120:
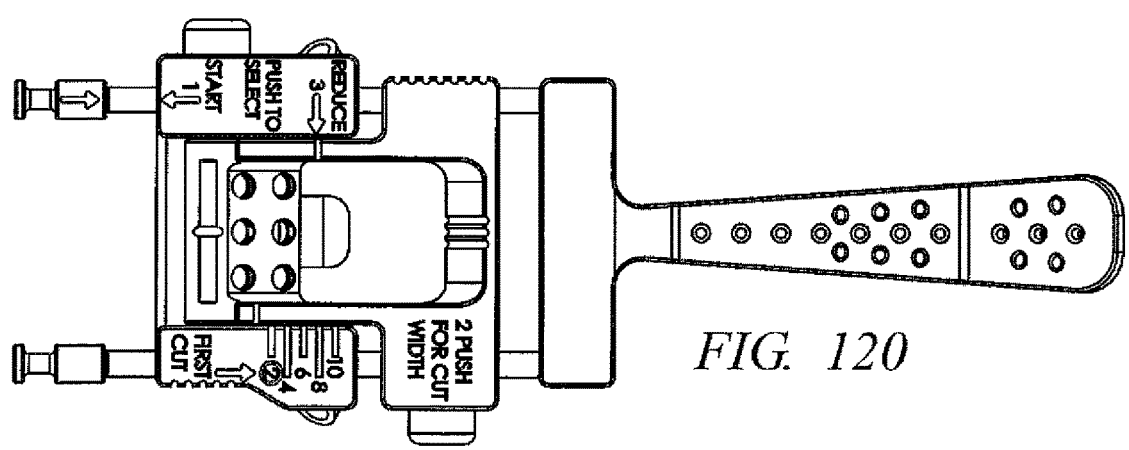
FIG. 120 is a top plan view of the guide of FIG. 103 showing the position of FIG. 119.

FIGS. 119 and 120 illustrate the guide in a third position in which the outer stage 3206 has been translated relative to the inner stage 3204 and base 3202 until the arrow 3452 is aligned with the reference mark 3264 indicating that the osteotomy has been reduced.

Figure 121:
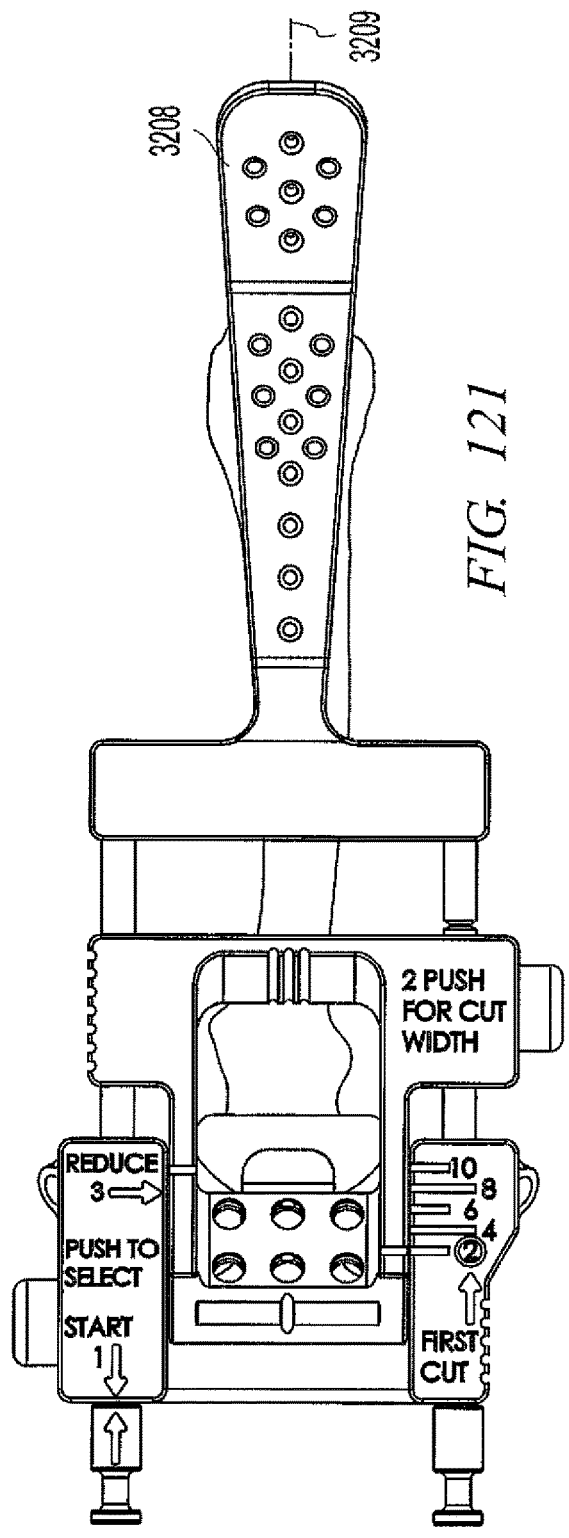
FIG. 121 is a top plan view of the guide of FIG. 103 showing a position of the guide on a metatarsus.
Figure 122:
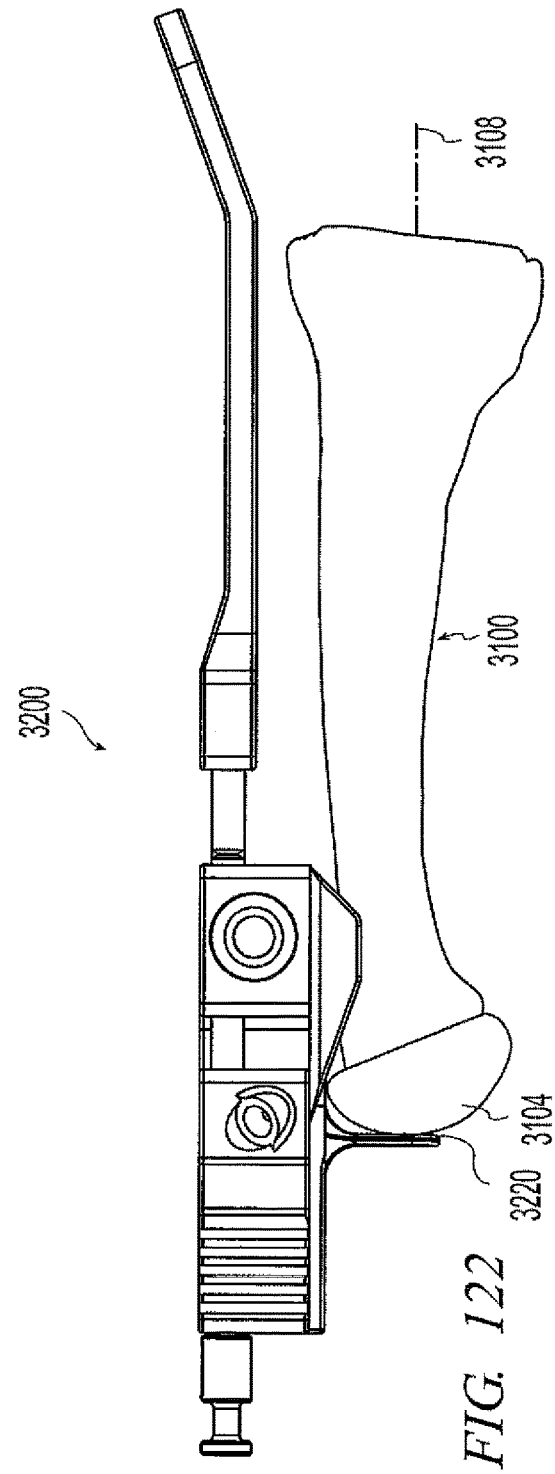
FIG. 122 is a side elevation view of the guide of FIG. 103 showing the position of FIG. 121.

FIGS. 121-131 illustrate the illustrative guide 3200 of FIGS. 103-111 in use to form and reduce an osteotomy on a metatarsus 3100. In FIGS. 121 and 122, the guide has been placed in the initial position as shown in FIGS. 115 and 116 and placed over the metatarsus 3100. The first reference member 3220 is inserted into the joint space until the second reference surface 3221 abuts the dorsal surface of the metatarsal head 3104. The guide is pressed proximally until the reference member 3220 abuts the metatarsal head 3104. The handle longitudinal axis 3209 is aligned with the metatarsal axis 3108. The top surfaces of the stages are leveled side-to-side and the cut plane is positioned parallel to the transverse axis. In this position, the guide 3200 is registered axially relative to the distal end of the metatarsal head 3104 and all six degrees of freedom of the guide 3200 have been constrained.

Figures 123, 124:
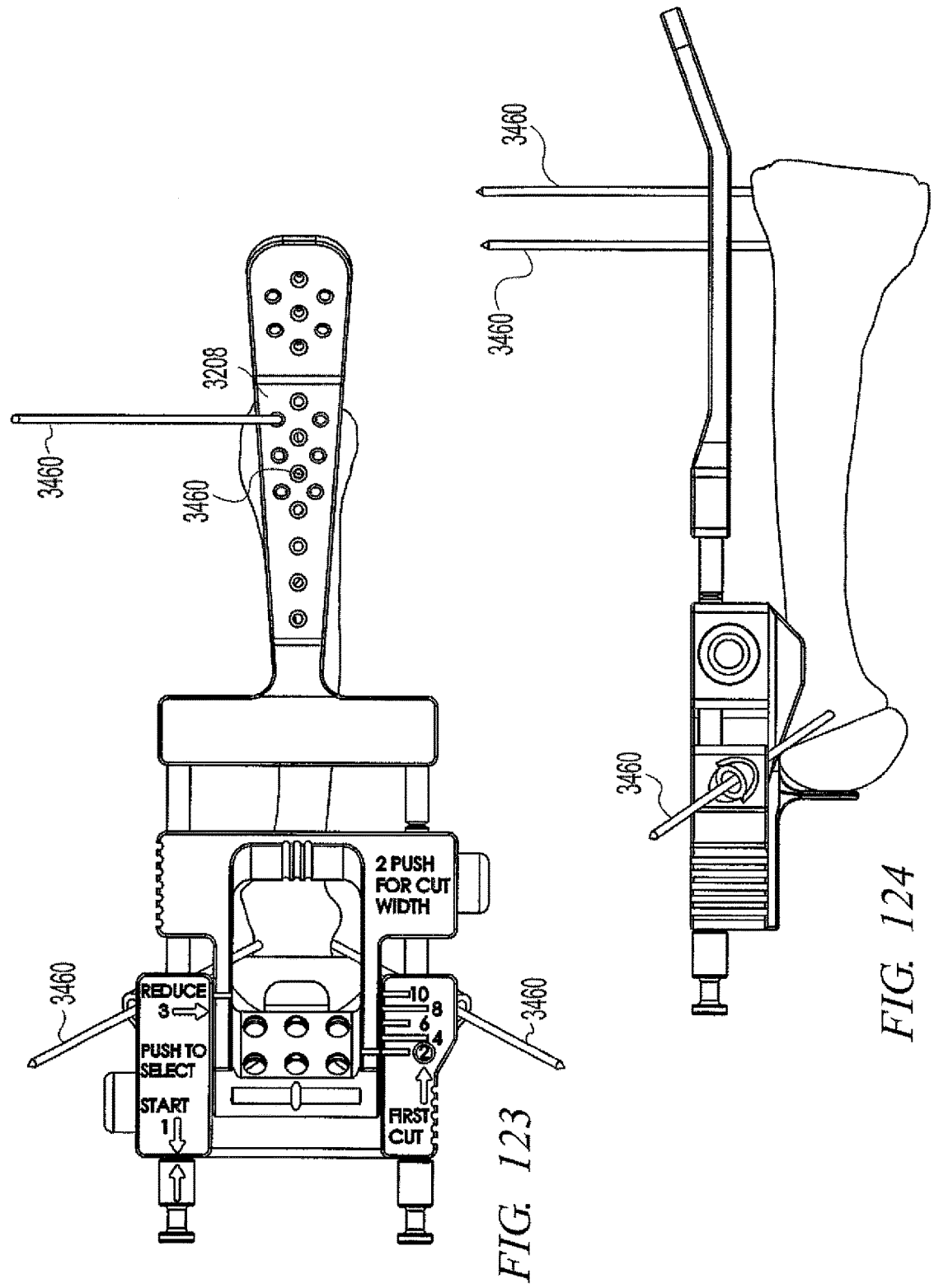
FIG. 123 is a top plan view of the guide of FIG. 103 showing a position of the guide on a metatarsus.
FIG. 124 is a side elevation view of the guide of FIG. 103 showing the position of FIG. 123.
Figure 125:
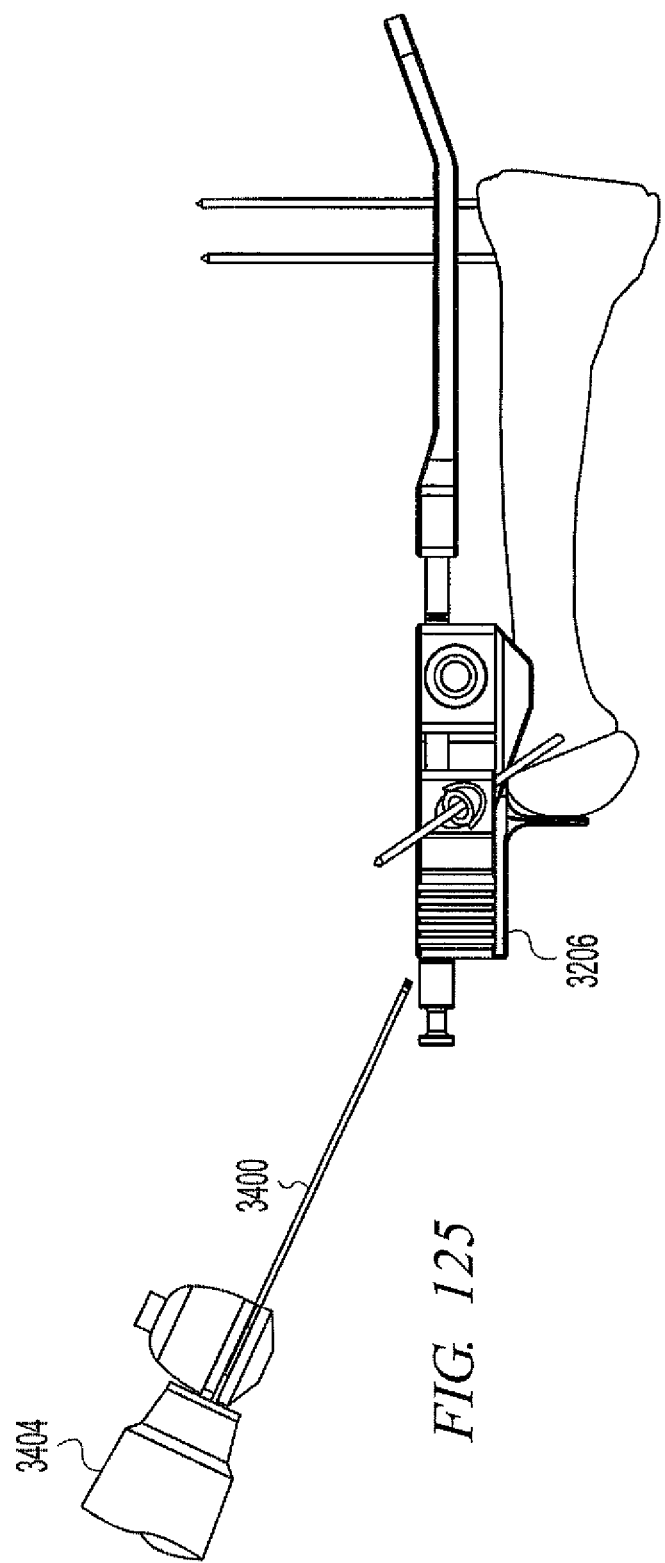
FIG. 125 is a side elevation view of the guide of FIG. 103 showing a position of the guide on a metatarsus ready to receive the saw blade of FIG. 112.
Figure 126:
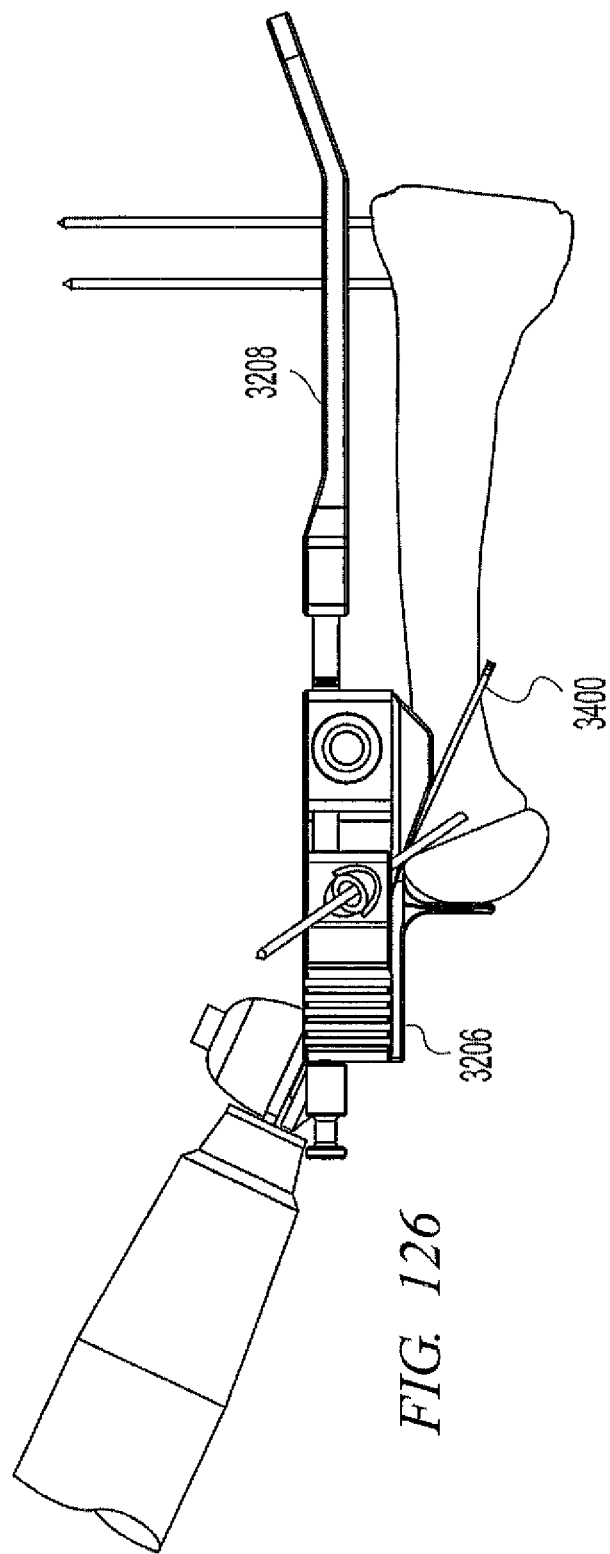
FIG. 126 is a side elevation view of the guide of FIG. 103 showing the position of FIG. 125 with the saw blade advanced to cut the metatarsus.

Referring to FIGS. 123 and 124, the outer stage 3206 is affixed to a first portion of the bone, for example at or near the metatarsal head, with fixation members 3460, e.g. pins, screws, bands, or the like. The handle 3208 is affixed at a second portion of the bone proximal to the first portion.

A cutter is engaged with the cutter guide and advanced to cut the bone. In the illustrative example of FIGS. 125 and 126 a saw blade 3400 is engaged with the saw slot 3246 and reciprocated via a powered handpiece 3404 to separate the metatarsus into a distal portion affixed to the outer stage 3206 and a proximal portion affixed to the handle 3208.

If more than a 2 mm osteotomy reduction is desired, the inner stage 3204 is adjusted to the desired amount of reduction by pressing the button 3260 to unlock the stage and sliding it to reposition the cutter guide for a second cut. In the illustrative example of FIGS. 127 and 128, the inner stage 3204 is adjusted to remove bone corresponding to a 6 mm osteotomy as indicated by the alignment of the reference mark 3262 with the indicia 3286 labeled "6".

Figure 129:
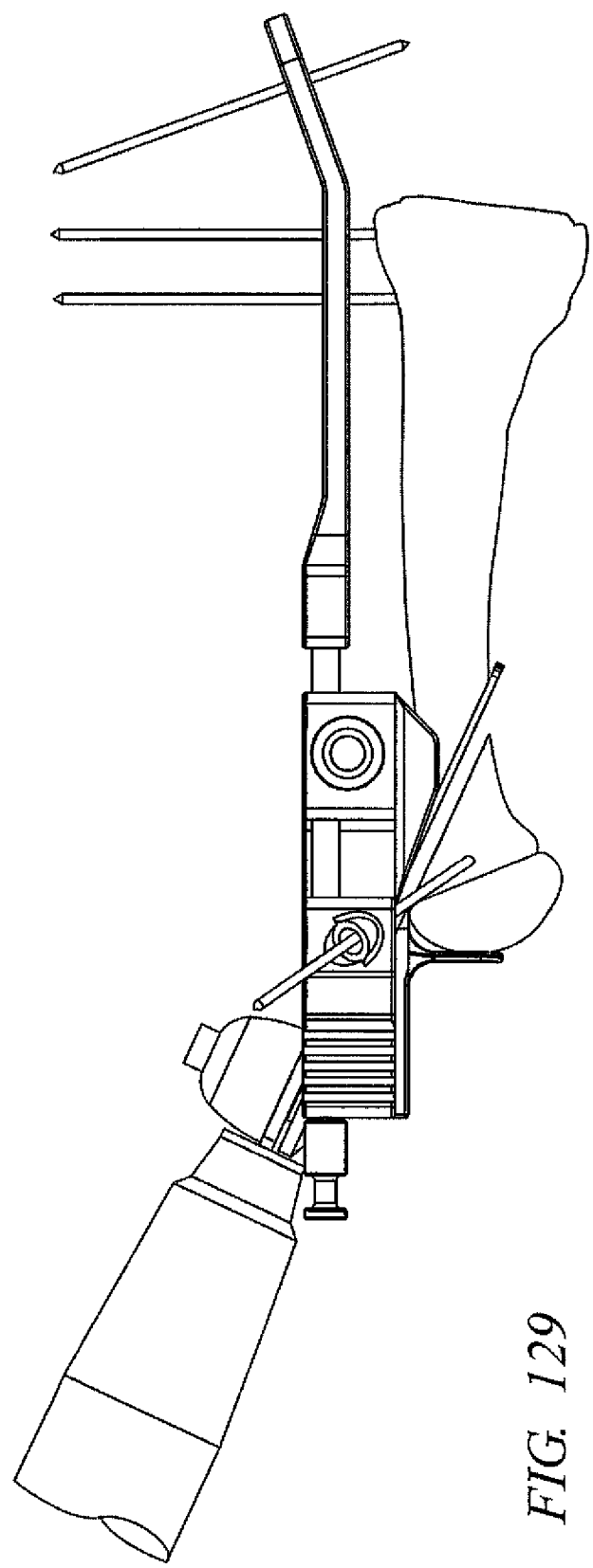
FIG. 129 is a side elevation view of the guide of FIG. 103 showing the position of FIG. 127 with the saw blade advanced to cut the metatarsus.

The saw blade is advanced a second time to cut the bone and any loose pieces of bone are removed to yield the desired osteotomy as shown in FIG. 129.

The osteotomy is reduced by moving the outer stage with the attached metatarsal head until the osteotomy is closed. In the illustrative example of FIGS. 130 and 131, the button 3284 is pressed to unlock the outer stage 3206 and the outer stage 3206 and affixed metatarsal head 3110 are translated proximally parallel to the guide axes 3216, 3217 until the distal portion of bone abuts the proximal portion of bone and the osteotomy is closed. Complete reduction is also indicated by the arrow 3452 aligning with the reference mark 3264.

One or more fixation devices, e.g. a screw, pin, wire, cable, or the like, may be used to affix the proximal and distal portions of bone. For example pins may be inserted through the metatarsus to join the portions of bone. Pins may be inserted freehand or guided. In the illustrative example of FIGS. 130 and 131, pins 3454 are inserted by guiding them in grooves 3245 to orient them at a desired angle relative to the osteotomy; for example perpendicular to the osteotomy.

Figures 132, 133:
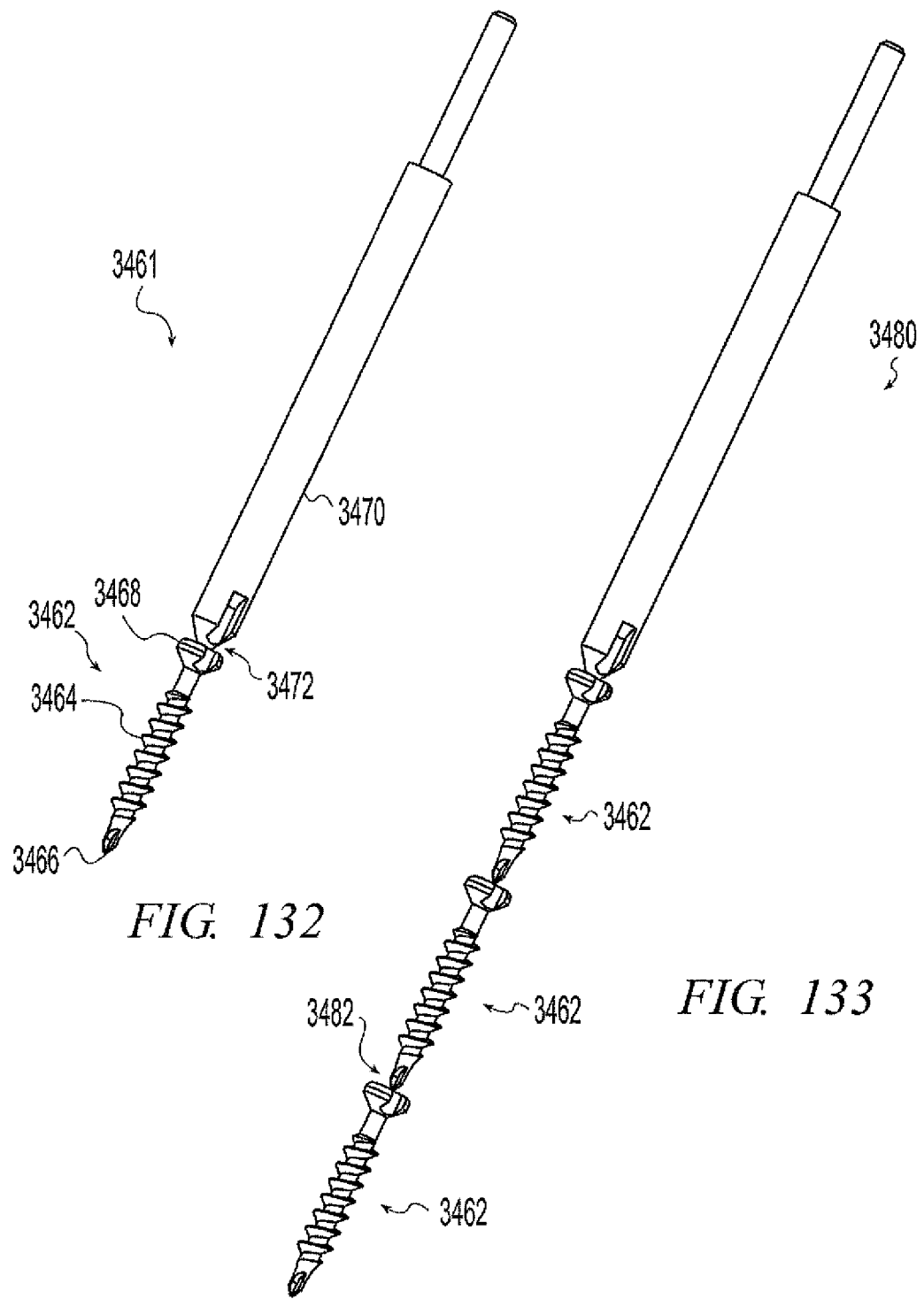
FIG. 132 is a perspective view of an osteotomy fixation screw according to the present invention.
FIG. 133 is a perspective view of an osteotomy fixation screw according to the present invention.

FIG. 132 depicts an illustrative example of a screw assembly 3461 useable as an alternative to pins 3454 to join the bone portions. The screw assembly 3461 includes a screw 3462 having a threaded shaft 3464 with a distal self-drilling, self-tapping tip 3466 and a proximal head 3468. A driver 3470 is joined to the head 3468 of the screw in torque transmitting relationship. In the illustrative embodiment of FIG. 132 the screw 3462 and driver 3470 are formed as a unitary member with a tapered connecting portion 3472 able to transmit torque but able to be broken by bending the assembly at the portion 3472.

FIG. 133 depicts an illustrative example of a screw assembly 3480 similar to assembly 3461 but having three screws 3462 stacked to form the assembly. In use, after the distal screw is driven, it is separated from the others by bending at tapered connection 3482. Each subsequent screw may be driven and separate in like manner. In this way, three screws may be driven in quick succession without the need to take time to load each individual screw on a driver or change the driver and without risk of dropping a screw.

Figure 134:
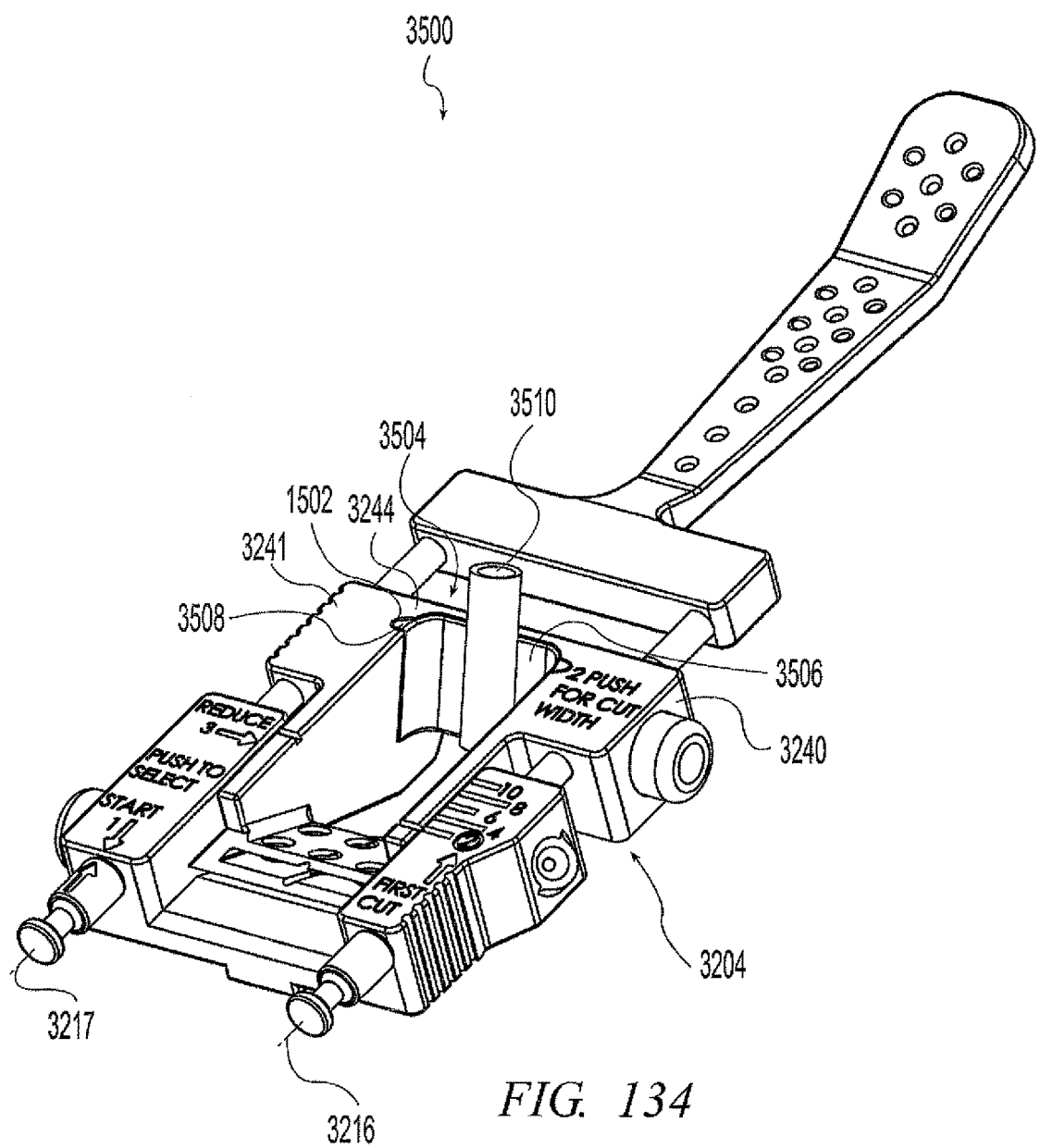
FIG. 134 is a perspective view of an illustrative example of a guide according to the present invention.

FIG. 134 depicts an illustrative example of a guide 3500 similar to the illustrative guide 3200 of FIGS. 103-111. However, guide 3500 includes slots 3502 in the sides 3240, 3241 of the inner stage 3204 near the second end wall 3244 to receive a modular drill/fastener guide 3504 having a frame 3506 with outwardly extending tabs 3508 engageable with the slots 3502. A tubular guide member 3510 is mounted on the frame 3506. The tabs and slots allow the drill/fastener guide 3504 to be engaged with the inner stage 3204 in predetermined known relationship to the guide axes 3216, 3217 and thus the osteotomy when the axes 3216, 3217 are aligned with the bone axis 3108. In use, after the osteotomy is reduced, the drill/fastener guide 3504 is mounted on the inner stage 3204 and used to guide drills, pins, screws or any other suitable member into the underlying bone in a predetermined orientation. In an alternative example, the drill/fastener guide 3504 is permanent part of the guide 3500.

The illustrative instruments and methods have been shown in use to create and reduce an osteotomy on a metatarsal bone adjacent the second MTP joint of the human foot. However, guides and methods within the scope of the invention may be used with any bone in the foot, hand, or other part of a patient's body. Likewise, the illustrative instruments and methods have been shown in use to carry out a constrained, axial, linear reduction of the osteotomy. However, other reductions also fall within the scope of the invention. For example, the guide can be configured to move the cut portions of bone linearly at some angle transverse to the bone axis to produce an offset reduction. In another example, the guide can be configured to move the cut portions of bone relatively along a curved path such as for example for reducing a wedge osteotomy. For example, the guide may include hinges, curved tracks, or the like to produce any desired reduction motion.

The illustrative instrument has been shown with a base, inner stage, and outer stage. However, the first and second stages may be mounted for relative motion without the need for a separate base member. For example, the first stage may be connected to a first bone portion and the second stage may be connected to a second bone portion. The first stage may include a cutter guide to guide a cutter to cut the bone. The first stage may include additional cutter guides to guide additional cuts. For example the first stage may include a series of spaced apart saw blade slots to guide a saw blade to remove a desired thickness of bone. The stages may then be moved relative to one another to reduce the osteotomy.

What is claimed is:

1. A suture passer for passing a suture, the suture passer comprising:
    a housing defining a linear motion axis extending proximally to distally;
    a needle mounted for translation along the motion axis between a first proximal position and a second distal position; and
    a foot mounted to the housing, the foot having a distal portion with a proximal facing surface extending along a distal portion axis crossing the motion axis, the distal portion having a distal facing surface, the distal portion axis forming an angle relative to the motion axis, the distal portion including an opening that extends through both the proximal facing surface and the distal facing surface, and which is aligned with the motion axis and positioned to receive the needle in the second position, and wherein the foot defines a hole that extends about a central hole axis through the distal facing surface and through a sidewall of the opening such that the hole in the sidewall is distally offset from the proximal facing surface, the central hole axis arranged non-parallel to the motion axis and extending along a centerline of the hole, the hole being in communication with the opening and positioned to provide passage of the suture through the distal portion from the distal facing surface to the sidewall of the opening.

2. The suture passer of claim 1 wherein the angle between the distal portion axis and the motion axis is in the range of 25 to 55 degrees.

3. The suture passer of claim 2 wherein the angle between the distal portion axis and the motion axis is in the range of 35 to 45 degrees.

4. The suture passer of claim 1 wherein the foot further comprises a proximal portion with a distal facing surface extending along a proximal portion axis diverging distally away from the motion axis, the proximal portion axis forming an angle relative to the motion axis, the distal portion extending distally from the proximal portion.

5. The suture passer of claim 4 wherein the angle between the distal portion axis and the motion axis is in the range of 25 to 55 degrees.

6. The suture passer of claim 5 wherein the angle between the distal portion axis and the motion axis is in the range of 35 to 45 degrees.

7. The suture passer of claim 1 wherein the distal portion has a proximal end and a distal end, the proximal end of the distal portion coupled to a proximal portion of the foot, the hole terminating at a side of the sidewall of the opening that is generally opposite of another side of the opening from which a groove extends, and a notch in the distal end adjacent the groove, the hole, groove and notch being operable to form a pathway that receives the suture through the distal portion, and from which the suture can extend across the needle receiving opening, along the proximally facing surface, and around the distal end.

8. The suture passer of claim 1 wherein the proximal facing surface of the distal portion defines a plane and the needle further comprises a shaft having a notch formed therein, the notch crossing the plane defined by the proximally facing surface as the needle moves between the first and second positions, the notch being operable to engage the suture in the second position and impart a proximally directed force on the suture as the needle moves toward the first position.

9. The suture passer of claim 8 wherein the notch extends into the needle shaft at a notch angle relative to the motion axis, the notch having an opening at a surface of the needle shaft, the opening facing generally proximally, the notch angle being in the range of 35 to 55 degrees.

10. The suture passer of claim 8 wherein the shaft has a first side surface, the notch being formed into the first side surface, the shaft tapering distally to define a bevel on the first side surface distal to the notch, the bevel being operable to engage the suture as the needle is moved to the second position.

11. The suture passer of claim 1 wherein the angle between the hole axis and the motion axis is about 90 degrees.

12. The suture passer of claim 1 wherein the distal portion extends between an elbow of the foot and a distal end of the distal portion, wherein the opening extends through the distal facing surface of the distal portion, and wherein the hole is located on the distal facing surface of the distal portion at a location between the elbow and a location at which the opening extends through the distal facing surface of the distal portion.

13. The suture passer of claim 12 wherein the distal portion further includes a groove in the proximally facing surface, and wherein the groove is positioned on the proximally facing surface at a location between the opening and the distal end of the distal portion.

14. The suture passer of claim 13 wherein the groove terminates at a notch in the distal end of the distal portion.

15. The suture passer of claim 14 wherein the elbow couples the distal portion to a proximal portion of the foot, and wherein the proximal portion is positioned between the elbow and the housing.

16. A suture passer comprising:
    a housing defining a linear motion axis extending proximally to distally;
    a handle mounted to the housing;
    a needle mounted coaxial with the motion axis for axial translation between a first proximal position and a second distal position, the needle remaining coaxial with the motion axis throughout its range of motion; and
    a foot mounted to the housing, the foot having a distal portion with a proximal facing surface extending along a distal portion axis crossing the motion axis and a distal facing surface, the distal portion axis forming an angle relative to the motion axis, the distal portion including an opening that extends through both the proximal facing surface and the distal facing surface, and which is aligned with the motion axis and positioned to receive the needle in the second position, and wherein the foot defines a hole that extends through the distal facing surface and is positioned in communication with the opening, the hole extending from the distal facing surface to the opening and through a sidewall of the opening such that the hole in the sidewall is distally offset from the proximal facing surface, the hole extending about a central hole axis arranged non-parallel to the motion axis and extending along a centerline of the hole that intersects the motion axis, and wherein the hole is positioned at a location along the distal portion that is offset from the range of motion of the needle and is sized to receive passage of the suture through the distal portion from the distal facing surface to the sidewall of the opening.

17. A suture passer comprising:
a housing defining a linear motion axis extending proximally to distally;
a handle mounted to the housing;
a needle mounted for translation along the motion axis between a first proximal position and a second distal position; and
a foot mounted to the housing, the foot having a first suture capture feature and a second suture capture feature for constraining a suture under tension to a linear suture path at an angle relative to the linear motion axis, wherein the first suture capture feature extends along an axis that intersects the motion axis, wherein the first suture capture feature fully encloses the suture and the second suture capture feature partially encloses the suture, and wherein the first and second suture capture features are in communication with an opening in the foot, the opening positioned to receive the needle in the second position,
wherein the first suture capture feature extends through a distal facing surface of a distal portion, and
wherein the distal portion is coupled to a proximal portion of the foot by an elbow, and wherein the first suture capture feature extends through the distal facing surface of the distal portion at a location between the elbow and a location at which the opening extends through the distal facing surface of the distal portion.

18. A system comprising:
a suture having a diameter;
a suture passer comprising
a housing defining a linear motion axis extending proximally to distally;
a needle mounted for translation along the motion axis between a first proximal position and a second distal position, the needle having a shaft and a notch formed in the shaft, the notch having a width measured parallel to the motion axis and a depth measured perpendicular to the motion axis, the notch width being in the range of one to one and one-half times the suture diameter and the notch depth being in the range of one to two times the suture diameter; and
a foot mounted to the housing, the foot having a distal portion with a proximal facing surface extending along a distal portion axis crossing the motion axis, the distal portion having a distal facing surface, the distal portion axis forming an angle relative to the motion axis, the distal portion including an opening that extends from the proximal facing surface to the distal facing surface along an axis that is coaxial with the motion axis and is positioned to receive the needle in the second position, and wherein the opening is in communication with an enclosed hole extending through the distal facing surface, the enclosed hole sized to provide a passageway for the suture through the distal portion to the opening, the hole having a central axis that is non-parallel to the motion axis.

\* \* \* \* \*